United States Patent [19]

Shibata et al.

[11] Patent Number: 5,574,064
[45] Date of Patent: Nov. 12, 1996

[54] AMINO-ACID AMIDE DERIVATIVES, AGRICULTURAL OR HORTICULTURAL FUNGICIDES, AND METHOD FOR PRODUCING THE SAME

[75] Inventors: Masaru Shibata; Kazuhiko Sugiyama; Norihisa Yonekura, all of Iwata-gun; Junetsu Sakai, Ogasa-gun; Yoshiyuki Kojima, Kakegawa; Shigeru Hayashi, Ogasa-gun, all of Japan

[73] Assignees: Kumiai Chemical Industry Co., Ltd.; Ihara Chemical Industry Co., Ltd., both of Tokyo, Japan

[21] Appl. No.: 356,316

[22] PCT Filed: Apr. 27, 1994

[86] PCT No.: PCT/JP94/00708

§ 371 Date: Dec. 28, 1994

§ 102(e) Date: Dec. 28, 1994

[87] PCT Pub. No.: WO94/25432

PCT Pub. Date: Nov. 10, 1994

[30] Foreign Application Priority Data

Apr. 28, 1993 [JP] Japan ................................ 5-125455

[51] Int. Cl.$^6$ ................... A01N 37/18; C07C 271/22; C07C 333/04

[52] U.S. Cl. .................. 514/542; 514/506; 514/513; 514/540; 558/234; 558/236; 558/238; 558/413; 558/414; 558/416; 558/418; 560/17; 560/24; 560/29

[58] Field of Search .................. 514/506, 513, 514/540, 542; 558/234, 238, 241, 242, 236, 413, 414, 416, 418; 560/16, 17, 24, 29

[56] References Cited

FOREIGN PATENT DOCUMENTS

| | | |
|---|---|---|
| 0554729 | 8/1993 | European Pat. Off. . |
| 0587110 | 3/1994 | European Pat. Off. . |
| 4308507 | 8/1992 | Japan . |
| 4230653 | 8/1992 | Japan . |
| 4230652 | 8/1992 | Japan . |

OTHER PUBLICATIONS

Jamontaite et al. CA:437540, 1974.
Analytical Biochemistry, vol. 192, No. 2, Feb. 1, 1991, pp. 419–425, Jair R. Chagas, et al., "Intramolecularly Quenched Fluorogenic Tetrapeptide Substrates for Tissue and Plasma Kallikreins".

Chemical Abstracts, vol. 106, No. 9, Mar. 2, 1987, p. 649, AN–67647s.

Chemical Abstracts, vol. 81, No. 7, Aug. 19, 174, p. 388, AN–37540z.

Acta Chemica Scandinavica, vol. B42, No. 8, 1988, pp. 556–562, Christer Sahlberg, et al., "Synthesis of a Tritiated LPS Inhibitor Derived From 3–Deoxy–D–Manno–2–Octulosonic acid (KDO). A Cautionary Note Regarding Amide Synthesis from Azides Via Phosphine Imines".

Primary Examiner—Yogendra N. Gupta
Attorney, Agent, or Firm—Oblon, Spivak, McClelland, Maier & Neustadt, P.C.

[57] ABSTRACT

The present invention provides an agricultural or horticultural fungicide including an effective amount of an amino-acid derivative represented by the formula:

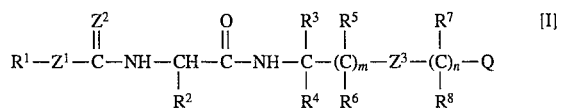

wherein $R^1$ represents a lower alkyl group (optionally having at least one same or different substituent of a halogen atom, an alkoxy group, and a cyano group), $R^2$ represents an ethyl group, or an n-propyl group, $R^3$ represents a hydrogen atom or a lower alkyl group, $R^4$ represents a hydrogen atom, $R^5$, $R^6$, and $R^7$ independently represent a hydrogen atom or a lower alkyl group, $R^8$ represents a hydrogen atom, or a lower alkyl group, $Z^1$ and $Z^2$ independently represent an oxygen atom or a sulfur atom, $Z^3$ represents an oxygen atom, or a sulfur atom, Q represents a phenyl group, m represents an integer from 0 to 2, and n represents 0 or 1.

The amino-acid amide derivatives according to the present invention exhibit superior control of cucumber downy mildew (*Pseudoperonospora cubensis*), tomato late blight (*Phytophthora infestans*), and grape downy mildew (*Plasmopara viticola*), and are effective for potato late blight (*Phytophthora infestans*). In addition, the agricultural or horticultural fungicides of the present invention are also characterized in that they are not harmful chemicals and exhibit excellent characteristics such as systemic action, residual activity, and persistence after rain-fall.

9 Claims, No Drawings

AMINO-ACID AMIDE DERIVATIVES, AGRICULTURAL OR HORTICULTURAL FUNGICIDES, AND METHOD FOR PRODUCING THE SAME

FIELD OF THE INVENTION

The present invention relates to an amino-acid amide derivative as well as to an agricultural or horticultural fungicide containing the same as an active ingredient. The present invention also relates to a process for preparing the same.

BACKGROUND OF THE ART

Amino-acid amide derivatives have been disclosed as intermediates for medicines in Japanese Patent Application, First Publication Nos. Sho 56-8352 and Sho 62-89696. However, these documents fail to disclose the utility of the amino-acid amide derivatives. Although Japanese Patent Application First Publication Nos. Hei 3-5451, Hei 3-153657, Hei 4-230652, Hei 4-230653, Hei 4-283554, Hei 4-308507, and Hei 4-338372 disclose that some amino-acid amides are useful for biocides, the compounds disclosed in these documents are different from the amino-acid amide derivatives according to the present invention.

DISCLOSURE OF THE INVENTION

The present inventors have synthesized various amino-acid amide derivatives and have carried out extensive research in connection with their effects on the physiological activities of fungi. As a result, we have found that the compounds according to the present invention exhibit a broad spectrum of anti-fungal activity especially against cucumber downy mildew, grape downy mildew, and tomato late blight, and at the same time they do not hinder desirable plant growth.

According to an aspect of the present invention, there is provided an amino-acid amide derivative represented by the formula:

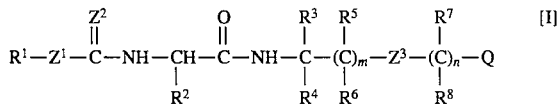

wherein $R^1$ represents a lower alkyl group (optionally having at least one same or different substituent selected from the group consisting of a halogen atom, an alkoxy group, and a cyano group), a lower alkenyl group, a lower alkynyl group, a cycloalkyl group (optionally having at least one same or different substituent selected from the group consisting of methyl group and a halogen atom), a cycloalkylalkyl group, a cycloalkenyl group, an alkylene oxide group, an aralkyl group (optionally having at least one same or different substituent selected from the group consisting of a methyl group, a cyano group, and a nitro group), a phenyl group (optionally having at least one same or different substituent selected from the group consisting of a halogen atom, a lower alkyl group which may be substituted with a same or different halogen atom, a lower alkoxy group which may be substituted with a same or different halogen atom, a cyano group, and a nitro group), or a heterocyclic group, $R^2$ represents an ethyl group, an n-propyl group, an isopropyl group, an isobutyl group, a sec-butyl group, a tert-butyl group, an alkenyl group, a cycloalkyl group, a phenyl group (optionally having at least one substituent of halogen atom), $R^3$ represents a hydrogen atom or a lower alkyl group, $R^4$ represents a hydrogen atom, a lower alkyl group, or a cyano group, $R^5$, $R^6$, and $R^7$ independently represent a hydrogen atom or a lower alkyl group, $R^8$ represents a hydrogen atom, a lower alkyl group, an aralkyl group, a phenyl group, an alkoxycarbonyl group, or a cyano group, $Z^1$ and $Z^2$ independently represent an oxygen atom or a sulfur atom, $Z^3$ represents an oxygen atom, a sulfur atom, a group $N-R^{10}$ (wherein $R^{10}$ represents a hydrogen atom, a methyl group, a methylcarbonyl group, a phenylcarbonyl group, a methoxycarbonyl group, or a methoxymethyl group), a sulfinyl group, a sulfonyl group, a group COO, a group $CONR^{11}$ (wherein $R^{11}$ represents a hydrogen atom or a lower alkyl group), Q represents a phenyl group [optionally having at least one same or different substituent selected from the group consisting of a halogen atom, a lower alkyl group which may be substituted with at least one same or different halogen atom, a lower alkoxy group which may be substituted with a same or different halogen atom, a cyano group, a nitro group, a lower alkoxycarbonyl group, a methylsulfonyl group, a methylsulfinyl group, a methylthio group which may be substituted with a halogen atom, a dimethylamino group, a phenylsulfonyl group, an acyl group, and a phenyl group], an alkylene oxide group, a heterocyclic group (optionally having a substituent selected from the group consisting of a halogen atom, an alkyl group, a trifluoromethyl group, and a nitro group), or a condensed heterocyclic group optionally having a substituent selected from the group consisting of a halogen atom and a nitro group, m represents an integer from 0 to 2, and n represents 0 or 1, and an agricultural or horticultural fungicide containing the same as the active ingredient.

The terms employed in the present invention are defined as follows. The term "alkyl group" is used herein to mean a straight or branched alkyl group possessing 1 to 6 carbon atoms including, but not limited to, a methyl group, ethyl group, n-propyl group, isopropyl group, n-butyl group, isobutyl group, sec-butyl group, tert-butyl group, n-pentyl group, 1-methylbutyl group, 2-methylbutyl group, 3-methylbutyl group, 2,2-dimethylpropyl group, 1,1-dimethylpropyl group, 1-ethylpropyl group, n-hexyl group, or the like.

The term "halogen atom" is used herein to mean a fluorine atom, chlorine atom, bromine atom, or iodine atom.

The term "lower alkenyl group" is used herein to mean a straight or branched alkenyl group possessing 2 to 6 carbon atoms and including, but not limited to, a vinyl group, 1-propenyl group, 2-propenyl group, isopropenyl group, 1-butenyl group, 2-butenyl group, 3-butenyl group, 1-methyl-1-propenyl group, 2-methylpropenyl group, 1-ethylvinyl group, or the like.

The term "lower alkynyl group" is used herein to mean a straight or branched alkynyl group possessing 2 to 6 carbon atoms and including, for example, an ethynyl group, propynyl group, butynyl group, 1-methyl-2-propynyl group, or the like.

The term "cycloalkyl group" is used herein to mean a cycloalkyl group possessing 3 to 8 carbon atoms and including, but not limited to, a cyclopropyl group, cyclobutyl group, cyclopentyl group, cyclohexyl group, cycloheptyl group, or the like.

The term "cycloalkenyl group" is used herein to mean a cycloalkenyl group possessing 4 to 8 carbon atoms and including, for example, a cyclobutenyl group, cyclopentenyl group, cyclohexenyl group, cycloheptenyl group, or the like.

The term "aralkyl group" is used herein to mean an aralkyl group possessing 7 to 8 carbon atoms and including, but not limited to, a benzyl group, phenethyl group, or the like.

The term "alkylene oxide group" is used herein to mean an alkylene oxide group possessing 2 to 6 carbon atoms and including, for example, an oxiranyl group, oxetanyl group, tetrahydrofuranyl group, tetrahydropyranyl group, or the like.

The preferred compounds of the present invention are represented by formula [I], wherein $R^1$ represents a straight or branched alkyl group possessing 2 to 6 carbon atoms, a straight or branched alkenyl group possessing 3 carbon atoms, a cycloalkyl group possessing 5 to 6 carbon atoms, or a phenyl group optionally having a substituent; $R^2$ represents an ethyl group, an n-propyl group, an isopropyl group, or a sec-butyl group; $R^3$ represents a hydrogen atom or a methyl group; $R^4$ represents a hydrogen atom or a methyl group; $R^5$ represents a hydrogen atom or a methyl group; $R^6$ represents a hydrogen atom or a methyl group; Q represents a phenyl group optionally having a substituent; m represents an integer of 0 or 1; n represents 0; $Z^1$, $Z^2$, and $Z^3$ represent an oxygen atom or a sulfur atom; and the amino acid is an L-isomer.

The compounds represented by formula [I] according to the present invention can exist in stereoisomers by virtue of the presence of two or more chiral centers. The present invention relates to all such stereoisomers, including diastereomers, enantiomers, and mixtures thereof, which can be separated by appropriate methods.

Next, the compounds represented by formula [I] according to the present invention are listed in Tables 1 to 12. However, it should be understood that the invention is not limited to these compounds. The compound Numbers given in Tables 1 to 12 will be referred to in the subsequent description.

In Tables 1 to 12, Compound Nos. 108, 433, 456, 459, 460, 461, 462, 464, 467, 470, 471,472, and 475 possess D,L-configurational amino acid moieties; Compound No. 109 possesses a D-configurational amino acid moiety; Compound Nos. 233, 234, 235, 236, 237, 238, 425, 426, 427 possess (2S)-butyric acid moieties; and the compounds other than the compounds described above possess L-configurational amino acid moieties. Compound Nos. 33, 345, and 346; Compound Nos. 107, 116, and 117; Compound Nos. 135, 395, and 396; Compound Nos. 228, 414, and 415; and Compound Nos. 452, 453, and 454 are mixtures of diastereomers, and are also individual diastereomers. In addition, Compound Nos. 26 and 27; Compound Nos. 45 and 356; Compound Nos. 335 and 336; Compound Nos. 397 and 401; and Compound Nos. 409 and 410 are mixtures of diastereomers, and are also one of the individual diastereomers, respectively. Compound No. 108 is a mixture of four isomers and Compound No. 433 is a mixture of two isomers. Compound Nos. 483 to 501,504, 505, 510 to 518, 521, and 522 are L-Val-DL-Ala; Compound Nos. 502, 503, 508, 509, 519, and 525 are L-Val-D-Ala; Compound No. 520 is L-Val-L-Ala; Compound Nos. 506 and 523 are L-Ile-D-Ala; Compound No. 526 is L-Val-Gly; and Compound Nos. 507 and 524 are (2S)-butylyl-D-Ala.

In the tables of the present specification, the expressions "$C_3H_7$-i", "$C_4H_9$-t", "$C_4H_9$-s", and "$C_4H_9$-i" are used to indicate an isopropyl group, a tert-butyl group, a sec-butyl group, and an isobutyl group, respectively.

TABLE 1

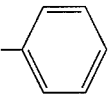

| Compound No. | $R^1$ | $R^9$ | $Z^1$ | $Z^2$ | $Z^3$ | A | Melting Point (°C.) or Refractive Index ($n_D^{20}$) |
|---|---|---|---|---|---|---|---|
| 1 | $C_4H_9$-t | $CH_3$ | O | O | O | phenyl | 88–92 |

TABLE 1-continued $$R^1-Z^1-\overset{\overset{Z^2}{\|}}{C}-NH-\underset{\underset{\underset{R^9}{|}}{\overset{|}{CH}}}{\overset{|}{CH}}-\overset{\overset{O}{\|}}{C}-NH-\underset{\underset{CH_3}{|}}{\overset{|}{CH}}-CH_2Z^3-A$$
$$\phantom{R^1-Z^1-\overset{Z^2}{C}-NH-}\underset{CH_3}{|}$$

| Compound No. | $R^1$ | $R^9$ | $Z^1$ | $Z^2$ | $Z^3$ | A | Melting Point (°C.) or Refractive Index ($n_D^{20}$) |
|---|---|---|---|---|---|---|---|
| 2 | $C_4H_9$-t | $CH_3$ | O | O | O | 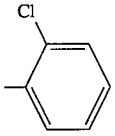 2-Cl-phenyl | 98–100 |
| 3 | $C_4H_9$-t | $CH_3$ | O | O | O | 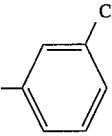 3-Cl-phenyl | 1.5051 |
| 4 | $C_4H_9$-t | $CH_3$ | O | O | O | 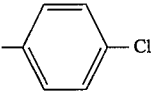 4-Cl-phenyl | 97–98 |
| 5 | $C_4H_9$-t | $CH_3$ | O | O | O | 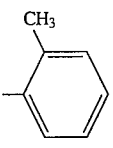 2-CH$_3$-phenyl | 77–80 |
| 6 | $C_4H_9$-t | $CH_3$ | O | O | O | 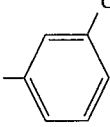 3-CH$_3$-phenyl | 1.5051 |
| 7 | $C_4H_9$-t | $CH_3$ | O | O | O | 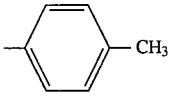 4-CH$_3$-phenyl | 99–101 |
| 8 | $C_4H_9$-t | $CH_3$ | O | O | O | 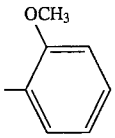 2-OCH$_3$-phenyl | 86–89 |
| 9 | $C_4H_9$-t | $CH_3$ | O | O | O | 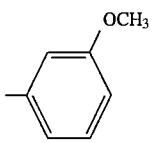 3-OCH$_3$-phenyl | 1.4899 |
| 10 | $C_4H_9$-t | $CH_3$ | O | O | O | 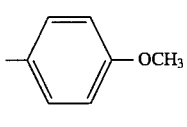 4-OCH$_3$-phenyl | 86–89 |
| 11 | $C_4H_9$-t | $CH_3$ | O | O | O | 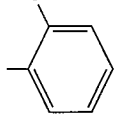 2-CN-phenyl | |

TABLE 1-continued $$R^1-Z^1-\overset{\overset{Z^2}{\|}}{C}-NH-\underset{\underset{\underset{CH_3}{|}}{\overset{|}{CH}}}{\overset{|}{CH}}-NH-\underset{\underset{CH_3}{|}}{\overset{|}{CH}}-CH_2Z^3-A$$

| Compound No. | R¹ | R⁹ | Z¹ | Z² | Z³ | A | Melting Point (°C.) or Reflactive Index ($n_D^{20}$) |
|---|---|---|---|---|---|---|---|
| 12 | $C_4H_9$-t | $CH_3$ | O | O | O | 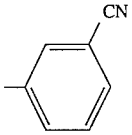 3-CN-phenyl | 83–87 |
| 13 | $C_4H_9$-t | $CH_3$ | O | O | O | 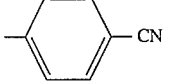 4-CN-phenyl | 53–56 |
| 14 | $C_4H_9$-t | $CH_3$ | O | O | O | 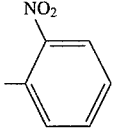 2-$NO_2$-phenyl | 1.5081 |
| 15 | $C_4H_9$-t | $CH_3$ | O | O | O | 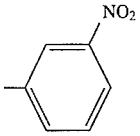 3-$NO_2$-phenyl | 112–114 |
| 16 | $C_4H_9$-t | $CH_3$ | O | O | O | 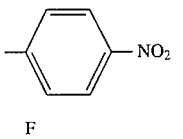 4-$NO_2$-phenyl | 105–107 |
| 17 | $C_4H_9$-t | $CH_3$ | O | O | O | 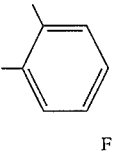 2-F-phenyl | 95–97 |
| 18 | $C_4H_9$-t | $CH_3$ | O | O | O | 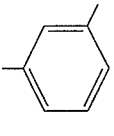 3-F-phenyl | 89–92 |
| 19 | $C_4H_9$-t | $CH_3$ | O | O | O | 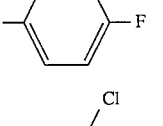 4-F-phenyl | 85–89 |
| 20 | $C_4H_9$-t | $CH_3$ | O | O | O | 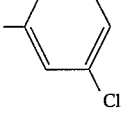 3,5-diCl-phenyl | 99–100 |
| 21 | $C_4H_9$-t | $CH_3$ | O | O | O | 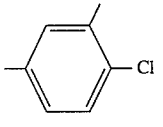 3,4-diCl-phenyl | 102–104 |

TABLE 1-continued $$R^1-Z^1-\underset{\underset{Z^2}{\|}}{C}-NH-\underset{\underset{\underset{R^9}{|}}{\overset{|}{CH}}}{CH}-\underset{\overset{\|}{O}}{C}-NH-\underset{\underset{CH_3}{|}}{CH}-CH_2Z^3-A$$

| Compound No. | $R^1$ | $R^9$ | $Z^1$ | $Z^2$ | $Z^3$ | A | Melting Point (°C.) or Refractive Index ($n_D^{20}$) |
|---|---|---|---|---|---|---|---|
| 22 | $C_4H_9$-t | $CH_3$ | O | O | O | 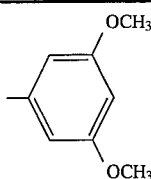 3,5-(OCH$_3$)$_2$-C$_6$H$_3$ | 87–91 |
| 23 | $C_4H_9$-t | $CH_3$ | O | O | O | 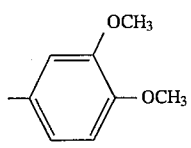 3,4-(OCH$_3$)$_2$-C$_6$H$_3$ | 88–90 |
| 24 | $C_4H_9$-t | $CH_3$ | O | O | O | 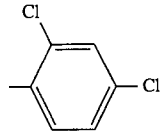 2,4-Cl$_2$-C$_6$H$_3$ | 98–103 |
| 25 | $C_4H_9$-t | $CH_3$ | O | O | O | 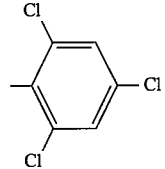 2,4,6-Cl$_3$-C$_6$H$_2$ | 120–125 |
| 26 | $C_4H_9$-t | $CH_3$ | O | O | O | 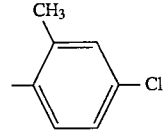 2-CH$_3$-4-Cl-C$_6$H$_3$ | 108–110 |
| 27 | $C_4H_9$-t | $CH_3$ | O | O | O | 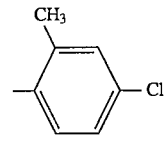 2-CH$_3$-4-Cl-C$_6$H$_3$ | 143–146 |
| 28 | $C_4H_9$-t | $CH_3$ | O | O | O | 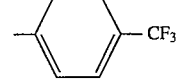 4-CF$_3$-C$_6$H$_4$ | 115–117 |
| 29 | $C_4H_9$-t | $CH_3$ | O | O | O | 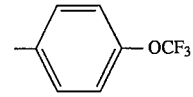 4-OCF$_3$-C$_6$H$_4$ | 94–98 |
| 30 | $C_3H_7$-i | $CH_3$ | O | O | O | 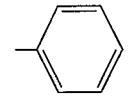 C$_6$H$_5$ | |
| 31 | $C_3H_7$-i | $CH_3$ | O | O | O | 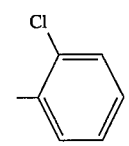 2-Cl-C$_6$H$_4$ | |

TABLE 1-continued $$R^1-Z^1-\overset{\overset{Z^2}{\|}}{C}-NH-CH-\overset{\overset{O}{\|}}{C}-NH-CH-CH_2Z^3-A$$
$$\underset{R^9}{\underset{|}{CH}}\underset{CH_3}{} \quad \underset{CH_3}{|}$$

| Compound No. | $R^1$ | $R^9$ | $Z^1$ | $Z^2$ | $Z^3$ | A | Melting Point (°C.) or Refractive Index ($n_D^{20}$) |
|---|---|---|---|---|---|---|---|
| 32 | $C_3H_7$-i | $CH_3$ | O | O | O | 3-Cl-phenyl | |
| 33 | $C_3H_7$-i | $CH_3$ | O | O | O | 4-Cl-phenyl | 149–152 |
| 34 | $C_3H_7$-i | $CH_3$ | O | O | O | 2-CH$_3$-phenyl | |
| 35 | $C_3H_7$-i | $CH_3$ | O | O | O | 3-CH$_3$-phenyl | |
| 36 | $C_3H_7$-i | $CH_3$ | O | O | O | 4-CH$_3$-phenyl | |
| 37 | $C_3H_7$-i | $CH_3$ | O | O | O | 2-OCH$_3$-phenyl | |
| 38 | $C_3H_7$-i | $CH_3$ | O | O | O | 3-OCH$_3$-phenyl | |
| 39 | $C_3H_7$-i | $CH_3$ | O | O | O | 4-OCH$_3$-phenyl | |
| 40 | $C_3H_7$-i | $CH_3$ | O | O | O | 2-CN-phenyl | |
| 41 | $C_3H_7$-i | $CH_3$ | O | O | O | 3-CN-phenyl | |

TABLE 1-continued $$R^1-Z^1-\overset{\overset{Z^2}{\|}}{C}-NH-\underset{\underset{\underset{CH_3}{|}}{\overset{|}{CH}}}{\overset{|}{CH}}-\overset{\overset{O}{\|}}{C}-NH-\underset{\underset{CH_3}{|}}{\overset{|}{CH}}-CH_2Z^3-A$$

| Compound No. | $R^1$ | $R^9$ | $Z^1$ | $Z^2$ | $Z^3$ | A | Melting Point (°C.) or Refractive Index ($n_D^{20}$) |
|---|---|---|---|---|---|---|---|
| 42 | $C_3H_7$-i | $CH_3$ | O | O | O | 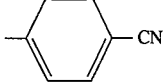 —CN | 149–152 |
| 43 | $C_3H_7$-i | $CH_3$ | O | O | O | 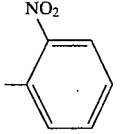 $NO_2$ (ortho) | |
| 44 | $C_3H_7$-i | $CH_3$ | O | O | O | 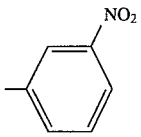 $NO_2$ (meta) | |
| 45 | $C_3H_7$-i | $CH_3$ | O | O | O | 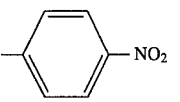 —$NO_2$ | not determined |
| 46 | $C_3H_7$-i | $CH_3$ | O | O | O | 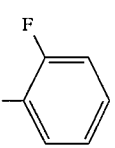 F (ortho) | |
| 47 | $C_3H_7$-i | $CH_3$ | O | O | O | 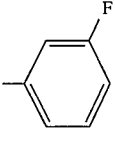 F (meta) | |
| 48 | $C_3H_7$-i | $CH_3$ | O | O | O | 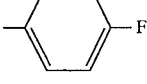 —F | |
| 49 | $C_2H_5$ | $CH_3$ | O | O | O | 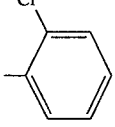 Cl (ortho) | |
| 50 | $C_2H_5$ | $CH_3$ | O | O | O | 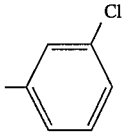 Cl (meta) | |
| 51 | $C_2H_5$ | $CH_3$ | O | O | O | 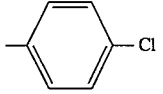 —Cl | |

TABLE 1-continued $$R^1-Z^1-\underset{\underset{}{\overset{Z^2}{\|}}}{C}-NH-\underset{\underset{\underset{R^9}{\overset{|}{CH}}-CH_3}{\overset{|}{CH}}}{CH}-\underset{\overset{O}{\|}}{C}-NH-\underset{\underset{CH_3}{\overset{|}{}}}{CH}-CH_2Z^3-A$$

| Compound No. | R¹ | R⁹ | Z¹ | Z² | Z³ | A | Melting Point (°C.) or Refractive Index ($n_D^{20}$) |
|---|---|---|---|---|---|---|---|
| 52 | $C_2H_5$ | $CH_3$ | O | O | O | 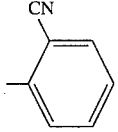 2-CN-phenyl | |
| 53 | $C_2H_5$ | $CH_3$ | O | O | O | 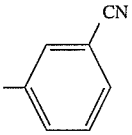 3-CN-phenyl | |
| 54 | $C_2H_5$ | $CH_3$ | O | O | O | 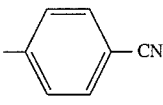 4-CN-phenyl | 112–115 |
| 55 | $C_2H_5$ | $CH_3$ | O | O | O | 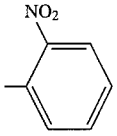 2-$NO_2$-phenyl | |
| 56 | $C_2H_5$ | $CH_3$ | O | O | O | 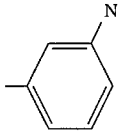 3-$NO_2$-phenyl | |
| 57 | $C_2H_5$ | $CH_3$ | O | O | O | 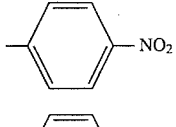 4-$NO_2$-phenyl | |
| 58 | $C_4H_9$-s | $CH_3$ | O | O | O | 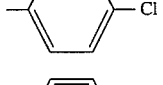 4-Cl-phenyl | |
| 59 | $C_4H_9$-s | $CH_3$ | O | O | O | 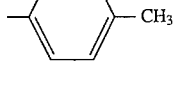 4-$CH_3$-phenyl | |
| 60 | $C_4H_9$-s | $CH_3$ | O | O | O | 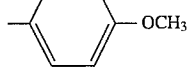 4-$OCH_3$-phenyl | |
| 61 | $C_4H_9$-s | $CH_3$ | O | O | O | 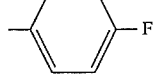 4-F-phenyl | |
| 62 | $C_4H_9$-s | $CH_3$ | O | O | O | 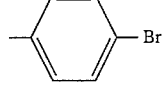 4-Br-phenyl | |

TABLE 1-continued $$R^1-Z^1-\overset{\overset{Z^2}{\|}}{C}-NH-\underset{\underset{\underset{R^9}{|}}{\overset{|}{CH}}}{CH}-\overset{\overset{O}{\|}}{C}-NH-\underset{\underset{CH_3}{|}}{CH}-CH_2Z^3-A$$

| Compound No. | R[1] | R[9] | Z[1] | Z[2] | Z[3] | A | Melting Point (°C.) or Reflactive Index ($n_D^{20}$) |
|---|---|---|---|---|---|---|---|
| 63 | $C_4H_9$-s | $CH_3$ | O | O | O | ―⟨benzene⟩―CN | 140–143 |
| 64 | $C_4H_9$-s | $CH_3$ | O | O | O | ―⟨benzene⟩―$NO_2$ | |
| 65 | $C_4H_9$-s | $CH_3$ | O | O | O | ―⟨benzene⟩―$CF_3$ | |
| 66 | $C_4H_9$-s | $CH_3$ | O | O | O | ―⟨benzene⟩―$OCF_3$ | |
| 67 | $C_4H_9$-s | $CH_3$ | O | O | O | ―⟨benzene, 2-Cl⟩ | |
| 68 | $C_4H_9$-s | $CH_3$ | O | O | O | ―⟨benzene, 3-Cl⟩ | |
| 69 | ―C(CH$_3$)=CH$_2$ | $CH_3$ | O | O | O | ―⟨benzene, 2-Cl⟩ | |
| 70 | ―C(CH$_3$)=CH$_2$ | $CH_3$ | O | O | O | ―⟨benzene, 3-Cl⟩ | |
| 71 | ―C(CH$_3$)=CH$_2$ | $CH_3$ | O | O | O | ―⟨benzene, 4-Cl⟩ | |
| 72 | ―C(CH$_3$)=CH$_2$ | $CH_3$ | O | O | O | ―⟨benzene, 2-$NO_2$⟩ | |
| 73 | ―C(CH$_3$)=CH$_2$ | $CH_3$ | O | O | O | ―⟨benzene, 3-$NO_2$⟩ | |

TABLE 1-continued $$R^1-Z^1-\overset{\overset{Z^2}{\|}}{C}-NH-\underset{\underset{\underset{R^9}{|}}{\overset{|}{CH}}\diagdown CH_3}{CH}-\overset{\overset{O}{\|}}{C}-NH-\underset{\underset{CH_3}{|}}{CH}-CH_2Z^3-A$$

| Compound No. | R¹ | R⁹ | Z¹ | Z² | Z³ | A | Melting Point (°C.) or Refractive Index ($n_D^{20}$) |
|---|---|---|---|---|---|---|---|
| 74 | −C(CH₃)=CH₂ | CH₃ | O | O | O | 4-NO₂-C₆H₄− | |
| 75 | −C(CH₃)=CH₂ | CH₃ | O | O | O | 2-CN-C₆H₄− | |
| 76 | −C(CH₃)=CH₂ | CH₃ | O | O | O | 3-CN-C₆H₄− | |
| 77 | −C(CH₃)=CH₂ | CH₃ | O | O | O | 4-CN-C₆H₄− | 82–86 |
| 78 | −C(CH₃)=CH₂ | CH₃ | O | O | O | 4-CF₃-C₆H₄− | |
| 79 | −C(CH₃)=CH₂ | CH₃ | O | O | O | 4-OCF₃-C₆H₄− | |
| 80 | cyclopentyl | CH₃ | O | O | O | 2-Cl-C₆H₄− | |
| 81 | cyclopentyl | CH₃ | O | O | O | 3-Cl-C₆H₄− | |
| 82 | cyclopentyl | CH₃ | O | O | O | 4-Cl-C₆H₄− | |
| 83 | cyclopentyl | CH₃ | O | O | O | 2-NO₂-C₆H₄− | |

TABLE 1-continued
$$R^1-Z^1-\overset{\overset{Z^2}{\|}}{C}-NH-\underset{\underset{\underset{R^9}{|}}{\overset{|}{CH}}}{CH}-\overset{\overset{O}{\|}}{C}-NH-\underset{\underset{CH_3}{|}}{CH}-CH_2Z^3-A$$
| Compound No. | $R^1$ | $R^9$ | $Z^1$ | $Z^2$ | $Z^3$ | A | Melting Point (°C.) or Reflactive Index ($n_D^{20}$) |
|---|---|---|---|---|---|---|---|
| 84 |  | $CH_3$ | O | O | O | 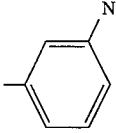 | |
| 85 |  | $CH_3$ | O | O | O | 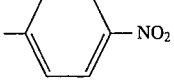 | |
| 86 |  | $CH_3$ | O | O | O | 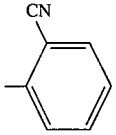 | |
| 87 |  | $CH_3$ | O | O | O | 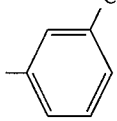 | |
| 88 |  | $CH_3$ | O | O | O | 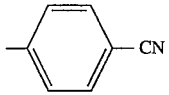 | 145–148 |
| 89 | 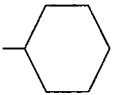 | $CH_3$ | O | O | O | 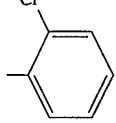 | |
| 90 | 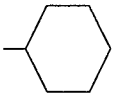 | $CH_3$ | O | O | O | 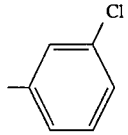 | |
| 91 |  | $CH_3$ | O | O | O | 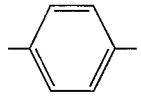 | |
| 92 | 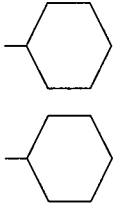 | $CH_3$ | O | O | O | 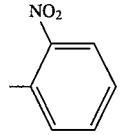 | |
| 93 | 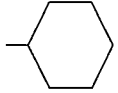 | $CH_3$ | O | O | O | 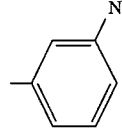 | |

TABLE 1-continued $$R^1-Z^1-\overset{Z^2}{\overset{\|}{C}}-NH-\underset{\underset{R^9}{\overset{|}{CH}}\overset{|}{\underset{CH_3}{|}}}{CH}-\overset{O}{\overset{\|}{C}}-NH-\underset{\underset{CH_3}{|}}{CH}-CH_2Z^3-A$$

| Compound No. | R¹ | R⁹ | Z¹ | Z² | Z³ | A | Melting Point (°C.) or Reflective Index ($n_D^{20}$) |
|---|---|---|---|---|---|---|---|
| 94 | cyclohexyl | CH₃ | O | O | O | 4-NO₂-phenyl | |
| 95 | cyclohexyl | CH₃ | O | O | O | 2-CN-phenyl | |
| 96 | cyclohexyl | CH₃ | O | O | O | 3-CN-phenyl | |
| 97 | cyclohexyl | CH₃ | O | O | O | 4-CN-phenyl | 158–162 |
| 98 | phenyl | CH₃ | O | O | O | phenyl | 123–126 |
| 99 | phenyl | CH₃ | O | O | O | 2-Cl-phenyl | |
| 100 | phenyl | CH₃ | O | O | O | 3-Cl-phenyl | |
| 101 | phenyl | CH₃ | O | O | O | 4-Cl-phenyl | 165–170 |
| 102 | phenyl | CH₃ | O | O | O | 2-NO₂-phenyl | |
| 103 | phenyl | CH₃ | O | O | O | 3-NO₂-phenyl | |
| 104 | phenyl | CH₃ | O | O | O | 4-NO₂-phenyl | 166–169 |

TABLE 1-continued
$$R^1-Z^1-\overset{Z^2}{\overset{\|}{C}}-NH-\underset{\underset{\underset{R^9}{|}}{\overset{|}{CH}}}{CH}-\overset{O}{\overset{\|}{C}}-NH-\underset{\underset{CH_3}{|}}{CH}-CH_2Z^3-A$$
| Compound No. | R[1] | R[9] | Z[1] | Z[2] | Z[3] | A | Melting Point (°C.) or Refractive Index ($n_D^{20}$) |
|---|---|---|---|---|---|---|---|
| 105 |  | CH₃ | O | O | O | 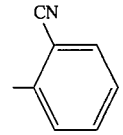 | |
| 106 | 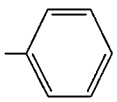 | CH₃ | O | O | O | 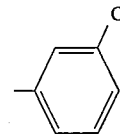 | |
| 107 | 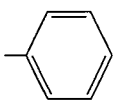 | CH₃ | O | O | O | 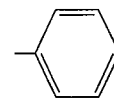 | 142–146 |
| 108 |  | CH₃ | O | O | O | 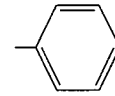 | 158–162 |
| 109 | 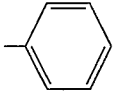 | CH₃ | O | O | O | 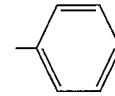 | 128–133 |
| 110 | 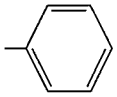 | CH₃ | O | O | O | 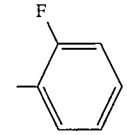 | |
| 111 | 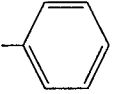 | CH₃ | O | O | O | 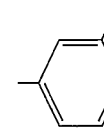 | |
| 112 | 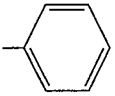 | CH₃ | O | O | O | 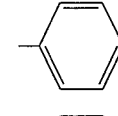 | 137–142 |
| 113 | 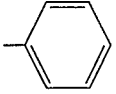 | CH₃ | O | O | O | 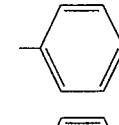 | |
| 114 | 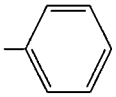 | CH₃ | O | O | O | 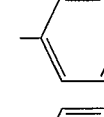 | 151–155 |
| 115 | 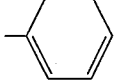 | CH₃ | O | O | O | 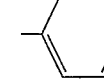 | 144–147 |

TABLE 1-continued
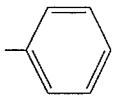
| Compound No. | R¹ | R⁹ | Z¹ | Z² | Z³ | A | Melting Point (°C.) or Refractive Index ($n_D^{20}$) |
|---|---|---|---|---|---|---|---|
| 116 | 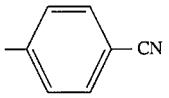 | CH₃ | O | O | O |  | 145–147 |
| 117 | 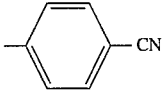 | CH₃ | O | O | O | 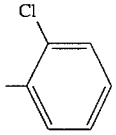 | 166–170 |
| 118 | 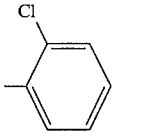 | CH₃ | O | O | O | 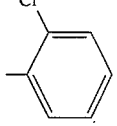 | |
| 119 | 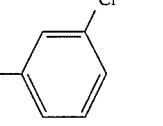 | CH₃ | O | O | O | 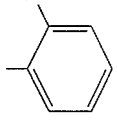 | |
| 120 | 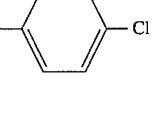 | CH₃ | O | O | O | 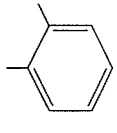 | |
| 121 | 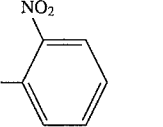 | CH₃ | O | O | O | 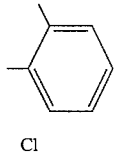 | |
| 122 | 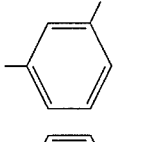 | CH₃ | O | O | O | 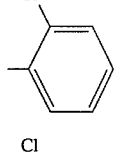 | |
| 123 | 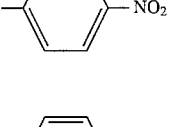 | CH₃ | O | O | O | 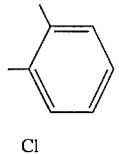 | |
| 124 | 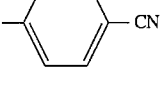 | CH₃ | O | O | O | 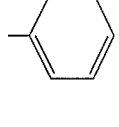 | 137–142 |
| 125 | | CH₃ | O | O | O | 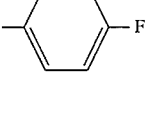 | |

TABLE 1-continued $$R^1-Z^1-\overset{Z^2}{\underset{\|}{C}}-NH-\underset{\underset{R^9}{|}}{\overset{}{CH}}\overset{}{\underset{CH_3}{|}}-\overset{O}{\underset{\|}{C}}-NH-\underset{\underset{CH_3}{|}}{CH}-CH_2Z^3-A$$

| Compound No. | $R^1$ | $R^9$ | $Z^1$ | $Z^2$ | $Z^3$ | A | Melting Point (°C.) or Refractive Index ($n_D^{20}$) |
|---|---|---|---|---|---|---|---|
| 126 | 2-Cl-phenyl | CH₃ | O | O | O | 4-Br-phenyl | |
| 127 | 3-Cl-phenyl | CH₃ | O | O | O | 4-Cl-phenyl | |
| 128 | 3-Cl-phenyl | CH₃ | O | O | O | 4-NO₂-phenyl | |
| 129 | 3-Cl-phenyl | CH₃ | O | O | O | 4-CN-phenyl | 114–117 |
| 130 | 3-Cl-phenyl | CH₃ | O | O | O | 4-F-phenyl | |
| 131 | 3-Cl-phenyl | CH₃ | O | O | O | 4-Br-phenyl | |
| 132 | 3-Cl-phenyl | CH₃ | O | O | O | 4-CF₃-phenyl | |
| 133 | 4-Cl-phenyl | CH₃ | O | O | O | 4-Cl-phenyl | |
| 134 | 4-Cl-phenyl | CH₃ | O | O | O | 4-NO₂-phenyl | 133–138 |
| 135 | 4-Cl-phenyl | CH₃ | O | O | O | 4-CN-phenyl | 156–160 |

TABLE 1-continued $$R^1-Z^1-\overset{\overset{Z^2}{\|}}{C}-NH-\underset{\underset{\underset{R^9}{|}}{\overset{|}{CH}}}{\overset{|}{CH}}-\overset{\overset{O}{\|}}{C}-NH-\underset{\underset{CH_3}{|}}{\overset{|}{CH}}-CH_2Z^3-A$$

| Compound No. | R¹ | R⁹ | Z¹ | Z² | Z³ | A | Melting Point (°C.) or Refractive Index ($n_D^{20}$) |
|---|---|---|---|---|---|---|---|
| 136 | 4-Cl-C₆H₄- | CH₃ | O | O | O | 4-F-C₆H₄- | |
| 137 | 4-Cl-C₆H₄- | CH₃ | O | O | O | 4-Br-C₆H₄- | |
| 138 | C₆H₅- | CH₃ | O | O | O | 4-(CH₃O-CO)-C₆H₄- | |
| 139 | C₆H₅- | CH₃ | O | O | O | 4-(C₂H₅O-CO)-C₆H₄- | |
| 140 | C₆H₅- | CH₃ | O | O | O | 4-(CH₃-SO₂)-C₆H₄- | |
| 141 | C₆H₅- | CH₃ | O | O | O | 4-(CH₃-SO)-C₆H₄- | |
| 142 | C₆H₅- | CH₃ | O | O | O | 4-(CH₃-S)-C₆H₄- | |
| 143 | C₆H₅- | CH₃ | O | O | O | 4-(CF₃-S)-C₆H₄- | |
| 144 | C₆H₅- | CH₃ | O | O | O | 4-(CH₃)₂N-C₆H₄- | |
| 145 | C₆H₅- | CH₃ | O | O | O | 4-(C₆H₅-SO₂)-C₆H₄- | |
| 146 | C₆H₅- | CH₃ | O | O | O | 4-(CH₃-CO)-C₆H₄- | |
| 147 | C₆H₅- | CH₃ | O | O | O | 4-(C₆H₅-CO)-C₆H₄- | |

TABLE 1-continued $$R^1-Z^1-\overset{\overset{Z^2}{\|}}{C}-NH-\underset{\underset{\underset{R^9}{|}}{\overset{|}{CH}}}{CH}-\overset{\overset{O}{\|}}{C}-NH-\underset{\underset{CH_3}{|}}{CH}-CH_2Z^3-A$$

| Compound No. | R[1] | R[9] | Z[1] | Z[2] | Z[3] | A | Melting Point (°C.) or Refractive Index ($n_D^{20}$) |
|---|---|---|---|---|---|---|---|
| 148 |  | CH$_3$ | O | O | O | 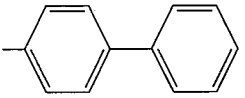 | |
| 149 |  | CH$_3$ | O | O | O | 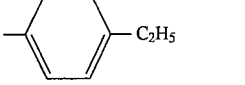 –C$_2$H$_5$ | |
| 150 |  | CH$_3$ | O | O | O | 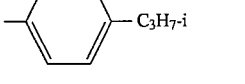 –C$_3$H$_7$-i | |
| 151 |  | CH$_3$ | O | O | O | 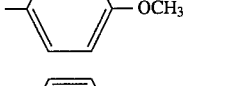 –OCH$_3$ | |
| 152 | 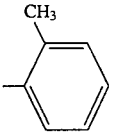 CH$_3$ | CH$_3$ | O | O | O | 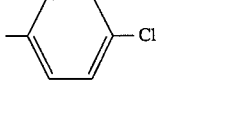 –Cl | |
| 153 | 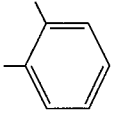 CH$_3$ | CH$_3$ | O | O | O | 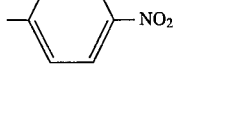 –NO$_2$ | |
| 154 | 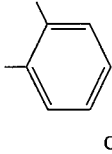 CH$_3$ | CH$_3$ | O | O | O | 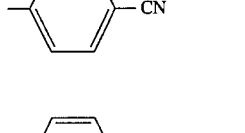 –CN | 146–150 |
| 155 | 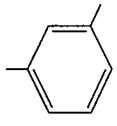 CH$_3$ | CH$_3$ | O | O | O | 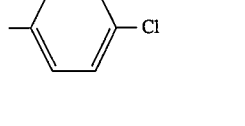 –Cl | |
| 156 | 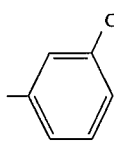 CH$_3$ | CH$_3$ | O | O | O | 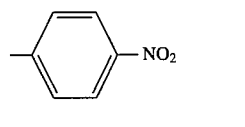 –NO$_2$ | |
| 157 | 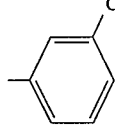 CH$_3$ | CH$_3$ | O | O | O | 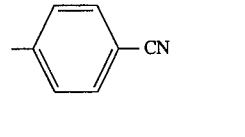 –CN | 97–100 |
| 158 | 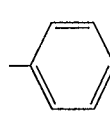 CH$_3$ | CH$_3$ | O | O | O | 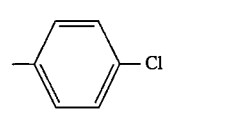 –Cl | |

TABLE 1-continued
$$R^1-Z^1-\underset{\underset{\underset{CH_3}{CH}}{|}}{\overset{\overset{Z^2}{\|}}{C}}-NH-CH-\overset{\overset{O}{\|}}{C}-NH-\underset{\underset{CH_3}{|}}{CH}-CH_2Z^3-A$$
| Compound No. | R¹ | R⁹ | Z¹ | Z² | Z³ | A | Melting Point (°C.) or Refractive Index ($n_D^{20}$) |
|---|---|---|---|---|---|---|---|
| 159 | 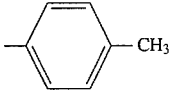 | CH₃ | O | O | O |  | |
| 160 | 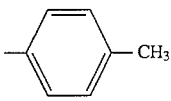 | CH₃ | O | O | O | 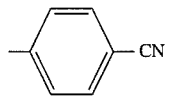 | 152–155 |
| 161 | 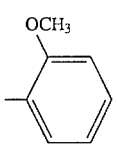 | CH₃ | O | O | O |  | |
| 162 | 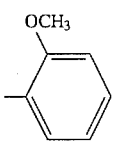 | CH₃ | O | O | O | 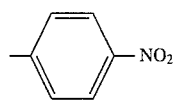 | |
| 163 | 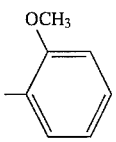 | CH₃ | O | O | O |  | 137–140 |
| 164 | 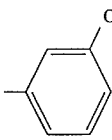 | CH₃ | O | O | O |  | |
| 165 | 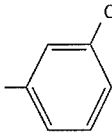 | CH₃ | O | O | O |  | |
| 166 | 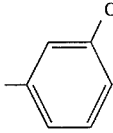 | CH₃ | O | O | O |  | 134–137 |
| 167 | 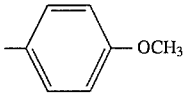 | CH₃ | O | O | O |  | |
| 168 | 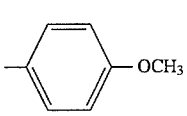 | CH₃ | O | O | O | 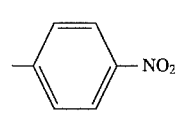 | |

TABLE 1-continued $$R^1-Z^1-\overset{\overset{Z^2}{\|}}{C}-NH-CH-\overset{\overset{O}{\|}}{C}-NH-CH-CH_2Z^3-A$$
$$\underset{R^9}{\overset{|}{CH}}-CH_3 \qquad \underset{CH_3}{|}$$

| Compound No. | R¹ | R⁹ | Z¹ | Z² | Z³ | A | Melting Point (°C.) or Refractive Index ($n_D^{20}$) |
|---|---|---|---|---|---|---|---|
| 169 | 4-OCH₃-C₆H₄ | CH₃ | O | O | O | 4-CN-C₆H₄ | 139–145 |
| 170 | 2,4-Cl₂-C₆H₃ | CH₃ | O | O | O | 4-Cl-C₆H₄ | |
| 171 | 2,4-Cl₂-C₆H₃ | CH₃ | O | O | O | 4-NO₂-C₆H₄ | |
| 172 | 2,4-Cl₂-C₆H₃ | CH₃ | O | O | O | 4-CN-C₆H₄ | |
| 173 | 3,4-(OCH₃)₂-C₆H₃ | CH₃ | O | O | O | 4-Cl-C₆H₄ | |
| 174 | 3,4-(OCH₃)₂-C₆H₃ | CH₃ | O | O | O | 4-NO₂-C₆H₄ | |
| 175 | 3,4-(OCH₃)₂-C₆H₃ | CH₃ | O | O | O | 4-CN-C₆H₄ | |
| 176 | 3-pyridyl | CH₃ | O | O | O | 4-Cl-C₆H₄ | |
| 177 | 3-pyridyl | CH₃ | O | O | O | 4-NO₂-C₆H₄ | |
| 178 | 3-pyridyl | CH₃ | O | O | O | 4-CN-C₆H₄ | |

TABLE 1-continued $$R^1-Z^1-\overset{\overset{Z^2}{\|}}{C}-NH-\underset{\underset{\underset{R^9}{|}}{CH}}{\overset{|}{CH}}-\overset{\overset{O}{\|}}{C}-NH-\underset{\underset{CH_3}{|}}{CH}-CH_2Z^3-A$$

| Compound No. | $R^1$ | $R^9$ | $Z^1$ | $Z^2$ | $Z^3$ | A | Melting Point (°C.) or Refractive Index ($n_D^{20}$) |
|---|---|---|---|---|---|---|---|
| 179 | 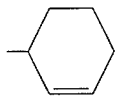 | CH₃ | O | O | O | 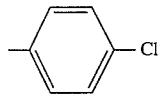—Cl | |
| 180 | 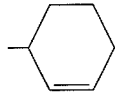 | CH₃ | O | O | O | 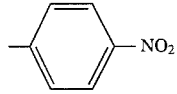—NO₂ | |
| 181 | 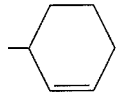 | CH₃ | O | O | O | —CN | |
| 182 | 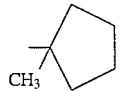 | CH₃ | O | O | O | 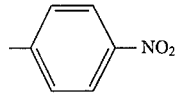—NO₂ | |
| 183 | 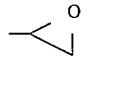 | CH₃ | O | O | O | 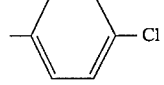—Cl | |
| 184 | CH₂CH₂Cl | CH₃ | O | O | O | 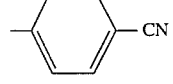—CN | 170–175 |
| 185 | CH₂Cl | CH₃ | O | O | O | 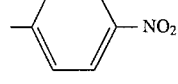—NO₂ | |
| 186 | CH(Cl)CH₃ | CH₃ | O | O | O | 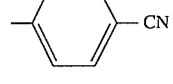—CN | |
| 187 | CH₂CF₃ | CH₃ | O | O | O | 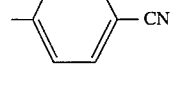—CN | |
| 188 | CH₂—C≡CH | CH₃ | O | O | O | 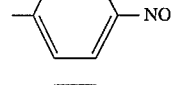—NO₂ | |
| 189 | CH₂CH₂OCH₃ | CH₃ | O | O | O | 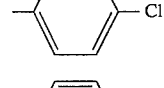—Cl | |
| 190 | CH₂CH₂OCH₃ | CH₃ | O | O | O | 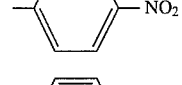—NO₂ | |
| 191 | CH₂CH₂OCH₃ | CH₃ | O | O | O | 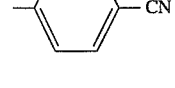—CN | |

TABLE 1-continued $$R^1-Z^1-\overset{\overset{Z^2}{\|}}{C}-NH-\underset{\underset{\underset{R^9}{|}}{\overset{|}{CH}}}{\overset{|}{CH}}-\overset{\overset{O}{\|}}{C}-NH-\underset{\underset{CH_3}{|}}{\overset{|}{CH}}-CH_2Z^3-A$$

| Compound No. | R¹ | R⁹ | Z¹ | Z² | Z³ | A | Melting Point (°C.) or Refractive Index ($n_D^{20}$) |
|---|---|---|---|---|---|---|---|
| 192 | —CH₂—C₆H₅ | CH₃ | O | O | O | —C₆H₄—NO₂ (para) | |
| 193 | —CH₂—C₆H₅ | CH₃ | O | O | O | —C₆H₄—CN (para) | 125–128 |
| 194 | —CH₂—C₆H₄—CH₃ | CH₃ | O | O | O | —C₆H₄—Cl (para) | |
| 195 | —CH₂—C₆H₄—CH₃ | CH₃ | O | O | O | —C₆H₄—CN (para) | 98–101 |
| 196 | —CH₂—C₆H₄—NO₂ | CH₃ | O | O | O | —C₆H₄—Cl (para) | |
| 197 | C₄H₉-t | CH₃ | O | O | O | —C₆H₄—CH₂Cl (para) | |
| 198 | C₄H₉-t | CH₃ | O | O | O | —C₆H₄—OCHF₂ (para) | |
| 199 | C₃H₇-i | CH₃ | O | O | O | —C₆H₄—CH₂Cl (para) | |
| 200 | C₃H₇-i | CH₃ | O | O | O | —C₆H₄—OCHF₂ (para) | |
| 201 | —C₆H₅ | CH₃ | O | O | O | —C₆H₄—CH₂Cl (para) | |
| 202 | —C₆H₅ | CH₃ | O | O | O | —C₆H₄—OCHF₂ (para) | |
| 203 | —C₆H₅ | CH₃ | S | O | O | —C₆H₄—Cl (para) | 111–113 |

TABLE 1-continued $$R^1-Z^1-\overset{\overset{Z^2}{\|}}{C}-NH-\underset{\underset{\underset{CH_3}{|}}{\overset{|}{CH}}}{\overset{|}{CH}}-\overset{\overset{O}{\|}}{C}-NH-\underset{\underset{CH_3}{|}}{\overset{|}{CH}}-CH_2Z^3-A$$

| Compound No. | R¹ | R⁹ | Z¹ | Z² | Z³ | A | Melting Point (°C.) or Refractive Index ($n_D^{20}$) |
|---|---|---|---|---|---|---|---|
| 204 | 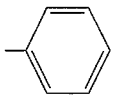 | CH₃ | S | O | O | 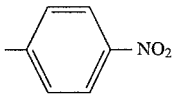—NO₂ | 149–152 |
| 205 | 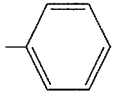 | CH₃ | S | O | O | 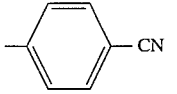—CN | 146–149 |
| 206 | 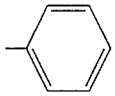 | CH₃ | O | S | O | 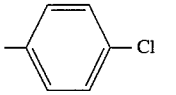—Cl | |
| 207 | 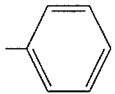 | CH₃ | O | S | O | 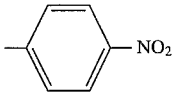—NO₂ | |
| 208 | 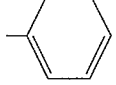 | CH₃ | O | S | O | 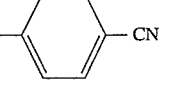—CN | not determined |
| 209 | 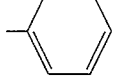 | CH₃ | S | S | O | 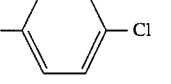—Cl | |
| 210 | 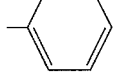 | CH₃ | S | S | O | 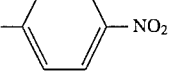—NO₂ | |
| 211 | 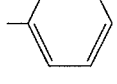 | CH₃ | S | S | O | 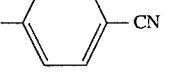—CN | not determined |
| 212 | 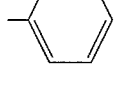 | CH₃ | O | O | S | 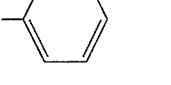 | 140–144 |
| 213 | 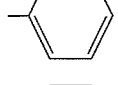 | CH₃ | O | O | S | 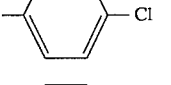—Cl | 136–140 |
| 214 | 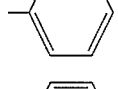 | CH₃ | O | O | S | 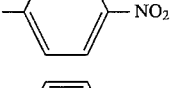—NO₂ | 123–126 |
| 215 | 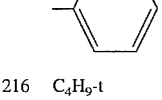 | CH₃ | O | O | S | 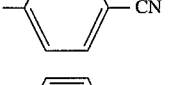—CN | 144–146 |
| 216 | C₄H₉-t | CH₃ | O | O | S | 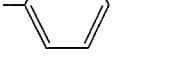 | 74–78 |

TABLE 1-continued $$R^1-Z^1-\underset{\underset{Z^2}{\|}}{C}-NH-\underset{\underset{\underset{R^9}{|}}{\overset{|}{CH}}}{CH}-\underset{\underset{O}{\|}}{C}-NH-\underset{\underset{CH_3}{|}}{CH}-CH_2Z^3-A$$

| Compound No. | R¹ | R⁹ | Z¹ | Z² | Z³ | A | Melting Point (°C.) or Refractive Index ($n_D^{20}$) |
|---|---|---|---|---|---|---|---|
| 217 | C₄H₉-t | CH₃ | O | O | S | 4-NO₂-C₆H₄ | 109–112 |
| 218 | C₄H₉-t | CH₃ | O | O | S | 4-CN-C₆H₄ | |
| 219 | C₃H₇-i | CH₃ | O | O | S | C₆H₅ | 122–126 |
| 220 | C₃H₇-i | CH₃ | O | O | S | 4-CN-C₆H₄ | 165–169 |
| 221 | C₃H₇-i | CH₃ | O | O | NH | 4-Cl-C₆H₄ | 158–160 |
| 222 | C₄H₉-t | CH₃ | O | O | NCH₃ | 4-NO₂-C₆H₄ | |
| 223 | C₆H₅ | CH₃ | O | O | NCOCH₃ | 4-CN-C₆H₄ | |
| 224 | C₆H₅ | CH₃ | O | O | NCO-C₆H₅ | 4-Cl-C₆H₄ | |
| 225 | C₆H₅ | CH₃ | O | O | NCO₂CH₃ | 4-CN-C₆H₄ | |
| 226 | C₄H₉-t | C₂H₅ | O | O | O | 4-Cl-C₆H₄ | 101–104 |
| 227 | C₄H₉-t | C₂H₅ | O | O | O | 4-NO₂-C₆H₄ | 128–130 |
| 228 | C₄H₉-t | C₂H₅ | O | O | O | 4-CN-C₆H₄ | 100–106 |

TABLE 1-continued $$R^1-Z^1-\overset{\overset{Z^2}{\|}}{C}-NH-\underset{\underset{\underset{R^9}{|}}{\overset{|}{CH}}}{\overset{|}{CH}}-\overset{\overset{O}{\|}}{C}-NH-\underset{\underset{CH_3}{|}}{\overset{|}{CH}}-CH_2Z^3-A$$

| Compound No. | R¹ | R⁹ | Z¹ | Z² | Z³ | A | Melting Point (°C.) or Refractive Index ($n_D^{20}$) |
|---|---|---|---|---|---|---|---|
| 229 | $C_4H_9$-t | $C_2H_5$ | O | O | O | 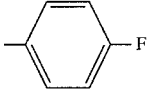 4-F | |
| 230 | 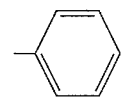 | $C_2H_5$ | O | O | O | 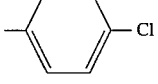 4-Cl | 149–154 |
| 231 | 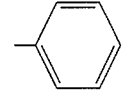 | $C_2H_5$ | O | O | O | 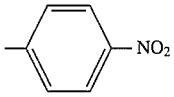 4-NO₂ | 152–154 |
| 232 | 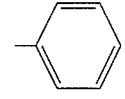 | $C_2H_5$ | O | O | O | 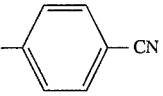 4-CN | 108–112 |
| 233 | $C_4H_9$-t | H | O | O | O | 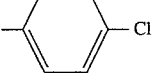 4-Cl | 1.5081 |
| 234 | $C_4H_9$-t | H | O | O | O | 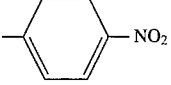 4-NO₂ | |
| 235 | $C_4H_9$-t | H | O | O | O | 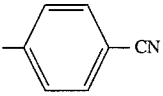 4-CN | not determined |
| 236 | 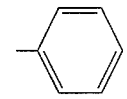 | H | O | O | O | 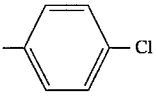 4-Cl | 125–130 |
| 237 | 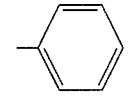 | H | O | O | O | 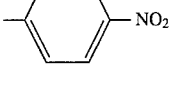 4-NO₂ | |
| 238 | 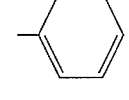 | H | O | O | O | 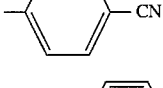 4-CN | 43–46 |
| 239 | $C_4H_9$-t | $CH_3$ | O | O | O | —CH₂—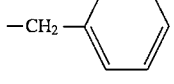 | |
| 240 | $C_4H_9$-t | $CH_3$ | O | O | O | —CH₂—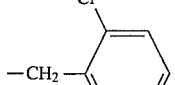 2-Cl | |

TABLE 1-continued $$R^1-Z^1-\overset{Z^2}{\overset{\|}{C}}-NH-\underset{\underset{\underset{CH_3}{|}}{\overset{|}{CH}}}{\overset{|}{CH}}-\overset{O}{\overset{\|}{C}}-NH-\underset{\underset{CH_3}{|}}{CH}-CH_2Z^3-A$$

| Compound No. | $R^1$ | $R^9$ | $Z^1$ | $Z^2$ | $Z^3$ | A | Melting Point (°C.) or Refractive Index ($n_D^{20}$) |
|---|---|---|---|---|---|---|---|
| 241 | $C_4H_9$-t | $CH_3$ | O | O | O | $-CH_2-\phenyl(3-Cl)$ | |
| 242 | $C_4H_9$-t | $CH_3$ | O | O | O | $-CH_2-\phenyl(4-Cl)$ | |
| 243 | $C_4H_9$-t | $CH_3$ | O | O | O | $-CH_2-\phenyl(4-CH_3)$ | |
| 244 | $C_4H_9$-t | $CH_3$ | O | O | O | $-CH_2-\phenyl(4-NO_2)$ | |
| 245 | $C_4H_9$-t | $CH_3$ | O | O | O | $-CH_2-\phenyl(4-CN)$ | |
| 246 | $C_3H_7$-i | $CH_3$ | O | O | O | $-CH_2-\phenyl(4-Cl)$ | 104–109 |
| 247 | $C_3H_7$-i | $CH_3$ | O | O | O | $-CH_2-\phenyl(4-NO_2)$ | |
| 248 | $C_3H_7$-i | $CH_3$ | O | O | O | $-CH_2-\phenyl(4-CN)$ | |
| 249 | phenyl | $CH_3$ | O | O | O | $-CH_2-\phenyl(4-Cl)$ | |
| 250 | phenyl | $CH_3$ | O | O | O | $-CH_2-\phenyl(4-NO_2)$ | |
| 251 | phenyl | $CH_3$ | O | O | O | $-CH_2-\phenyl(4-CN)$ | |
| 252 | phenyl | $CH_3$ | O | O | O | $-CH_2-\phenyl(2,4-Cl_2)$ | |

TABLE 1-continued $$R^1-Z^1-\overset{\overset{Z^2}{\|}}{C}-NH-\underset{\underset{\underset{R^9}{|}}{\overset{|}{CH}}}{CH}-\overset{\overset{O}{\|}}{C}-NH-\underset{\underset{CH_3}{|}}{CH}-CH_2Z^3-A$$

| Compound No. | R¹ | R⁹ | Z¹ | Z² | Z³ | A | Melting Point (°C.) or Refractive Index ($n_D^{20}$) |
|---|---|---|---|---|---|---|---|
| 253 | 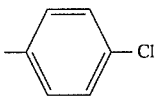 -Cl | CH₃ | O | O | O | -CH₂-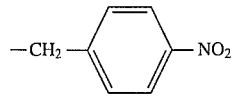-NO₂ | |
| 254 | C₃H₇-i | CH₃ | O | O | O | 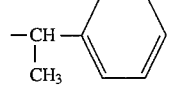 | |
| 255 | C₃H₇-i | CH₃ | O | O | O | 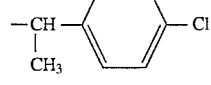-Cl | |
| 256 | 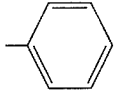 | CH₃ | O | O | O | 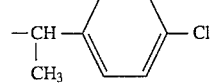-Cl | |
| 257 | C₃H₇-i | CH₃ | O | O | O | 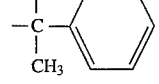 | |
| 258 | C₃H₇-i | CH₃ | O | O | O | 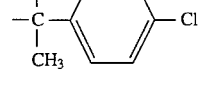-Cl | |
| 259 | 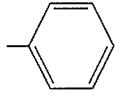 | CH₃ | O | O | O | 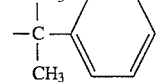 | |
| 260 | C₄H₉-t | CH₃ | O | O | NH | 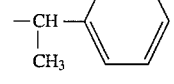 | |
| 261 | C₄H₉-t | CH₃ | O | O | NH | 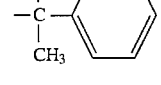 | |
| 262 | C₃H₇-i | CH₃ | O | O | NH | 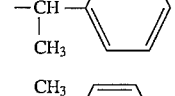 | |
| 263 | C₃H₇-i | CH₃ | O | O | NH | 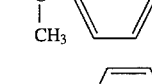 | |
| 264 | 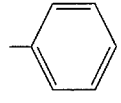 | CH₃ | O | O | NH | 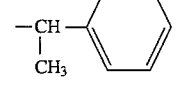 | |

TABLE 1-continued $$R^1-Z^1-\overset{Z^2}{\overset{\|}{C}}-NH-CH-\overset{O}{\overset{\|}{C}}-NH-CH-CH_2Z^3-A$$
with CH(R^9)CH_3 on the middle CH and CH_3 on the right CH

| Compound No. | R¹ | R⁹ | Z¹ | Z² | Z³ | A | Melting Point (°C.) or Refractive Index ($n_D^{20}$) |
|---|---|---|---|---|---|---|---|
| 265 | phenyl | CH₃ | O | O | NH | -C(CH₃)₂-phenyl | |
| 266 | C₄H₉-t | CH₃ | O | O | O | 3-pyridyl | |
| 267 | C₄H₉-t | CH₃ | O | O | O | 2-Cl-3-pyridyl | |
| 268 | C₃H₇-i | CH₃ | O | O | O | 3-pyridyl | |
| 269 | C₃H₇-i | CH₃ | O | O | O | 2-Cl-3-pyridyl | |
| 270 | C₃H₇-i | CH₃ | O | O | O | 5-Cl-3-pyridyl | |
| 271 | phenyl | CH₃ | O | O | O | 3-pyridyl | |
| 272 | phenyl | CH₃ | O | O | O | 2-Cl-3-pyridyl | |
| 273 | phenyl | CH₃ | O | O | O | 5-Cl-3-pyridyl | |
| 274 | phenyl | CH₃ | O | O | O | 2-NO₂-3-pyridyl | |

TABLE 1-continued $$R^1-Z^1-\overset{Z^2}{\underset{\|}{C}}-NH-\underset{\underset{R^9}{|}}{CH}-\overset{O}{\underset{\|}{C}}-NH-\underset{\underset{CH_3}{|}}{CH}-CH_2Z^3-A$$

$$\underset{R^9}{\overset{|}{CH}}\underset{CH_3}{}$$

| Compound No. | $R^1$ | $R^9$ | $Z^1$ | $Z^2$ | $Z^3$ | A | Melting Point (°C.) or Refractive Index ($n_D^{20}$) |
|---|---|---|---|---|---|---|---|
| 275 | 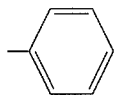 | $CH_3$ | O | O | O | 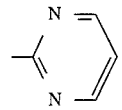 | 60–65 |
| 276 | $C_4H_9$-t | $CH_3$ | O | O | O | 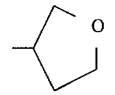 | |
| 277 | $C_3H_7$-i | $CH_3$ | O | O | O | 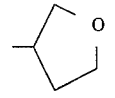 | |
| 278 | 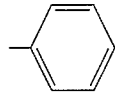 | $CH_3$ | O | O | O | 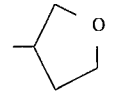 | |
| 279 | $C_4H_9$-t | $CH_3$ | O | O | O | 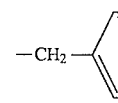 | |
| 280 | $C_4H_9$-t | $CH_3$ | O | O | O | 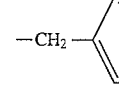 | |
| 281 | $C_3H_7$-i | $CH_3$ | O | O | O | 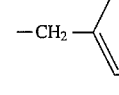 | |
| 282 | $C_3H_7$-i | $CH_3$ | O | O | O | 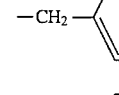 | |
| 283 | 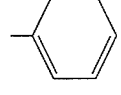 | $CH_3$ | O | O | O | 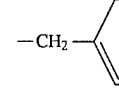 | |
| 284 | 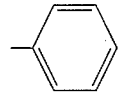 | $CH_3$ | O | O | O | 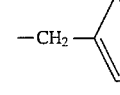 | |
| 285 | $C_3H_7$-i | $CH_3$ | O | O | O | 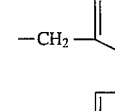 | |
| 286 | $C_3H_7$-i | $CH_3$ | O | O | S | 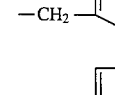 | |
| 287 | 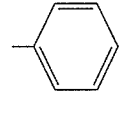 | $CH_3$ | O | O | O | 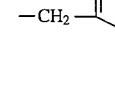 | |

TABLE 1-continued $$R^1-Z^1-\overset{\overset{Z^2}{\|}}{C}-NH-\underset{\underset{\underset{R^9}{|}}{CH}}{\overset{|}{CH}}-\overset{\overset{O}{\|}}{C}-NH-\underset{\underset{CH_3}{|}}{CH}-CH_2Z^3-A$$

| Compound No. | $R^1$ | $R^9$ | $Z^1$ | $Z^2$ | $Z^3$ | A | Melting Point (°C.) or Reflactive Index ($n_D^{20}$) |
|---|---|---|---|---|---|---|---|
| 288 |  | $CH_3$ | O | O | S | 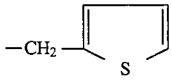 | |
| 289 |  | $CH_3$ | O | O | NH | 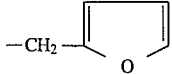 | |
| 290 | $C_3H_7$-i | $CH_3$ | O | O | NH | 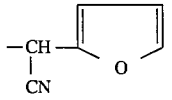 | |
| 291 | $C_3H_7$-i | $CH_3$ | O | O | NH | 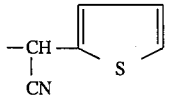 | |
| 292 |  | $CH_3$ | O | O | NH | 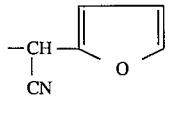 | |
| 293 |  | $CH_3$ | O | O | NH | 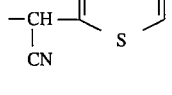 | |
| 294 | $C_3H_7$-i | $CH_3$ | O | O | O | 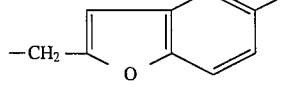 | |
| 295 | $C_3H_7$-i | $CH_3$ | O | O | O | 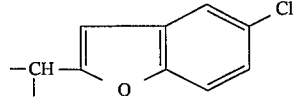 | |
| 296 | $C_3H_7$-i | $CH_3$ | O | O | O | 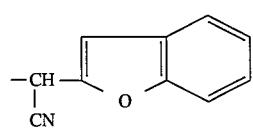 | |
| 297 | $C_3H_7$-i | $CH_3$ | O | O | NH | 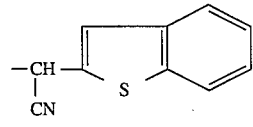 | |
| 298 |  | $CH_3$ | O | O | O | 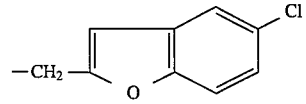 | |

TABLE 1-continued $$R^1-Z^1-\overset{\overset{Z^2}{\|}}{C}-NH-CH-\overset{\overset{O}{\|}}{C}-NH-CH-CH_2Z^3-A$$
with CH(R⁹)CH₃ on the middle CH and CH₃ on the right CH

| Compound No. | R¹ | R⁹ | Z¹ | Z² | Z³ | A | Melting Point (°C.) or Refractive Index ($n_D^{20}$) |
|---|---|---|---|---|---|---|---|
| 299 |  | CH₃ | O | O | O | 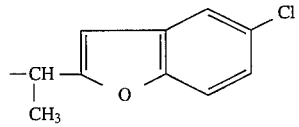 5-Cl benzofuran, –CH(CH₃)– | |
| 300 | 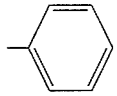 | CH₃ | O | O | O | 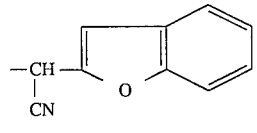 benzofuran, –CH(CH₃)– | |
| 301 | 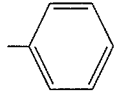 | CH₃ | O | O | NH | 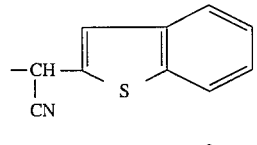 benzothiophene, –CH(CN)– | |
| 302 | 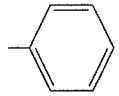 | CH₃ | O | O | NH | 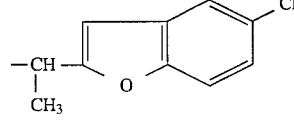 5-Cl benzofuran, –CH(CH₃)– | |
| 303 | 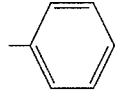 | CH₃ | O | O | NH | 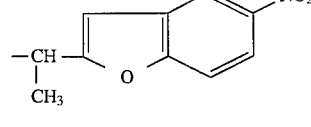 5-NO₂ benzofuran, –CH(CH₃)– | |
| 304 | C₃H₇-i | CH₃ | O | O | NH | 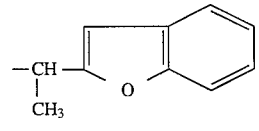 benzofuran, –CH(CH₃)– | |
| 305 | C₃H₇-i | CH₃ | O | O | NH | 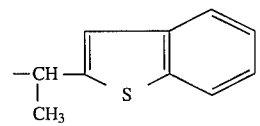 benzothiophene, –CH(CH₃)– | |
| 306 | C₃H₇-i | CH₃ | O | O | NH | 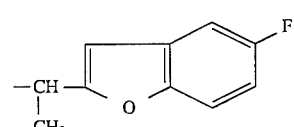 5-F benzofuran, –CH(CH₃)– | |
| 307 | C₃H₇-i | CH₃ | O | O | NH | 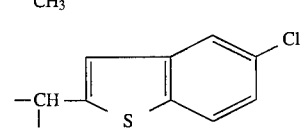 5-Cl benzothiophene, –CH(CH₃)– | |
| 308 | C₃H₇-i | CH₃ | O | O | NH | 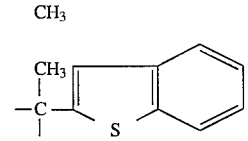 benzothiophene, –C(CH₃)₂– | |

TABLE 1-continued $$R^1-Z^1-\overset{\overset{Z^2}{\|}}{C}-NH-\underset{\underset{\underset{CH_3}{|}}{\overset{|}{CH}}}{\overset{|}{CH}}-\overset{\overset{O}{\|}}{C}-NH-\underset{\underset{CH_3}{|}}{CH}-CH_2Z^3-A$$

| Compound No. | $R^1$ | $R^9$ | $Z^1$ | $Z^2$ | $Z^3$ | A | Melting Point (°C.) or Refractive Index ($n_D^{20}$) |
|---|---|---|---|---|---|---|---|
| 309 | $C_3H_7$-i | $CH_3$ | O | O | O | 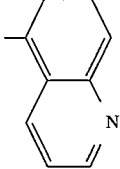 | |
| 310 | $C_3H_7$-i | $CH_3$ | O | O | O | 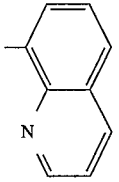 | |
| 311 | 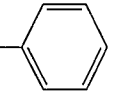 | $CH_3$ | O | O | $NCH_2OCH_3$ | 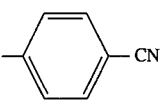 | |
| 312 | 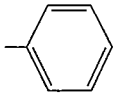 | $CH_3$ | O | O | SO | 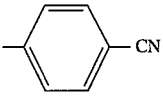 | |
| 313 | 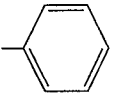 | $CH_3$ | O | O | $SO_2$ | 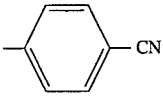 | |
| 314 | 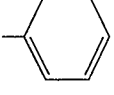 | $CH_3$ | O | O | NH | 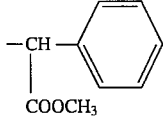 | |
| 315 | $C_3H_7$-i | $CH_3$ | O | O | NH | 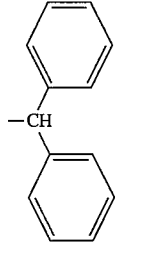 | |
| 316 | $C_3H_7$-i | $CH_3$ | O | O | O | 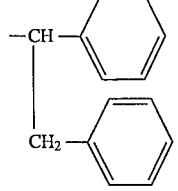 | |
| 317 |  | $CH_3$ | O | O | O | 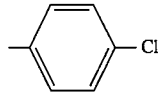 | |

TABLE 1-continued $$R^1-Z^1-\underset{\underset{}{\overset{Z^2}{\|}}}{C}-NH-\underset{\underset{\underset{R^9}{|}}{\overset{|}{CH}}\underset{CH_3}{\diagdown}}{CH}-\overset{O}{\overset{\|}{C}}-NH-\underset{\underset{CH_3}{|}}{CH}-CH_2Z^3-A$$

| Compound No. | $R^1$ | $R^9$ | $Z^1$ | $Z^2$ | $Z^3$ | A | Melting Point (°C.) or Refractive Index ($n_D^{20}$) |
|---|---|---|---|---|---|---|---|
| 318 | -CH₂-C₆H₄-CN | CH₃ | O | O | O | -C₆H₄-CN | |
| 319 | -C₆H₄-CN | CH₃ | O | O | O | -C₆H₄-Cl | |
| 320 | -C₆H₄-CN | CH₃ | O | O | O | -C₆H₄-NO₂ | |
| 321 | -C₆H₄-CN | CH₃ | O | O | O | -C₆H₄-CN | |
| 322 | -C₆H₄-CF₃ | CH₃ | O | O | O | -C₆H₄-NO₂ | |
| 323 | -C₆H₄-CF₃ | CH₃ | O | O | O | -C₆H₄-CN | 115–117 |
| 324 | -C₆H₄-OCF₃ | CH₃ | O | O | O | -C₆H₄-Cl | |
| 325 | -C₆H₄-OCF₃ | CH₃ | O | O | O | -C₆H₄-NO₂ | |
| 326 | -C₆H₄-OCF₃ | CH₃ | O | O | O | -C₆H₄-CN | 127–129 |
| 327 | C₄H₉-t | CH₃ | O | O | O | -C₆H₄-S-CH₃ | 93–96 |
| 328 | C₄H₉-t | CH₃ | O | O | O | -C₆H₄-S(O)-CH₃ | 48–51 |
| 329 | C₄H₉-t | CH₃ | O | O | O | -C₆H₄-S(O)₂-CH₃ | 122–125 |

TABLE 1-continued $$R^1-Z^1-\overset{\overset{Z^2}{\|}}{C}-NH-\underset{\underset{\underset{CH_3}{|}}{\overset{|}{CH}}}{CH}-\overset{\overset{O}{\|}}{C}-NH-\underset{\underset{CH_3}{|}}{CH}-CH_2Z^3-A$$

| Compound No. | R¹ | R⁹ | Z¹ | Z² | Z³ | A | Melting Point (°C.) or Reflactive Index ($n_D^{20}$) |
|---|---|---|---|---|---|---|---|
| 330 | $C_4H_9$-t | $CH_3$ | O | O | S | 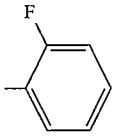 2-F-phenyl | 74–77 |
| 331 | $C_4H_9$-t | $CH_3$ | O | O | S | 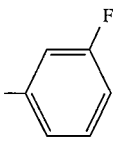 3-F-phenyl | 1.5164 |
| 332 | $C_4H_9$-t | $CH_3$ | O | O | S | 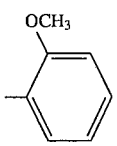 2-OCH₃-phenyl | 1.5319 |
| 333 | $C_4H_9$-t | $CH_3$ | O | O | S | 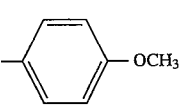 4-OCH₃-phenyl | 1.5361 |
| 334 | $C_4H_9$-t | $CH_3$ | O | O | NH | 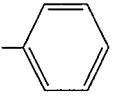 phenyl | 102–104 |
| 335 | $C_4H_9$-t | $CH_3$ | O | O | S | 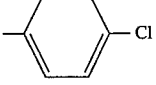 4-Cl-phenyl | 80–84 |
| 336 | $C_4H_9$-t | $CH_3$ | O | O | S |  4-Cl-phenyl | 133–137 |
| 337 | $C_4H_9$-t | $CH_3$ | O | O | S | 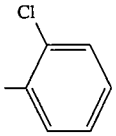 2-Cl-phenyl | 1.5360 |
| 338 | $C_4H_9$-t | $CH_3$ | O | O | S | 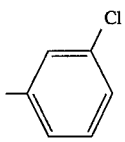 3-Cl-phenyl | 1.5361 |
| 339 | $C_4H_9$-t | $CH_3$ | O | O | S | 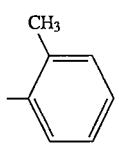 2-CH₃-phenyl | 1.5274 |

TABLE 1-continued $$R^1-Z^1-\overset{\overset{Z^2}{\|}}{C}-NH-\underset{\underset{\underset{R^9}{|}}{\underset{CH}{|}}}{\overset{|}{CH}}-\overset{\overset{O}{\|}}{C}-NH-\underset{\underset{CH_3}{|}}{CH}-CH_2Z^3-A$$

| Compound No. | R¹ | R⁹ | Z¹ | Z² | Z³ | A | Melting Point (°C.) or Reflactive Index ($n_D^{20}$) |
|---|---|---|---|---|---|---|---|
| 340 | $C_4H_9$-t | $CH_3$ | O | O | S | 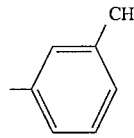 3-CH₃-phenyl | 1.5245 |
| 341 | $C_4H_9$-t | $CH_3$ | O | O | S | 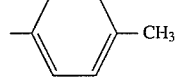 4-CH₃-phenyl | 1.5269 |
| 342 | $C_4H_9$-t | $CH_3$ | O | O | S | 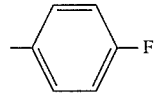 4-F-phenyl | 66–69 |
| 343 | $C_4H_9$-t | $CH_3$ | O | O | O | 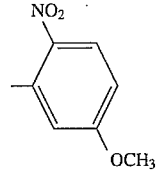 2-NO₂-4-OCH₃-phenyl | 71–74 |
| 344 | $C_4H_9$-t | $CH_3$ | O | O | S | 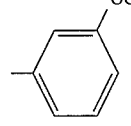 3-OCH₃-phenyl | 1.5312 |
| 345 | $C_3H_7$-i | $CH_3$ | O | O | O |  4-Cl-phenyl | 161–163 |
| 346 | $C_3H_7$-i | $CH_3$ | O | O | O |  4-Cl-phenyl | 167–171 |
| 347 | $C_3H_7$-i | $CH_3$ | O | O | O | 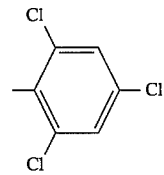 2,4,6-Cl₃-phenyl | 166–172 |
| 348 | $C_3H_7$-i | $CH_3$ | O | O | S | 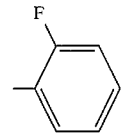 2-F-phenyl | 121–123 |
| 349 | $C_3H_7$-i | $CH_3$ | O | O | S | 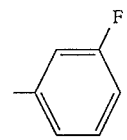 3-F-phenyl | 125–129 |

TABLE 1-continued $$R^1-Z^1-\underset{\|}{C}(Z^2)-NH-\underset{|}{CH}(CH(R^9)CH_3)-\underset{\|}{C}(O)-NH-\underset{|}{CH}(CH_3)-CH_2Z^3-A$$

| Compound No. | R¹ | R⁹ | Z¹ | Z² | Z³ | A | Melting Point (°C.) or Refractive Index ($n_D^{20}$) |
|---|---|---|---|---|---|---|---|
| 350 | $C_3H_7$-i | $CH_3$ | O | O | S | 2-OCH₃-phenyl | 103–106 |
| 351 | $C_3H_7$-i | $CH_3$ | O | O | S | 4-OCH₃-phenyl | 122–125 |
| 352 | $C_3H_7$-i | $CH_3$ | O | O | S | 4-NO₂-phenyl | 155–158 |
| 353 | $C_3H_7$-i | $CH_3$ | O | O | NH | phenyl | 130–134 |
| 354 | $C_3H_7$-i | $CH_3$ | O | O | SO | 4-F-phenyl | 119–123 |
| 355 | $C_3H_7$-i | $CH_3$ | O | O | SO₂ | 4-F-phenyl | 151–153 |
| 356 | $C_3H_7$-i | $CH_3$ | O | O | O | 4-NO₂-phenyl | 177–180 |
| 357 | $C_3H_7$-i | $CH_3$ | O | O | S | 2-CN-phenyl | 137–140 |
| 358 | $C_3H_7$-i | $CH_3$ | O | O | NCH₃ | phenyl | 145–148 |
| 359 | $C_3H_7$-i | $CH_3$ | O | O | NH | 4-F-phenyl | 155–156 |
| 360 | $C_3H_7$-i | $CH_3$ | O | O | NCH₃ | 4-F-phenyl | 141–143 |
| 361 | $C_3H_7$-i | $CH_3$ | O | O | NH | 2-Cl-phenyl | 85–90 |

TABLE 1-continued $$R^1-Z^1-\underset{\underset{}{\|}}{\overset{\overset{Z^2}{\|}}{C}}-NH-\underset{\underset{\underset{R^9}{|}}{CH}}{\underset{|}{CH}}-\overset{\overset{O}{\|}}{C}-NH-\underset{\underset{CH_3}{|}}{CH}-CH_2Z^3-A$$

| Compound No. | $R^1$ | $R^9$ | $Z^1$ | $Z^2$ | $Z^3$ | A | Melting Point (°C.) or Refractive Index ($n_D^{20}$) |
|---|---|---|---|---|---|---|---|
| 362 | $C_3H_7$-i | $CH_3$ | O | O | NH | 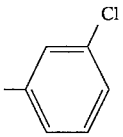 3-Cl phenyl | 143–145 |
| 363 | $C_3H_7$-i | $CH_3$ | O | O | $NCH_3$ | 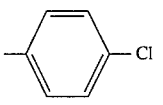 4-Cl phenyl | 65–67 |
| 364 | $C_3H_7$-i | $CH_3$ | O | O | NH | 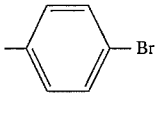 4-Br phenyl | 146–149 |
| 365 | $C_3H_7$-i | $CH_3$ | O | O | S | 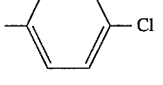 4-Cl phenyl | 115–118 |
| 366 | $C_3H_7$-i | $CH_3$ | O | O | S | 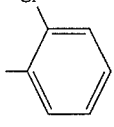 2-Cl phenyl | 124–127 |
| 367 | $C_3H_7$-i | $CH_3$ | O | O | S | 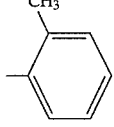 2-CH₃ phenyl | 119–121 |
| 368 | $C_3H_7$-i | $CH_3$ | O | O | S | 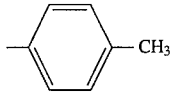 4-CH₃ phenyl | 107–110 |
| 369 | $C_3H_7$-i | $CH_3$ | O | O | S | 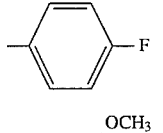 4-F phenyl | 111–115 |
| 370 | $C_3H_7$-i | $CH_3$ | O | O | S | 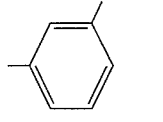 3-OCH₃ phenyl | 109–112 |
| 371 | $C_4H_9$-i | $CH_3$ | O | O | O | 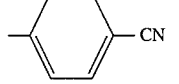 4-CN phenyl | 125–130 |
| 372 | $C_5H_{11}$ | $CH_3$ | O | O | O | 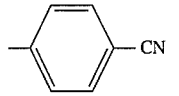 4-CN phenyl | 109–111 |

TABLE 1-continued $$R^1-Z^1-\overset{\overset{Z^2}{\|}}{C}-NH-\underset{\underset{\underset{R^9}{|}}{CH}}{\overset{|}{CH}}-\overset{\overset{O}{\|}}{C}-NH-\underset{\underset{CH_3}{|}}{CH}-CH_2Z^3-A$$

| Compound No. | $R^1$ | $R^9$ | $Z^1$ | $Z^2$ | $Z^3$ | A | Melting Point (°C.) or Reflactive Index ($n_D^{20}$) |
|---|---|---|---|---|---|---|---|
| 373 | $C_6H_{13}$ | $CH_3$ | O | O | O |  —CN | 107–110 |
| 374 | —CH—$C_3H_7$<br>    |<br>    $CH_3$ | $CH_3$ | O | O | O | 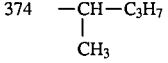 —CN | 122–125 |
| 375 | $C_3H_7$-i | $CH_3$ | O | O | $NCOCH_3$ | 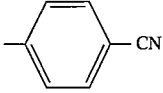 —F | 56–60 |
| 376 | 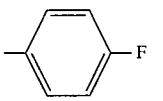 | $CH_3$ | O | O | O | 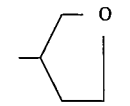 —CN | 181–184 |
| 377 |  | $CH_3$ | O | O | O | 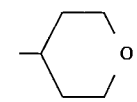 —CN | 201–204 |
| 378 |  | $CH_3$ | O | O | O | 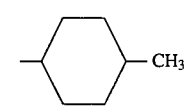 —CN | 111–116 |
| 379 | 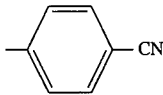 | $CH_3$ | O | O | O | 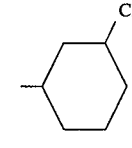 —CN | 141–142 |
| 380 | 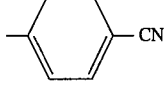 | $CH_3$ | O | O | O | 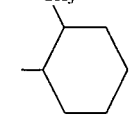 —CN | 133–136 |
| 381 | $CH_2$—C≡CH | $CH_3$ | O | O | O | 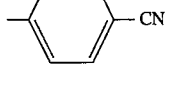 —CN | 148–151 |
| 382 | 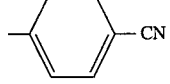 | $CH_3$ | O | O | O | 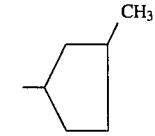 —CN | 161–164 |
| 383 | —CH—$CH_2OCH_3$<br>    |<br>    $CH_3$ | $CH_3$ | O | O | O | 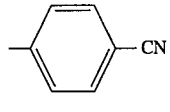 —CN | 102–107 |

TABLE 1-continued
$$R^1-Z^1-\underset{\underset{\|}{Z^2}}{C}-NH-\underset{\underset{\underset{R^9}{|}}{\underset{CH}{|}}{\underset{|}{CH_3}}}{CH}-\underset{\underset{\|}{O}}{C}-NH-\underset{\underset{|}{CH_3}}{CH}-CH_2Z^3-A$$
| Compound No. | R¹ | R⁹ | Z¹ | Z² | Z³ | A | Melting Point (°C.) or Refractive Index ($n_D^{20}$) |
|---|---|---|---|---|---|---|---|
| 384 |  | CH₃ | O | O | O | 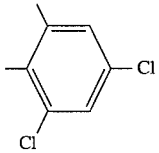 | 159–162 |
| 385 |  | CH₃ | O | O | NH | 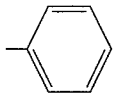 | 130–134 |
| 386 | 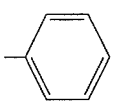 | CH₃ | O | O | S |  | 127–130 |
| 387 | 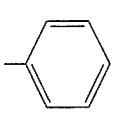 | CH₃ | O | O | S | 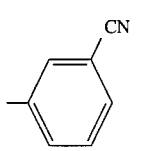 | 108–110 |
| 388 | 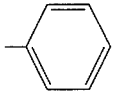 | CH₃ | O | O | NH | 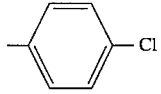 | 154–156 |
| 389 | 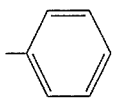 | CH₃ | O | O | NCH₃ | 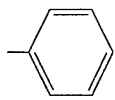 | 125–130 |
| 390 | 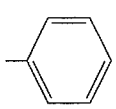 | CH₃ | O | O | NH | 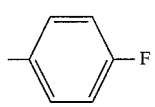 | 147–149 |
| 391 | 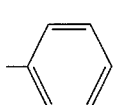 | CH₃ | O | O | NCH₃ | 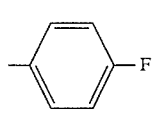 | 64–70 |
| 392 | 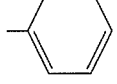 | CH₃ | O | O | NH | 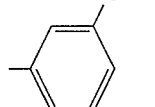 | 117–119 |
| 393 | 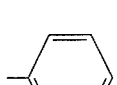 | CH₃ | O | O | NH | 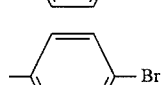 | 156–160 |
| 394 | 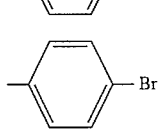 | CH₃ | O | O | O | 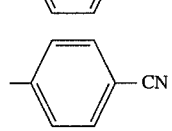 | 156–162 |

TABLE 1-continued $$R^1-Z^1-\overset{\overset{Z^2}{\|}}{C}-NH-\underset{\underset{\underset{R^9}{|}}{\overset{|}{CH}}}{\overset{|}{CH}}-\overset{\overset{O}{\|}}{C}-NH-\underset{\underset{CH_3}{|}}{\overset{|}{CH}}-CH_2Z^3-A$$

| Compound No. | R¹ | R⁹ | Z¹ | Z² | Z³ | A | Melting Point (°C.) or Refractive Index ($n_D^{20}$) |
|---|---|---|---|---|---|---|---|
| 395 | 4-Cl-C₆H₄- | CH₃ | O | O | O | 4-CN-C₆H₄- | 137–140 |
| 396 | 4-Cl-C₆H₄- | CH₃ | O | O | O | 4-CN-C₆H₄- | 174–179 |
| 397 | 4-F-C₆H₄- | CH₃ | O | O | O | 4-CN-C₆H₄- | 153–156 |
| 398 | 4-NO₂-C₆H₄- | CH₃ | O | O | O | 4-CN-C₆H₄- | 130–134 |
| 399 | 4-F-C₆H₄- | CH₃ | O | O | O | 4-NO₂-C₆H₄- | 156–161 |
| 400 | 2-NO₂-C₆H₄- | CH₃ | O | O | O | 4-CN-C₆H₄- | 125–129 |
| 401 | 4-F-C₆H₄- | CH₃ | O | O | O | 4-CN-C₆H₄- | 155–158 |
| 402 | 2,3-(CH₃)₂-C₆H₃- | CH₃ | O | O | O | 4-CN-C₆H₄- | 141–144 |
| 403 | 3,4-(CH₃)₂-C₆H₃- | CH₃ | O | O | O | 4-CN-C₆H₄- | 153–154 |
| 404 | 2,4-F₂-C₆H₃- | CH₃ | O | O | O | 4-CN-C₆H₄- | 144–148 |
| 405 | 3,4-F₂-C₆H₃- | CH₃ | O | O | O | 4-CN-C₆H₄- | 129–133 |

TABLE 1-continued $$R^1-Z^1-\underset{\underset{}{\overset{Z^2}{\|}}}{C}-NH-\underset{\underset{\underset{R^9}{|}}{\overset{|}{CH}}}{CH}-\underset{\underset{}{\overset{O}{\|}}}{C}-NH-\underset{\underset{CH_3}{|}}{CH}-CH_2Z^3-A$$
$$\phantom{R^1-Z^1-C-NH-CH-C-NH-CH-CH}\underset{CH_3}{|}$$

| Compound No. | R¹ | R⁹ | Z¹ | Z² | Z³ | A | Melting Point (°C.) or Refractive Index ($n_D^{20}$) |
|---|---|---|---|---|---|---|---|
| 406 | 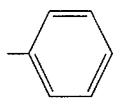 | CH₃ | O | O | NH | 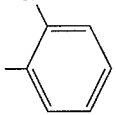 | 60–62 |
| 407 | C₄H₉-t | CH₃ | O | O | O | 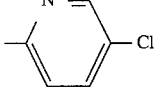 | 90–93 |
| 408 | 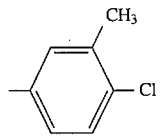 | CH₃ | O | O | O | 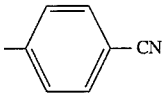 | 129–130 |
| 409 | C₄H₉-t | CH₃ | O | O | O | 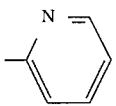 | 111–112 |
| 410 | C₄H₉-t | CH₃ | O | O | O | 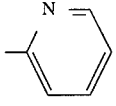 | 129–131 |
| 411 | 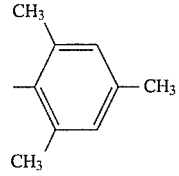 | CH₃ | O | O | O |  | 163–164 |
| 412 | C₃H₇-i | CH₃ | O | O | O | 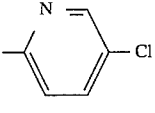 | 118–120 |
| 413 | 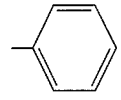 | CH₃ | O | O | O | 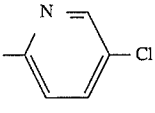 | 123–124 |
| 414 | C₄H₉-t | C₂H₅ | O | O | O | 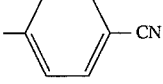 | 122–125 |
| 415 | C₄H₉-t | C₂H₅ | O | O | O | 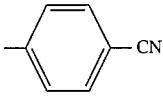 | 135–137 |
| 416 | C₃H₇-i | C₂H₅ | O | O | S | 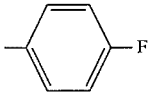 | 85–86 |

TABLE 1-continued $$R^1-Z^1-\overset{\overset{Z^2}{\|}}{C}-NH-\underset{\underset{\underset{R^9}{|}}{CH}}{\overset{|}{CH}}-\overset{\overset{O}{\|}}{C}-NH-\underset{\underset{CH_3}{|}}{CH}-CH_2Z^3-A$$

| Compound No. | $R^1$ | $R^9$ | $Z^1$ | $Z^2$ | $Z^3$ | A | Melting Point (°C.) or Reflactive Index ($n_D^{20}$) |
|---|---|---|---|---|---|---|---|
| 417 | $C_3H_7$-i | $C_2H_5$ | O | O | O | 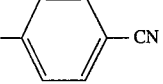 | 145–148 |
| 418 | 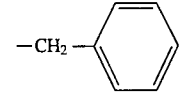 | $C_2H_5$ | O | O | O | 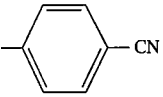 | 139–141 |
| 419 | 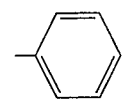 | $C_2H_5$ | O | O | S | 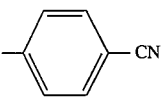 | 105–107 |
| 420 | 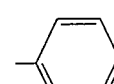 | $C_2H_5$ | O | O | S | 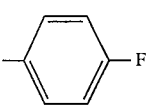 | 130–133 |
| 421 | 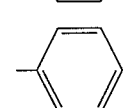 | $C_2H_5$ | O | O | NH | 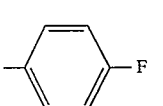 | 137–139 |
| 422 | 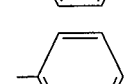 | $C_2H_5$ | O | O | $NCH_3$ | 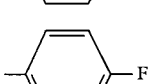 | 53–56 |
| 423 | 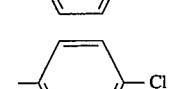 | $C_2H_5$ | O | O | O | 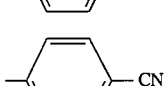 | 159–163 |
| 424 | 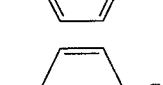 | $C_2H_5$ | O | O | O | 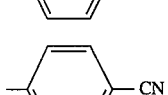 | 150–153 |
| 425 | $C_3H_7$-i | H | O | O | O | 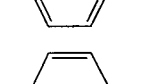 | 118–121 |
| 426 | 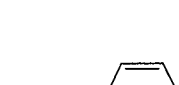 | H | O | O | O |  | 127–132 |
| 427 | 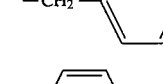 | H | O | O | O | 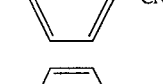 | 141–145 |
| 428 | $C_3H_7$-i | $CH_3$ | O | O | O | 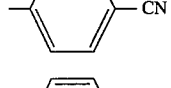 | 217–220 |
| 429 |  | $CH_3$ | O | O | O | 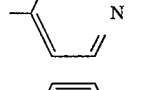 | 65–68 |

TABLE 1-continued $$R^1-Z^1-\overset{\overset{Z^2}{\|}}{C}-NH-\underset{\underset{\underset{R^9}{|}}{CH}}{\overset{|}{CH}}-\overset{\overset{O}{\|}}{C}-NH-\underset{\underset{CH_3}{|}}{CH}-CH_2Z^3-A$$

| Compound No. | $R^1$ | $R^9$ | $Z^1$ | $Z^2$ | $Z^3$ | A | Melting Point (°C.) or Refractive Index ($n_D^{20}$) |
|---|---|---|---|---|---|---|---|
| 430 | $C_3H_7$-i | $CH_3$ | S | O | O | 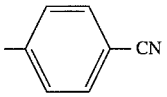 —CN | 161–163 |
| 431 | $C_2H_5$ | $CH_3$ | S | O | O | 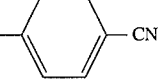 —CN | 152–154 |
| 432 | $C_2H_5$ | $CH_3$ | S | O | O | 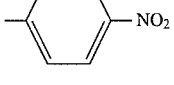 —$NO_2$ | 164–166 |
| 433 | 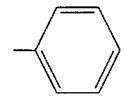 | $CH_3$ | O | O | O | 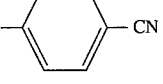 —CN | 118–120 |
| 434 | 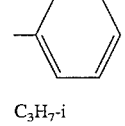 | $CH_3$ | O | O | $NCOCH_3$ | 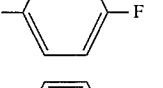 —F | |
| 435 | $C_3H_7$-i | $CH_3$ | O | O | $NCO_2CH_3$ | 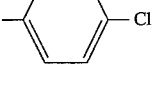 —Cl | |
| 436 | $C_3H_7$-i | $CH_3$ | O | O | NCO—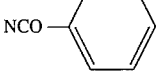 | 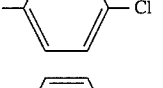 —Cl | 71–73 |
| 437 | $C_3H_7$-i | $CH_3$ | O | O | $NCH_2OCH_3$ | 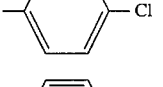 —Cl | |
| 438 | 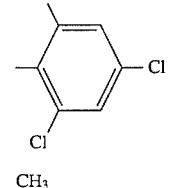 | $CH_3$ | O | O | O | 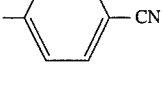 —CN | |
| 439 | 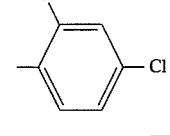 | $CH_3$ | O | O | O | 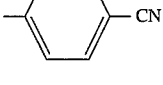 —CN | 135–138 |
| 440 | —$CH_2CH_2$— | $CH_3$ | O | O | O | 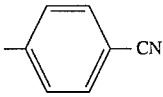 —CN | 112–114 |

TABLE 1-continued $$R^1-Z^1-\overset{\overset{Z^2}{\|}}{C}-NH-\underset{\underset{\underset{R^9}{|}}{\overset{|}{CH}}}{CH}-\overset{\overset{O}{\|}}{C}-NH-\underset{\underset{CH_3}{|}}{CH}-CH_2Z^3-A$$

| Compound No. | $R^1$ | $R^9$ | $Z^1$ | $Z^2$ | $Z^3$ | A | Melting Point (°C.) or Reflactive Index ($n_D^{20}$) |
|---|---|---|---|---|---|---|---|
| 441 | $C_3H_7$-i | $CH_3$ | O | O | NH | ―⟨ ⟩―CN | |

TABLE 2

$$R^1-Z^1-\overset{\overset{Z^2}{\|}}{C}-NH-\underset{\underset{\underset{R^9}{|}}{\overset{|}{CH}}}{CH}-\overset{\overset{O}{\|}}{C}-NH-\underset{\underset{CH_3}{|}}{CH}-CH_2-CH_2-Z^3-A$$

| Compound No. | $R^1$ | $R^9$ | $Z^1$ | $Z^2$ | $Z^3$ | A | Melting Point (°C.) or Reflactive Index ($n_D^{20}$) |
|---|---|---|---|---|---|---|---|
| 442 | ―⟨ ⟩ | $CH_3$ | O | O | O | ―⟨ ⟩―Cl | |
| 443 | $C_4H_9$-t | $CH_3$ | O | O | O | ―⟨ ⟩―Cl | |
| 444 | $C_3H_7$-i | $CH_3$ | O | O | O | ―⟨ ⟩―Cl | |
| 445 | ―$CH_2$―⟨ ⟩―$CH_3$ | $CH_3$ | O | O | O | ―⟨ ⟩(OCH$_3$)(OCH$_3$) | |
| 446 | ―$CH_2$―⟨ ⟩ | $CH_3$ | O | O | O | ―⟨ ⟩(OCH$_3$)(OCH$_3$) | |
| 447 | $C_3H_7$-i | $CH_3$ | O | O | O | ―⟨ ⟩(OCH$_3$)(OCH$_3$) | |
| 448 | ―⟨ ⟩ | $CH_3$ | O | O | O | ―⟨ ⟩―CN | |
| 449 | $C_4H_9$-t | $CH_3$ | O | O | O | ―⟨ ⟩―CN | |

TABLE 2-continued

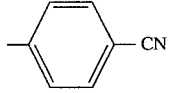

| Compound No. | R$^1$ | R$^9$ | Z$^1$ | Z$^2$ | Z$^3$ | A | Melting Point (°C.) or Reflactive Index (n$_D^{20}$) |
|---|---|---|---|---|---|---|---|
| 450 | C$_3$H$_7$-i | CH$_3$ | O | O | O | ![p-cyanophenyl] -C$_6$H$_4$-CN | |

TABLE 3

$$R^1-O-\overset{O}{\underset{\|}{C}}-NH-\underset{R^2}{\underset{|}{CH}}-\overset{O}{\underset{\|}{C}}-NH-\underset{CH_3}{\underset{|}{CH}}-CH_2-O-Q$$

| Compound No. | R$^1$ | R$^2$ | Q | Melting Point (°C.) or Reflactive Index (n$_D^{20}$) |
|---|---|---|---|---|
| 451 | -C$_6$H$_4$-OCHF$_2$ | C$_3$H$_7$ | -C$_6$H$_4$-CN | 117–119 |
| 452 | C$_4$H$_9$-t | C$_3$H$_7$ | -C$_6$H$_4$-CN | 78–80 |
| 453 | C$_4$H$_9$-t | C$_3$H$_7$ | -C$_6$H$_4$-CN | 105–107 |
| 454 | C$_4$H$_9$-t | C$_3$H$_7$ | -C$_6$H$_4$-CN | 93–95 |
| 455 | C$_4$H$_9$-t | C$_4$H$_9$-i | -C$_6$H$_4$-CN | not determined |
| 456 | C$_4$H$_9$-t | cyclopentyl | -C$_6$H$_4$-CN | 140–142 |
| 457 | C$_4$H$_9$-t | C$_4$H$_9$-t | -C$_6$H$_4$-CN | 68–71 |
| 458 | C$_4$H$_9$-t | -C$_6$H$_5$ | -C$_6$H$_4$-CN | 61–64 |
| 459 | C$_4$H$_9$-t | -C$_6$H$_4$-Cl | -C$_6$H$_4$-CN | 124–126 |

TABLE 3-continued $$R^1-O-\overset{\overset{O}{\|}}{C}-NH-\underset{\underset{R^2}{|}}{CH}-\overset{\overset{O}{\|}}{C}-NH-\underset{\underset{CH_3}{|}}{CH}-CH_2-O-Q$$

| Compound No. | R[1] | R[2] | Q | Melting Point (°C.) or Refractive Index ($n_D^{20}$) |
|---|---|---|---|---|
| 460 | $C_4H_9$-t | $-\underset{\underset{CH_3}{\|}}{C}=CH_2$ | —C₆H₄—CN (p) | 1.5132 |
| 461 | $C_4H_9$-t | $-\underset{\underset{CH_3}{\|}}{C}=CH_2$ | —C₆H₄—CN (p) | 107–109 |
| 462 | $C_3H_7$-i | cyclopentyl | —C₆H₄—CN (p) | 155–158 |
| 463 | $C_3H_7$-i | phenyl | —C₆H₄—CN (p) | 149–151 |
| 464 | $C_3H_7$-i | —C₆H₄—Cl (p) | —C₆H₄—CN (p) | 158–161 |
| 465 | phenyl | $C_3H_7$ | —C₆H₄—CN (p) | 88–91 |
| 466 | phenyl | $C_4H_9$-i | —C₆H₄—CN (p) | 43–47 |
| 467 | phenyl | cyclopentyl | —C₆H₄—CN (p) | 153–156 |
| 468 | phenyl | $C_4H_9$-t | —C₆H₄—CN (p) | 75–78 |
| 469 | phenyl | phenyl | —C₆H₄—CN (p) | 68–71 |
| 470 | phenyl | —C₆H₄—Cl (p) | —C₆H₄—CN (p) | 152–155 |
| 471 | —C₆H₄—Cl (p) | cyclopentyl | —C₆H₄—CN (p) | 141–145 |
| 472 | —CH₂—C₆H₅ | cyclopentyl | —C₆H₄—CN (p) | 170–174 |

TABLE 3-continued $$R^1-O-\overset{O}{\overset{\|}{C}}-NH-\overset{R^2}{\overset{|}{CH}}-\overset{O}{\overset{\|}{C}}-NH-\overset{CH_3}{\overset{|}{CH}}-CH_2-O-Q$$

| Compound No. | R¹ | R² | Q | Melting Point (°C.) or Reflactive Index (n$_D^{20}$) |
|---|---|---|---|---|
| 473 | —CH₂—C₆H₅ | C₄H₉-t | —C₆H₄—CN | 46–49 |
| 474 | —CH₂—C₆H₅ | —C₆H₅ | —C₆H₄—CN | 155–157 |
| 475 | —CH₂—C₆H₅ | —C₆H₄—Cl | —C₆H₄—CN | 128–129 |
| 476 | (CH₃)₂C(CN)— | C₃H₇-i | —C₆H₄—CN | 127–129 |
| 477 | 2-Cl-cyclohexyl | C₃H₇-i | —C₆H₄—CN | 152–154 |
| 478 | C₄H₉-t | C₃H₇-i | 2-CF₃-pyridin-5-yl | 100–103 |
| 479 | C₄H₉-t | C₃H₇-i | 3-Cl-2-CF₃-pyridin-5-yl | 105–106 |
| 480 | C₄H₉-t | C₃H₇-i | 5-Cl-6-C₂H₅-pyrazin-3-yl | 109–112 |
| 481 | C₃H₇-i | C₃H₇-i | 5-Cl-6-C₂H₅-pyrazin-3-yl | 173–175 |
| 482 | —CH₂—cyclohexyl | C₃H₇-i | —C₆H₄—CN | 128–129 |

TABLE 4

$$R^1-O-\overset{\overset{O}{\|}}{C}-NH-\underset{\underset{R^2}{|}}{CH}-\overset{\overset{O}{\|}}{C}-NH-\underset{\underset{R^4}{|}}{CH}-Z^3-A$$

| Compound No. | R¹ | R² | R⁴ | Z³ | A | Melting Point (°C.) or Refractive Index ($n_D^{20}$) |
|---|---|---|---|---|---|---|
| 483 | C₄H₉-t | C₃H₇i | CH₃ | $\overset{O}{\underset{C-N}{\|}}\,\overset{H}{\|}$ | 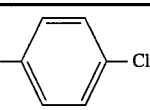 4-Cl-C₆H₄ | 82–87 |
| 484 | C₄H₉-t | C₃H₇-i | CH₃ | $\overset{O}{\underset{C-N}{\|}}\,\overset{H}{\|}$ | 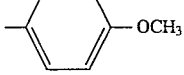 4-OCH₃-C₆H₄ | 156–159 |
| 485 | C₄H₉-t | C₃H₇-i | CH₃ | $\overset{O}{\underset{C-N}{\|}}\,\overset{H}{\|}$ | 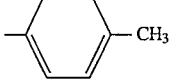 4-CH₃-C₆H₄ | 145–149 |
| 486 | C₄H₉-t | C₃H₇-i | CH₃ | $\overset{O}{\underset{C-N}{\|}}\,\overset{H}{\|}$ | 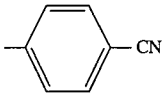 4-CN-C₆H₄ | 96–100 |
| 487 | C₄H₉-t | C₃H₇-i | CH₃ | $\overset{O}{\underset{C-N}{\|}}\,\overset{H}{\|}$ | 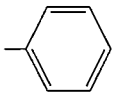 C₆H₅ | 157–158 |
| 488 | C₄H₉-t | C₃H₇-i | CH₃ | $\overset{O}{\underset{C-N}{\|}}\,\overset{H}{\|}$ | 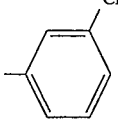 2-Cl-C₆H₄ | 83–86 |
| 489 | C₄H₉-t | C₃H₇-i | CH₃ | $\overset{O}{\underset{C-N}{\|}}\,\overset{H}{\|}$ | —CH₂—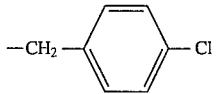 4-Cl-C₆H₄ | 144–146 |
| 490 | C₄H₉-t | C₃H₇-i | CH₃ | $\overset{O}{\underset{C-N}{\|}}\,\overset{CH_3}{\|}$ | 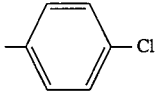 4-Cl-C₆H₄ | 70–73 |
| 491 | C₄H₉-t | C₃H₇-i | CH₃ | $\overset{O}{\underset{C-N}{\|}}\,\overset{H}{\|}$ | 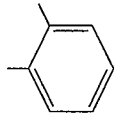 2-Cl-C₆H₄ | 140—143 |
| 492 | C₃H₇-i | C₃H₇-i | CH₃ | $\overset{O}{\underset{C-N}{\|}}\,\overset{H}{\|}$ | 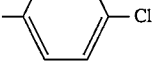 4-Cl-C₆H₄ | 179–182 |
| 493 | C₃H₇-i | C₃H₇-i | CH₃ | $\overset{O}{\underset{C-N}{\|}}\,\overset{H}{\|}$ | 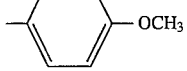 4-OCH₃-C₆H₄ | 251–255 |
| 494 | C₃H₇-i | C₃H₇-i | CH₃ | $\overset{O}{\underset{C-N}{\|}}\,\overset{H}{\|}$ | 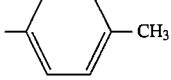 4-CH₃-C₆H₄ | 219—222 |

TABLE 4-continued $$R^1-O-\overset{O}{\underset{||}{C}}-NH-\underset{\underset{R^2}{|}}{CH}-\overset{O}{\underset{||}{C}}-NH-\underset{\underset{R^4}{|}}{CH}-Z^3-A$$

| Compound No. | R¹ | R² | R⁴ | Z³ | A | Melting Point (°C.) or Reflactive Index ($n_D^{20}$) |
|---|---|---|---|---|---|---|
| 495 | $C_3H_7$-i | $C_3H_7$-i | $CH_3$ | $\overset{O}{\underset{||}{C}}-\overset{H}{\underset{|}{N}}$ | 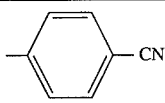 —CN | 88–92 |
| 496 | $C_3H_7$-i | $C_3H_7$-i | $CH_3$ | $\overset{O}{\underset{||}{C}}-\overset{H}{\underset{|}{N}}$ | 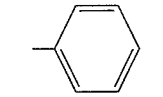 | 211–212 |
| 497 | $C_3H_7$-i | $C_3H_7$-i | $CH_3$ | $\overset{O}{\underset{||}{C}}-\overset{H}{\underset{|}{N}}$ | 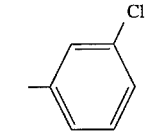 Cl | 210–213 |
| 498 | $C_3H_7$-i | $C_3H_7$-i | $CH_3$ | $\overset{O}{\underset{||}{C}}-\overset{H}{\underset{|}{N}}$ | —CH₂— 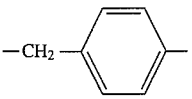 —Cl | 200–203 |
| 499 | $C_3H_7$-i | $C_3H_7$-i | $CH_3$ | $\overset{O}{\underset{||}{C}}-\overset{CH_3}{\underset{|}{N}}$ | 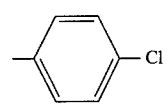 —Cl | 68–72 |
| 500 | $C_3H_7$-i | $C_3H_7$-i | $CH_3$ | $\overset{O}{\underset{||}{C}}-\overset{H}{\underset{|}{N}}$ | 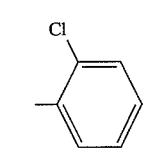 Cl | 205–210 |
| 501 | $C_3H_7$-i | $C_3H_7$-i | $CH_3$ | $\overset{O}{\underset{||}{C}}-\overset{H}{\underset{|}{N}}$ | 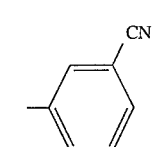 CN | 113–115 |
| 502 | $C_3H_7$-i | $C_3H_7$-i | $CH_3$ | $\overset{O}{\underset{||}{C}}-\overset{H}{\underset{|}{N}}$ | 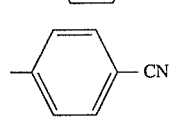 —CN | 184–186 |
| 503 | $C_3H_7$-i | $C_3H_7$-i | $CH_3$ | $\overset{O}{\underset{||}{C}}-\overset{H}{\underset{|}{N}}$ | 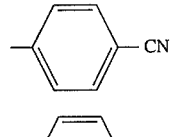 —CN | 73–75 |
| 504 | $C_3H_7$-i | $C_3H_7$-i | $CH_3$ | COO | 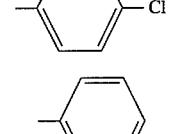 —Cl | 184–185 |
| 505 | $C_3H_7$-i | $C_3H_7$-i | $CH_3$ | COO | 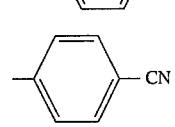 | 151–153 |
| 506 | $C_3H_7$-i | $C_4H_9$-i | $CH_3$ | $\overset{O}{\underset{||}{C}}-\overset{H}{\underset{|}{N}}$ |  —CN | 197–198 |

TABLE 4-continued $$R^1-O-\overset{O}{\underset{\|}{C}}-NH-\underset{\underset{R^2}{|}}{CH}-\overset{O}{\underset{\|}{C}}-NH-\underset{\underset{R^4}{|}}{CH}-Z^3-A$$

| Compound No. | $R^1$ | $R^2$ | $R^4$ | $Z^3$ | A | Melting Point (°C.) or Refractive Index ($n_D^{20}$) |
|---|---|---|---|---|---|---|
| 507 | $C_3H_7$-i | $C_2H_5$ | $CH_3$ | $\underset{C-N}{\overset{O\phantom{X}H}{\underset{\|\phantom{X}\|}{\phantom{X}}}}$ | 4-CN-phenyl | 84–87 |
| 508 | $C_4H_9$-s | $C_3H_7$-i | $CH_3$ | $\underset{C-N}{\overset{O\phantom{X}H}{\underset{\|\phantom{X}\|}{\phantom{X}}}}$ | 4-CN-phenyl | 165–167 |
| 509 | cyclopentyl | $C_3H_7$-i | $CH_3$ | $\underset{C-N}{\overset{O\phantom{X}H}{\underset{\|\phantom{X}\|}{\phantom{X}}}}$ | 4-CN-phenyl | 197–199 |
| 510 | phenyl | $C_3H_7$-i | $CH_3$ | $\underset{C-N}{\overset{O\phantom{X}H}{\underset{\|\phantom{X}\|}{\phantom{X}}}}$ | 4-Cl-phenyl | 201–204 |
| 511 | phenyl | $C_3H_7$-i | $CH_3$ | $\underset{C-N}{\overset{O\phantom{X}H}{\underset{\|\phantom{X}\|}{\phantom{X}}}}$ | 4-$OCH_3$-phenyl | 219–221 |
| 512 | phenyl | $C_3H_7$-i | $CH_3$ | $\underset{C-N}{\overset{O\phantom{X}H}{\underset{\|\phantom{X}\|}{\phantom{X}}}}$ | 4-$CH_3$-phenyl | 245–250 |
| 513 | phenyl | $C_3H_7$-i | $CH_3$ | $\underset{C-N}{\overset{O\phantom{X}H}{\underset{\|\phantom{X}\|}{\phantom{X}}}}$ | 4-CN-phenyl | 225–230 |
| 514 | phenyl | $C_3H_7$-i | $CH_3$ | $\underset{C-N}{\overset{O\phantom{X}H}{\underset{\|\phantom{X}\|}{\phantom{X}}}}$ | phenyl | 199–202 |
| 515 | phenyl | $C_3H_7$-i | $CH_3$ | $\underset{C-N}{\overset{O\phantom{X}H}{\underset{\|\phantom{X}\|}{\phantom{X}}}}$ | 3-Cl-phenyl | 194–197 |
| 516 | phenyl | $C_3H_7$-i | $CH_3$ | $\underset{C-N}{\overset{O\phantom{X}H}{\underset{\|\phantom{X}\|}{\phantom{X}}}}$ | $-CH_2-$(4-Cl-phenyl) | 173–175 |
| 517 | phenyl | $C_3H_7$-i | $CH_3$ | $\underset{C-N}{\overset{O\phantom{X}CH_3}{\underset{\|\phantom{X}\|}{\phantom{X}}}}$ | 4-Cl-phenyl | 69–71 |
| 518 | phenyl | $C_3H_7$-i | $CH_3$ | $\underset{C-N}{\overset{O\phantom{X}H}{\underset{\|\phantom{X}\|}{\phantom{X}}}}$ | 3-CN-phenyl | 149–153 |

TABLE 4-continued $$R^1-O-\overset{O}{\underset{\|}{C}}-NH-\underset{\underset{R^2}{|}}{CH}-\overset{O}{\underset{\|}{C}}-NH-\underset{\underset{R^4}{|}}{CH}-Z^3-A$$

| Compound No. | $R^1$ | $R^2$ | $R^4$ | $Z^3$ | A | Melting Point (°C.) or Reflective Index ($n_D^{20}$) |
|---|---|---|---|---|---|---|
| 519 | 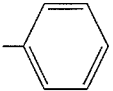 | $C_3H_7$-i | $CH_3$ | $\overset{O}{\underset{\|}{C}}-\overset{H}{\underset{\|}{N}}$ | 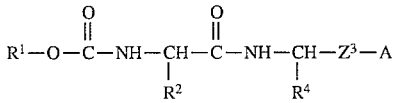—CN | 158–161 |
| 520 | 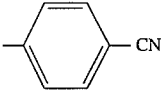 | $C_3H_7$-i | $CH_3$ | $\overset{O}{\underset{\|}{C}}-\overset{H}{\underset{\|}{N}}$ | 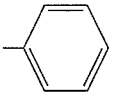—CN | 202–203 |
| 521 | 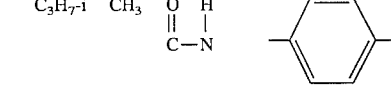 | $C_3H_7$-i | $CH_3$ | COO | 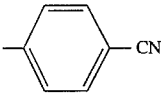—Cl | 168–170 |
| 522 | 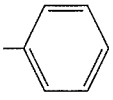 | $C_3H_7$-i | $CH_3$ | COO | 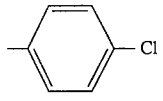 | 175–178 |
| 523 | 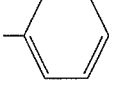 | $C_4H_9$-s | $CH_3$ | $\overset{O}{\underset{\|}{C}}-\overset{H}{\underset{\|}{N}}$ | 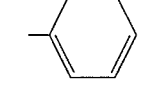—CN | 157–159 |
| 524 | 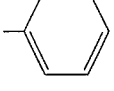 | $C_2H_5$ | $CH_3$ | $\overset{O}{\underset{\|}{C}}-\overset{H}{\underset{\|}{N}}$ | 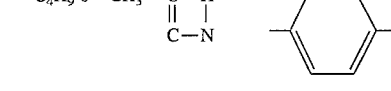—CN | 156–158 |
| 525 | 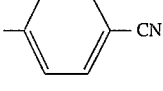—Cl | $C_3H_7$-i | $CH_3$ | $\overset{O}{\underset{\|}{C}}-\overset{H}{\underset{\|}{N}}$ | 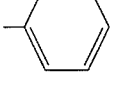—CN | 182–184 |
| 526 | $C_3H_7$-i | $C_3H_7$-i | H | $\overset{O}{\underset{\|}{C}}-\overset{H}{\underset{\|}{N}}$ | 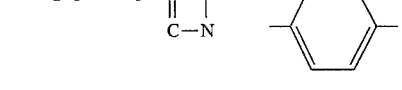—CN | 181–185 |

TABLE 5

$$R^1-Z^1-\overset{Z^2}{\underset{\|}{C}}-NH-\underset{\underset{\underset{CH_3}{\diagup}\underset{CH_3}{\diagdown}}{CH}}{CH}-\overset{O}{\underset{\|}{C}}-NH-CH_2-CH_2-Z^3-A$$

| Compound No. | $R^1$ | $Z^1$ | $Z^2$ | $Z^3$ | A | Melting Point (°C.) or Reflective Index ($n_D^{20}$) |
|---|---|---|---|---|---|---|
| 527 | $C_4H_9$-t | O | O | O | 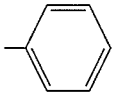 | 158–160 |
| 528 | $C_4H_9$-t | O | O | O | 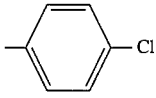—Cl | |

TABLE 5-continued $$R^1-Z^1-\overset{Z^2}{\underset{\|}{C}}-NH-\underset{\underset{H_3C}{\overset{CH}{|}}\underset{CH_3}{}}{CH}-\overset{O}{\underset{\|}{C}}-NH-CH_2-CH_2-Z^3-A$$

| Compound No. | R¹ | Z¹ | Z² | Z³ | A | Melting Point (°C.) or Refractive Index ($n_D^{20}$) |
|---|---|---|---|---|---|---|
| 529 | $C_4H_9$-t | O | O | O | 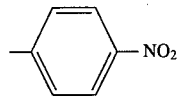 4-NO₂-phenyl | |
| 530 | $C_4H_9$-t | O | O | O | 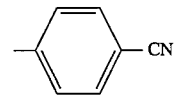 4-CN-phenyl | |
| 531 | $C_4H_9$-t | O | O | O | 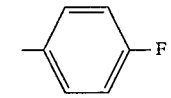 4-F-phenyl | |
| 532 | $C_3H_7$-i | O | O | O | 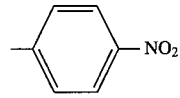 4-NO₂-phenyl | |
| 533 | $C_3H_7$-i | O | O | O | 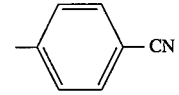 4-CN-phenyl | |
| 534 | $C_3H_7$-i | O | O | O | 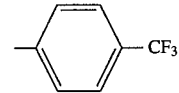 4-CF₃-phenyl | |
| 535 | 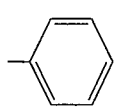 phenyl | O | O | O | 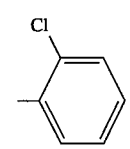 2-Cl-phenyl | |
| 536 | 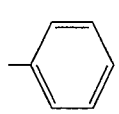 phenyl | O | O | O | 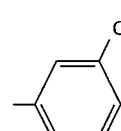 3-Cl-phenyl | |
| 537 | 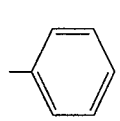 phenyl | O | O | O | 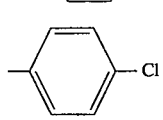 4-Cl-phenyl | |
| 538 | 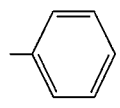 phenyl | O | O | O | 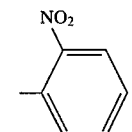 2-NO₂-phenyl | |
| 539 | 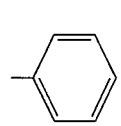 phenyl | O | O | O | 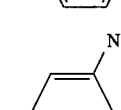 3-NO₂-phenyl | |

TABLE 5-continued
$$R^1-Z^1-\overset{Z^2}{\underset{\|}{C}}-NH-\underset{\underset{\underset{CH_3}{|}}{\overset{\overset{CH_3}{|}}{CH}}}{\overset{|}{CH}}-\overset{O}{\underset{\|}{C}}-NH-CH_2-CH_2-Z^3-A$$
| Compound No. | R¹ | Z¹ | Z² | Z³ | A | Melting Point (°C.) or Refractive Index ($n_D^{20}$) |
|---|---|---|---|---|---|---|
| 540 | 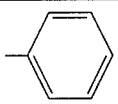 | O | O | O | 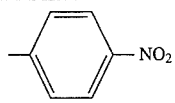—NO₂ | |
| 541 | 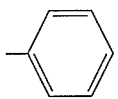 | O | O | O | 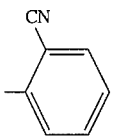 (CN ortho) | |
| 542 | 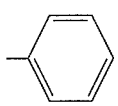 | O | O | O | 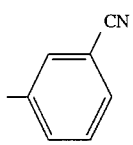 (CN meta) | |
| 543 | 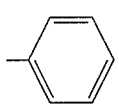 | O | O | O | 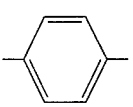—CN | |
| 544 |  | S | O | O | 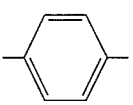—CN | |
| 545 | 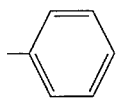 | O | S | O | 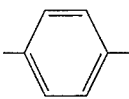—CN | |
| 546 | 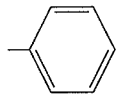 | S | S | O | 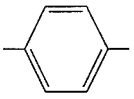—CN | |
| 547 | 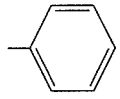 | O | O | S | 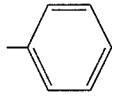 | |
| 548 | 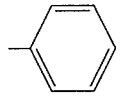 | O | O | S | 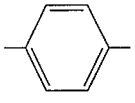—Cl | |
| 549 | 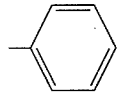 | O | O | S | —NO₂ | |
| 550 | 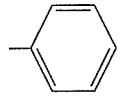 | O | O | S | 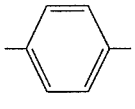—CN | |
| 551 | C₄H₉-t | O | O | S | 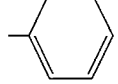 | 75–77 |

TABLE 5-continued $$R^1-Z^1-\overset{\overset{Z^2}{\|}}{C}-NH-\underset{\underset{\underset{CH_3}{|}}{\overset{|}{CH}}}{\overset{|}{CH}}-\overset{\overset{O}{\|}}{C}-NH-CH_2-CH_2-Z^3-A$$

| Compound No. | R¹ | Z¹ | Z² | Z³ | A | Melting Point (°C.) or Reflactive Index ($n_D^{20}$) |
|---|---|---|---|---|---|---|
| 552 | $C_4H_9$-t | O | O | S | 4-$NO_2$-phenyl | |
| 553 | $C_4H_9$-t | O | O | S | 4-CN-phenyl | |
| 554 | 2-Cl-phenyl | O | O | O | 4-Cl-phenyl | |
| 555 | 2-Cl-phenyl | O | O | O | 4-$NO_2$-phenyl | |
| 556 | 2-Cl-phenyl | O | O | O | 4-CN-phenyl | |
| 557 | 3-Cl-phenyl | O | O | O | 4-Cl-phenyl | |
| 558 | 3-Cl-phenyl | O | O | O | 4-$NO_2$-phenyl | |
| 559 | 3-Cl-phenyl | O | O | O | 4-CN-phenyl | |
| 560 | 4-Cl-phenyl | O | O | O | 4-Cl-phenyl | |
| 561 | 4-Cl-phenyl | O | O | O | 4-$NO_2$-phenyl | |
| 562 | 4-Cl-phenyl | O | O | O | 4-CN-phenyl | |

TABLE 5-continued
$$R^1-Z^1-\overset{Z^2}{\underset{\|}{C}}-NH-\underset{\underset{\underset{CH_3\ CH_3}{\|}}{\overset{|}{CH}}}{CH}-\overset{O}{\underset{\|}{C}}-NH-CH_2-CH_2-Z^3-A$$
| Compound No. | R¹ | Z¹ | Z² | Z³ | A | Melting Point (°C.) or Reflactive Index ($n_D^{20}$) |
|---|---|---|---|---|---|---|
| 563 | 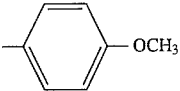 -OCH₃ | O | O | O | 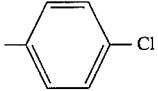 -Cl | |
| 564 | -CH₂-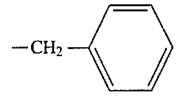 | O | O | O | 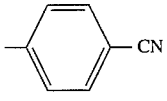 -CN | |
| 565 | -CH₂-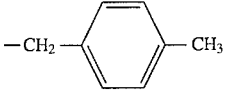-CH₃ | O | O | O | 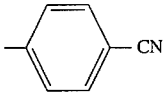 -CN | |
| 566 | -CH₂-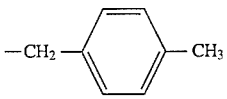-CH₃ | O | O | O | 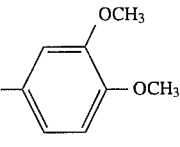 OCH₃, OCH₃ | |
| 567 | 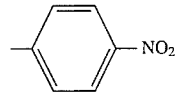-NO₂ | O | O | O | 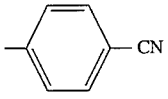 -CN | |
| 568 | C₃H₇-i | O | O | O | 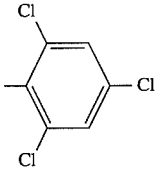 Cl, Cl, Cl | |
| 569 | C₃H₇-i | O | O | O | 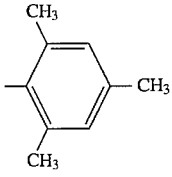 CH₃, CH₃, CH₃ | |
| 570 | 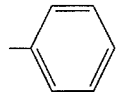 | O | O | O | 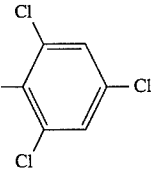 Cl, Cl, Cl | |
| 571 | 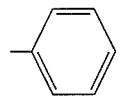 | O | O | O | 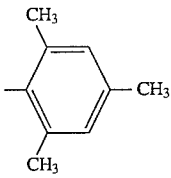 CH₃, CH₃, CH₃ | |
| 572 | C₃H₇-i | O | O | NH | 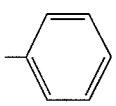 | |

TABLE 5-continued $$R^1-Z^1-\underset{\underset{}{\|}}{C}-NH-\underset{\underset{CH_3\diagup\overset{CH}{\diagdown}CH_3}{|}}{CH}-\underset{\underset{}{\|}}{C}-NH-CH_2-CH_2-Z^3-A$$

| Compound No. | R¹ | Z¹ | Z² | Z³ | A | Melting Point (°C.) or Refractive Index ($n_D^{20}$) |
|---|---|---|---|---|---|---|
| 573 | $C_3H_7$-i | O | O | NH | 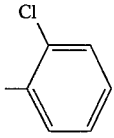 2-Cl-phenyl | |
| 574 | $C_3H_7$-i | O | O | NH | 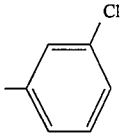 3-Cl-phenyl | |
| 575 | $C_3H_7$-i | O | O | NH | 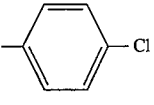 4-Cl-phenyl | |
| 576 | $C_3H_7$-i | O | O | $NCH_3$ | 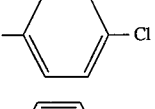 4-Cl-phenyl | |
| 577 | $C_3H_7$-i | O | O | $NCH_3$ | 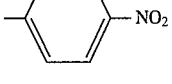 4-$NO_2$-phenyl | |
| 578 | $C_3H_7$-i | O | O | $NCH_3$ | 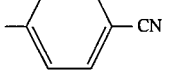 4-CN-phenyl | |
| 579 | 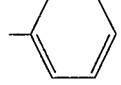 phenyl | O | O | NH | 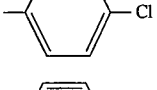 4-Cl-phenyl | |
| 580 | 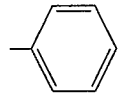 phenyl | O | O | NH | 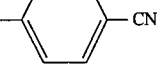 4-CN-phenyl | |
| 581 | 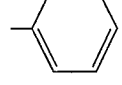 phenyl | O | O | $NCH_3$ | 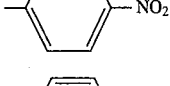 4-$NO_2$-phenyl | |
| 582 | 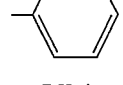 phenyl | O | O | $NCH_3$ | 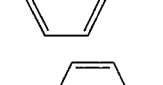 4-CN-phenyl | |
| 583 | $C_3H_7$-i | O | O | S | 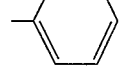 phenyl | |
| 584 | $C_3H_7$-i | O | O | S |  4-Cl-phenyl | |

TABLE 5-continued $$R^1-Z^1-\overset{\overset{Z^2}{\|}}{C}-NH-\underset{\underset{\underset{CH_3}{|}}{\overset{|}{CH}}\diagdown CH_3}{\overset{|}{CH}}-\overset{\overset{O}{\|}}{C}-NH-CH_2-CH_2-Z^3-A$$

| Compound No. | R¹ | Z¹ | Z² | Z³ | A | Melting Point (°C.) or Refractive Index ($n_D^{20}$) |
|---|---|---|---|---|---|---|
| 585 | $C_3H_7$-i | O | O | S | -C₆H₄-NO₂ (para) | |
| 586 | $C_3H_7$-i | O | O | S | -C₆H₄-CN (para) | |
| 587 | $C_3H_7$-i | O | O | O | -CH(CH₃)-C₆H₄-Cl (para) | |
| 588 | phenyl | O | O | O | -CH(CH₃)-C₆H₄-Cl (para) | |
| 589 | $C_3H_7$-i | O | O | O | 2-chloro-pyridin-3-yl | |
| 590 | $C_3H_7$-i | O | O | O | 5-chloro-pyridin-3-yl | |
| 591 | phenyl | O | O | O | 5-chloro-pyridin-3-yl | |
| 592 | $C_3H_7$-i | O | O | O | -CH₂-(furan-2-yl) | |
| 593 | $C_3H_7$-i | O | O | O | -CH(CN)-(furan-2-yl) | |
| 594 | $C_3H_7$-i | O | O | O | -CH(CN)-(benzothiophen-2-yl) | |
| 595 | phenyl | O | O | O | -CH₂-(furan-2-yl) | |
| 596 | phenyl | O | O | O | -CH(CN)-(furan-2-yl) | |

TABLE 5-continued $$R^1-Z^1-\overset{\overset{Z^2}{\|}}{C}-NH-\underset{\underset{\overset{|}{CH}}{\overset{|}{CH}}\diagup\diagdown CH_3\;CH_3}{CH}-\overset{\overset{O}{\|}}{C}-NH-CH_2-CH_2-Z^3-A$$

| Compound No. | $R^1$ | $Z^1$ | $Z^2$ | $Z^3$ | A | Melting Point (°C.) or Reflactive Index ($n_D^{20}$) |
|---|---|---|---|---|---|---|
| 597 | $C_3H_7$-i | O | O | O | $-CH_2-$ (3-pyridyl) | |
| 598 | $C_3H_7$-i | O | O | O | $-CH_2-$ (4-pyridyl) | |
| 599 | phenyl | O | O | O | $-CH_2-$ (4-pyridyl) | |
| 600 | $C_3H_7$-i | O | O | O | $-CH_2-$ (5-chlorobenzofuran-2-yl) | |
| 601 | $C_3H_7$-i | O | O | O | $-CH_2-$ (benzofuran-2-yl) | |

TABLE 6

$$R^1-Z^1-\overset{\overset{Z^2}{\|}}{C}-NH-\underset{\underset{\overset{|}{CH}}{\overset{|}{CH}}\diagup\diagdown CH_3\;CH_3}{CH}-\overset{\overset{O}{\|}}{C}-NH-\underset{\overset{|}{CH_3}}{CH}-\underset{\overset{|}{CH_3}}{CH}-Z^3-A$$

| Compound No. | $R^1$ | $Z^1$ | $Z^2$ | $Z^3$ | A | Melting Point (°C.) or Reflactive Index ($n_D^{20}$) |
|---|---|---|---|---|---|---|
| 602 | $C_4H_9$-t | O | O | O | phenyl | not determined |
| 603 | $C_4H_9$-t | O | O | O | 2-chlorophenyl | |
| 604 | $C_4H_9$-t | O | O | O | 3-chlorophenyl | |
| 605 | $C_4H_9$-t | O | O | O | 4-chlorophenyl | 1.4784 |

TABLE 6-continued $$R^1-Z^1-\overset{Z^2}{\underset{\|}{C}}-NH-\underset{\underset{CH_3}{\overset{|}{CH}}\underset{CH_3}{\overset{|}{CH}}}{\overset{|}{CH}}-\overset{O}{\underset{\|}{C}}-NH-\underset{\underset{CH_3}{\overset{|}{CH_3}}}{\overset{|}{CH}}-\underset{CH_3}{\overset{|}{CH}}-Z^3-A$$

| Compound No. | R[1] | Z[1] | Z[2] | Z[3] | A | Melting Point (°C.) or Refractive Index ($n_D^{20}$) |
|---|---|---|---|---|---|---|
| 606 | $C_4H_9$-t | O | O | O | —⌬—$NO_2$ | 1.5109 |
| 607 | $C_4H_9$-t | O | O | O | —⌬—CN | not determined |
| 608 | $C_3H_7$-i | O | O | O | —⌬—Cl | |
| 609 | $C_3H_7$-i | O | O | O | —⌬—$NO_2$ | |
| 610 | $C_3H_7$-i | O | O | O | —⌬—CN | |
| 611 | —⌬ | O | O | O | —⌬ | |
| 612 | —⌬ | O | O | O | —⌬—Cl | |
| 613 | —⌬ | O | O | O | —⌬—$NO_2$ | |
| 614 | —⌬ | O | O | O | —⌬—CN | |
| 615 | —⌬ | S | O | O | —⌬—Cl | |
| 616 | —⌬ | S | O | O | —⌬—CN | |
| 617 | —⌬ | O | S | O | —⌬—Cl | |
| 618 | —⌬ | O | S | O | —⌬—CN | |

TABLE 6-continued $$R^1-Z^1-\overset{\overset{Z^2}{\|}}{C}-NH-\underset{\underset{\underset{CH_3}{|}}{\overset{|}{CH}}}{CH}-\overset{\overset{O}{\|}}{C}-NH-\underset{\underset{CH_3}{|}}{\overset{|}{CH}}-\underset{\underset{CH_3}{|}}{\overset{|}{CH}}-Z^3-A$$

| Compound No. | R¹ | Z¹ | Z² | Z³ | A | Melting Point (°C.) or Refractive Index ($n_D^{20}$) |
|---|---|---|---|---|---|---|
| 619 |  | S | S | O | 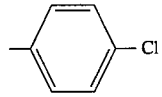 —Cl | |
| 620 | 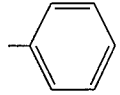 | S | S | O |  —CN | |
| 621 | $C_3H_7$-i | O | O | S |  —Cl | |
| 622 | $C_3H_7$-i | O | O | S |  —CN | |
| 623 | 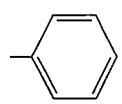 | O | O | S |  —Cl | |
| 624 | 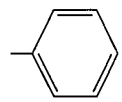 | O | O | S |  —NO₂ | |
| 625 |  | O | O | S | 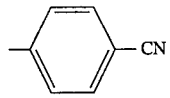 —CN | |
| 626 | 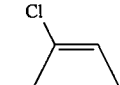 Cl | O | O | O |  —NO₂ | |
| 627 | 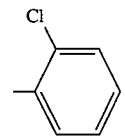 Cl | O | O | O | 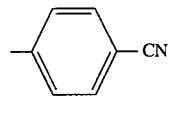 —CN | |
| 628 | 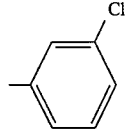 Cl | O | O | O | 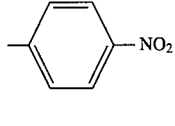 —NO₂ | |
| 629 | 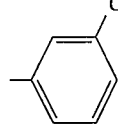 Cl | O | O | O | 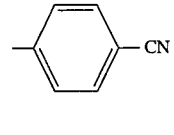 —CN | |

TABLE 6-continued $$R^1-Z^1-\overset{Z^2}{\underset{\|}{C}}-NH-\underset{\underset{CH_3}{\overset{|}{CH}}\overset{CH_3}{\diagdown}}{\overset{|}{CH}}-\overset{O}{\underset{\|}{C}}-NH-\underset{\underset{CH_3}{\overset{|}{CH}}}{\overset{|}{CH}}-\underset{CH_3}{\overset{|}{CH}}-Z^3-A$$

| Compound No. | R¹ | Z¹ | Z² | Z³ | A | Melting Point (°C.) or Reflactive Index ($n_D^{20}$) |
|---|---|---|---|---|---|---|
| 630 | 4-Cl-C₆H₄- | O | O | O | 4-NO₂-C₆H₄- | |
| 631 | 4-Cl-C₆H₄- | O | O | O | 4-CN-C₆H₄- | |
| 632 | -CH₂-C₆H₅ | O | O | O | 4-CN-C₆H₄- | |
| 633 | -CH₂-C₆H₄-CH₃ (4-) | O | O | O | 3,4-(OCH₃)₂-C₆H₃- | |
| 634 | C₃H₇-i | O | O | O | -CH(CH₃)-C₆H₄-Cl(4-) | |
| 635 | C₆H₅- | O | O | O | -CH(CH₃)-C₆H₄-Cl(4-) | |
| 636 | C₃H₇-i | O | O | O | 5-Cl-pyridin-3-yl | |
| 637 | C₆H₅- | O | O | O | 5-Cl-pyridin-3-yl | |
| 638 | C₃H₇-i | O | O | O | -CH₂-pyridin-3-yl | |
| 639 | C₃H₇-i | O | O | O | -CH₂-pyridin-4-yl | |

TABLE 7
$$R^1-O-\overset{\overset{O}{\|}}{C}-NH-\underset{\underset{\underset{CH_3}{|}}{\overset{|}{CH}}\underset{CH_3}{\diagdown}}{CH}-\overset{\overset{O}{\|}}{C}-NH-\underset{\underset{CN}{|}}{CH}-CH_2-Z^3-A$$
| Compound No. | R¹ | Z³ | A | Melting Point (°C.) or Refractive Index ($n_D^{20}$) |
|---|---|---|---|---|
| 640 | $C_4H_9$-t | O | 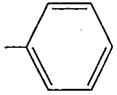 | |
| 641 | $C_4H_9$-t | O |  | |
| 642 | $C_4H_9$-t | O | 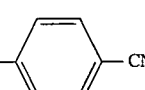 | |
| 643 | $C_3H_7$-i | O | 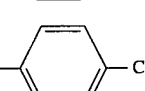 | 153–155 |
| 644 | $C_3H_7$-i | O | 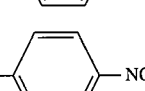 | |
| 645 | $C_3H_7$-i | O | 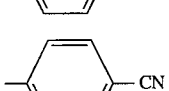 | |
| 646 | 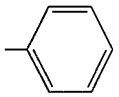 | O | 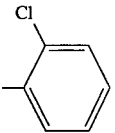 | |
| 647 | 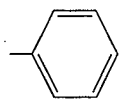 | O | 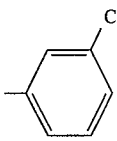 | |
| 648 | 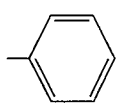 | O |  | 157–160 |
| 649 | 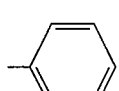 | O | 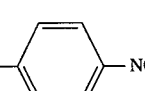 | |
| 650 | 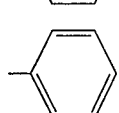 | O | 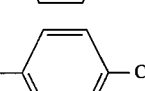 | |
| 651 | 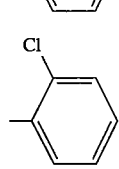 | O | 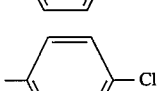 | |

TABLE 7-continued $$R^1-O-\overset{\overset{O}{\|}}{C}-NH-CH-\overset{\overset{O}{\|}}{C}-NH-CH-CH_2-Z^3-A$$
$$\underset{CH_3 \quad CH_3}{\overset{|}{CH}} \qquad \underset{CN}{|}$$

| Compound No. | R¹ | Z³ | A | Melting Point (°C.) or Reflactive Index ($n_D^{20}$) |
|---|---|---|---|---|
| 652 | 2-Cl-C₆H₄- | O | 4-CN-C₆H₄- | |
| 653 | 3-Cl-C₆H₄- | O | 4-NO₂-C₆H₄- | |
| 654 | 3-Cl-C₆H₄- | O | 4-CN-C₆H₄- | |
| 655 | 4-Cl-C₆H₄- | O | 4-NO₂-C₆H₄- | |
| 656 | 4-Cl-C₆H₄- | O | 4-CN-C₆H₄- | |
| 657 | -CH₂-C₆H₅ | O | 4-Cl-C₆H₄- | |
| 658 | -CH₂-C₆H₅ | O | 4-CN-C₆H₄- | |
| 659 | -CH₂-(4-CH₃-C₆H₄) | O | 4-NO₂-C₆H₄- | |
| 660 | -CH₂-(4-CH₃-C₆H₄) | O | 4-CN-C₆H₄- | |
| 661 | C₆H₅- | S | C₆H₅- | |
| 662 | C₆H₅- | S | 4-Cl-C₆H₄- | |
| 663 | C₆H₅- | S | 4-CN-C₆H₄- | |

TABLE 7-continued $$R^1-O-\overset{O}{\underset{\|}{C}}-NH-\underset{\underset{CH_3}{\overset{CH}{|}}\overset{}{\diagdown}CH_3}{\overset{}{C}H}-\overset{O}{\underset{\|}{C}}-NH-\underset{\underset{CN}{|}}{CH}-CH_2-Z^3-A$$

| Compound No. | R[1] | Z[3] | A | Melting Point (°C.) or Reflactive Index ($n_D^{20}$) |
|---|---|---|---|---|
| 664 | 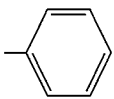 | O | 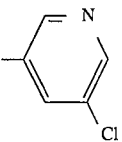 | |
| 665 | 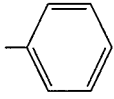 | O | 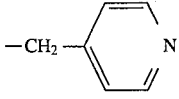 | |

TABLE 8

$$R^1-O-\overset{O}{\underset{\|}{C}}-NH-\underset{\underset{CH_3}{\overset{CH}{|}}\overset{}{\diagdown}CH_3}{\overset{}{C}H}-\overset{O}{\underset{\|}{C}}-NH-\underset{\underset{CH_3}{|}}{\overset{\overset{CH_3}{|}}{C}}-CH_2-Z^3-A$$

| Compound No. | R[1] | Z[3] | A | Melting Point (°C.) or Reflactive Index ($n_D^{20}$) |
|---|---|---|---|---|
| 666 | $C_4H_9$-t | O | 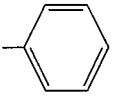 | |
| 667 | $C_4H_9$-t | O | 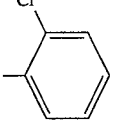 | |
| 668 | $C_4H_9$-t | O | 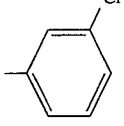 | |
| 669 | $C_4H_9$-t | O | 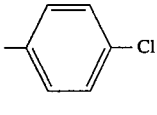 | |
| 670 | $C_3H_7$-i | O | 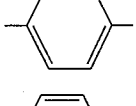 | |
| 671 | $C_3H_7$-i | O | 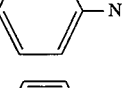 | |
| 672 | $C_3H_7$-i | O | 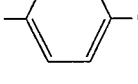 | 1.5111 |

TABLE 8-continued
$$R^1-O-\overset{O}{\underset{||}{C}}-NH-\underset{\underset{CH_3}{\overset{|}{CH}}\underset{CH_3}{\overset{|}{}}}{\overset{|}{CH}}-\overset{O}{\underset{||}{C}}-NH-\underset{\underset{CH_3}{\overset{|}{}}}{\overset{CH_3}{\overset{|}{C}}}-CH_2-Z^3-A$$
| Compound No. | R¹ | Z³ | A | Melting Point (°C.) or Refractive Index ($n_D^{20}$) |
|---|---|---|---|---|
| 673 | 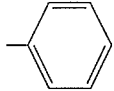 | O | 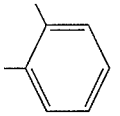 | |
| 674 | 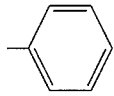 | O | 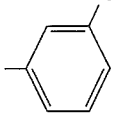 | |
| 675 | 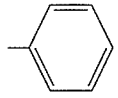 | O | 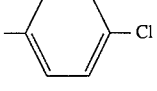 | |
| 676 | 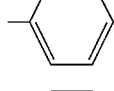 | O | 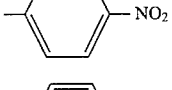 | |
| 677 | 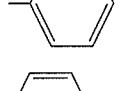 | O | 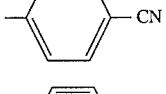 | |
| 678 | 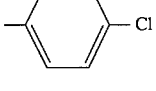 | O | 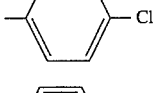 | |
| 679 | 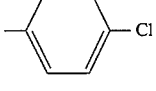 | O | 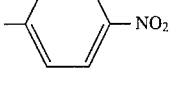 | |
| 680 | 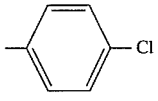 | O | 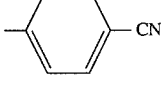 | |
| 681 | 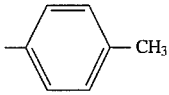 | O | 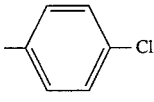 | |
| 682 | 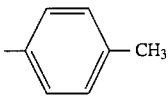 | O | 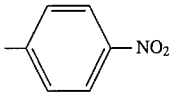 | |
| 683 | 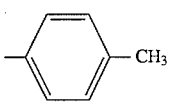 | O |  | |
| 684 | 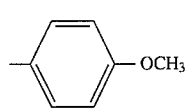 | O | 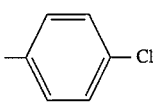 | |

TABLE 8-continued $$R^1-O-\overset{\overset{O}{\|}}{C}-NH-\overset{\underset{\underset{\underset{CH_3}{|}}{CH}}{|}}{CH}-\overset{\overset{O}{\|}}{C}-NH-\overset{\overset{CH_3}{|}}{\underset{\underset{CH_3}{|}}{C}}-CH_2-Z^3-A$$

| Compound No. | R¹ | Z³ | A | Melting Point (°C.) or Refractive Index ($n_D^{20}$) |
|---|---|---|---|---|
| 685 | ―⟨⟩―OCH₃ | O | ―⟨⟩―F | |
| 686 | ―⟨⟩―OCH₃ | O | ―⟨⟩―NO₂ | |
| 687 | ―⟨⟩―OCH₃ | O | ―⟨⟩―CN | |
| 688 | ―CH₂―⟨⟩ | O | ―⟨⟩―NO₂ | |
| 689 | ―CH₂―⟨⟩ | O | ―⟨⟩―CN | |
| 690 | ―CH₂―⟨⟩―NO₂ | O | ―⟨⟩―Cl | |
| 691 | ―CH₂―⟨⟩―NO₂ | O | ―⟨⟩―CN | |
| 692 | ―⟨⟩ | S | ―⟨⟩―Cl | |
| 693 | ―⟨⟩ | S | ―⟨⟩―NO₂ | |
| 694 | ―⟨⟩ | S | ―⟨⟩―CN | |
| 695 | C₃H₇-i | O | ―CH₂―⟨⟩ | |
| 696 | C₃H₇-i | O | ―CH₂―⟨⟩―Cl | |
| 697 | ―⟨⟩ | O | ―CH₂―⟨⟩ | |

TABLE 8-continued $$R^1-O-\overset{O}{\underset{\|}{C}}-NH-\underset{\underset{CH_3}{\overset{|}{CH}}\diagdown CH_3}{\overset{|}{CH}}-\overset{O}{\underset{\|}{C}}-NH-\underset{\underset{CH_3}{\overset{|}{C}}}{\overset{CH_3}{\overset{|}{C}}}-CH_2-Z^3-A$$

| Compound No. | R¹ | Z³ | A | Melting Point (°C.) or Reflactive Index ($n_D^{20}$) |
|---|---|---|---|---|
| 698 | ⌬ (phenyl) | O | —CH₂—⌬—Cl | |

TABLE 9

$$R^1-O-\overset{O}{\underset{\|}{C}}-NH-\underset{\underset{CH_3}{\overset{|}{CH}}\diagdown CH_3}{\overset{|}{CH}}-\overset{O}{\underset{\|}{C}}-NH-\underset{\overset{|}{C_2H_5}}{\overset{|}{CH}}-CH_2-Z^3-A$$

| Compound No. | R¹ | Z³ | A | Melting Point (°C.) or Reflactive Index ($n_D^{20}$) |
|---|---|---|---|---|
| 699 | C₄H₉-t | O | —⌬ | |
| 700 | C₄H₉-t | O | —⌬(2-Cl) | |
| 701 | C₄H₉-t | O | —⌬(3-Cl) | |
| 702 | C₄H₉-t | O | —⌬—Cl | |
| 703 | C₃H₇-i | O | —⌬—Cl | |
| 704 | C₃H₇-i | O | —⌬—NO₂ | |
| 705 | C₃H₇-i | O | —⌬—CN | |
| 706 | ⌬ (phenyl) | O | —⌬—Cl | |

TABLE 9-continued
$$R^1-O-\overset{O}{\underset{\|}{C}}-NH-CH-\overset{O}{\underset{\|}{C}}-NH-CH-CH_2-Z^3-A$$
$$\underset{\underset{CH_3\ \ CH_3}{CH}}{|} \quad \underset{C_2H_5}{|}$$
| Compound No. | R¹ | Z³ | A | Melting Point (°C.) or Refractive Index ($n_D^{20}$) |
|---|---|---|---|---|
| 707 | 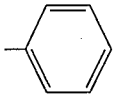 | O | 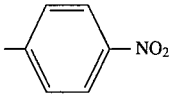 —NO₂ | |
| 708 | 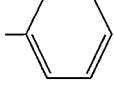 | O | 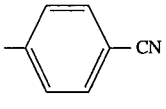 —CN | 128–130 |
| 709 | 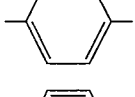 —Cl | O | 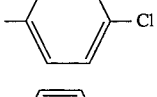 —Cl | |
| 710 | 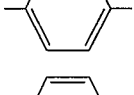 —Cl | O | 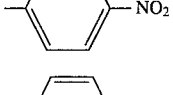 —NO₂ | |
| 711 | 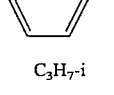 —Cl | O | 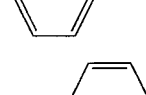 —CN | |
| 712 | C₃H₇-i | O | —CH₂— 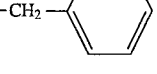 | |
| 713 | C₃H₇-i | O | —CH₂— 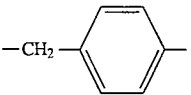 —Cl | |
| 714 | C₃H₇-i | O | —CH(CH₃)— 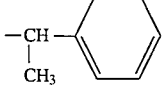 | |
| 715 | 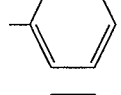 | O | —CH₂— 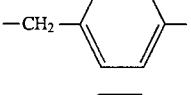 —Cl | |
| 716 | 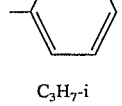 | O | —CH(CH₃)— 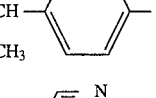 —Cl | |
| 717 | C₃H₇-i | O | 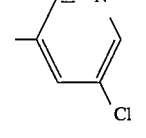 (pyridyl, Cl) | |
| 718 | C₃H₇-i | O | —CH₂— 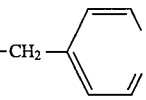 (pyridyl) | |

TABLE 9-continued $$R^1-O-\overset{O}{\underset{\|}{C}}-NH-\underset{\underset{CH_3}{\overset{|}{CH}}\diagdown CH_3}{\overset{|}{CH}}-\overset{O}{\underset{\|}{C}}-NH-\underset{\underset{C_2H_5}{\overset{|}{\phantom{C}}}}{CH}-CH_2-Z^3-A$$

| Compound No. | R$^1$ | Z$^3$ | A | Melting Point (°C.) or Reflactive Index (n$_D^{20}$) |
|---|---|---|---|---|
| 719 | 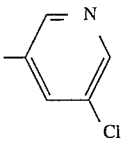 | O | 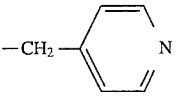 | |
| 720 | 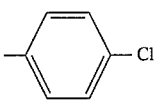 | O | —CH$_2$— 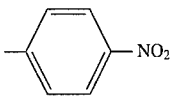 | |
| 721 | C$_3$H$_7$-i | S | 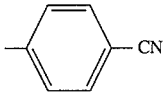 | |
| 722 | C$_3$H$_7$-i | S | 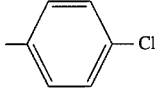 | |
| 723 | C$_3$H$_7$-i | S | 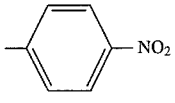 | |
| 724 | 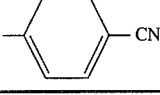 | S | —⟨ ⟩—Cl | |
| 725 | 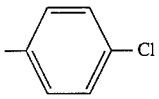 | S | —⟨ ⟩—NO$_2$ | |
| 726 | 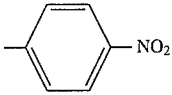 | S | —⟨ ⟩—CN | |

TABLE 10

$$R^1-O-\overset{O}{\underset{\|}{C}}-NH-\underset{\underset{CH_3}{\overset{|}{CH}}\diagdown CH_3}{\overset{|}{CH}}-\overset{O}{\underset{\|}{C}}-NH-\underset{\underset{C_3H_7}{\overset{|}{\phantom{C}}}}{CH}-CH_2-Z^3-A$$

| Compound No. | R$^1$ | Z$^3$ | A | Melting Point (°C.) or Reflactive Index (n$_D^{20}$) |
|---|---|---|---|---|
| 727 | C$_4$H$_9$-t | O | —⟨ ⟩—Cl | |
| 728 | C$_4$H$_9$-t | O | —⟨ ⟩—NO$_2$ | |

TABLE 10-continued $$R^1-O-\underset{\underset{}{\overset{O}{\|}}}{C}-NH-\underset{\underset{\underset{CH_3}{\diagdown}\phantom{CH}\underset{CH_3}{\diagup}}{\underset{CH}{|}}}{CH}-\underset{\underset{}{\overset{O}{\|}}}{C}-NH-\underset{\underset{C_3H_7}{|}}{CH}-CH_2-Z^3-A$$

| Compound No. | R$^1$ | Z$^3$ | A | Melting Point (°C.) or Reflactive Index (n$_D^{20}$) |
|---|---|---|---|---|
| 729 | C$_4$H$_9$-t | O | —C$_6$H$_4$—CN | |
| 730 | C$_3$H$_7$-i | O | —C$_6$H$_4$—Cl | |
| 731 | C$_3$H$_7$-i | O | —C$_6$H$_4$—NO$_2$ | |
| 732 | C$_3$H$_7$-i | O | —C$_6$H$_4$—CN | |
| 733 | C$_6$H$_5$ | O | —C$_6$H$_4$—Cl | |
| 734 | C$_6$H$_5$ | O | —C$_6$H$_4$—NO$_2$ | |
| 735 | C$_6$H$_5$ | O | —C$_6$H$_4$—CN | |
| 736 | C$_3$H$_7$-i | S | —C$_6$H$_4$—Cl | |
| 737 | C$_3$H$_7$-i | S | —C$_6$H$_4$—CN | |
| 738 | C$_6$H$_5$ | S | —C$_6$H$_4$—CN | |

TABLE 11

$$R^1-O-\overset{\overset{O}{\|}}{C}-NH-\underset{\underset{\underset{CH_3}{|}}{\overset{|}{CH}}\phantom{xx}CH_3}{\overset{|}{CH}}-\overset{\overset{O}{\|}}{C}-NH-CH_2-CH_2-CH_2-Z^3-A$$

| Compound No. | R¹ | Z³ | A | Melting Point (°C.) or Refractive Index ($n_D^{20}$) |
|---|---|---|---|---|
| 739 | —CH₂—C₆H₄—CH₃ (p) | O | 3,4-(OCH₃)₂-C₆H₃— | |
| 740 | C₃H₇-i | O | 4-NO₂-C₆H₄— | |
| 741 | C₃H₇-i | O | 4-CN-C₆H₄— | 150–151 |
| 742 | C₆H₅— | O | 4-Cl-C₆H₄— | |
| 743 | C₆H₅— | O | 4-NO₂-C₆H₄— | |
| 744 | C₆H₅— | O | 4-CN-C₆H₄— | |
| 745 | C₃H₇-i | S | 4-CN-C₆H₄— | |
| 746 | C₆H₅— | S | 4-CN-C₆H₄— | |
| 747 | C₃H₇-i | O | —CH₂—C₆H₄—Cl (p) | |
| 748 | C₃H₇-i | O | 5-Cl-pyridin-3-yl | |
| 749 | C₃H₇-i | O | —CH₂-pyridin-4-yl | |

TABLE 12
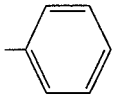
| Compound No. | R¹ | R⁴ | R⁵ | R⁶ | A | Melting Point (°C.) or Reflactive Index ($n_D^{20}$) |
|---|---|---|---|---|---|---|
| 750 | 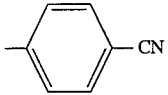 | H | H | CH₃ | 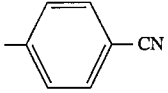—CN | not determined |
| 751 | C₄H₉-t | H | H | CH₃ | —CN | 46–50 |
| 752 | C₃H₇-i | H | H | CH₃ | 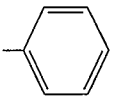—CN | |
| 753 | 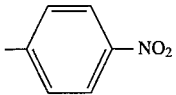 | H | H | CH₃ | 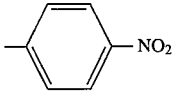—NO₂ | |
| 754 | C₄H₉-t | H | H | CH₃ | 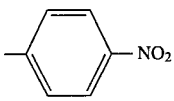—NO₂ | |
| 755 | C₃H₇-i | H | H | CH₃ | 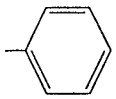—NO₂ | |
| 756 | 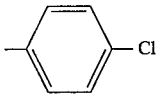 | H | H | CH₃ | 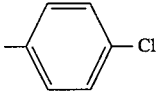—Cl | |
| 757 | C₄H₉-t | H | H | CH₃ | 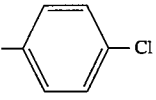—Cl | |
| 758 | C₃H₇-i | H | H | CH₃ | 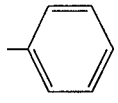—Cl | |
| 759 |  | H | CH₃ | CH₃ | 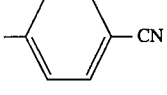—CN | |
| 760 | C₄H₉-t | H | CH₃ | CH₃ | 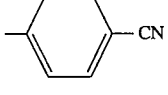—CN | |
| 761 | C₃H₇-i | H | CH₃ | CH₃ | 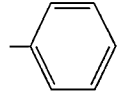—CN | |
| 762 | 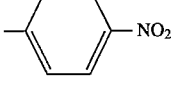 | H | CH₃ | CH₃ | —NO₂ (phenyl) | |

TABLE 12-continued $$R^1-O-\overset{\overset{O}{\|}}{C}-NH-\underset{\underset{\underset{CH_3}{|}}{\overset{|}{CH}}}{\overset{|}{CH}}-\overset{\overset{O}{\|}}{C}-NH-\underset{\underset{R^4}{|}}{\overset{|}{CH}}-\underset{\underset{R^6}{|}}{\overset{\overset{R^5}{|}}{C}}-O-A$$

| Compound No. | $R^1$ | $R^4$ | $R^5$ | $R^6$ | A | Melting Point (°C.) or Reflactive Index ($n_D^{20}$) |
|---|---|---|---|---|---|---|
| 763 | $C_4H_9$-t | H | $CH_3$ | $CH_3$ | —C₆H₄—NO₂ | |
| 764 | $C_3H_7$-i | H | $CH_3$ | $CH_3$ | —C₆H₄—NO₂ | |
| 765 | phenyl | H | $CH_3$ | $CH_3$ | —C₆H₄—Cl | |
| 766 | $C_4H_9$-t | H | $CH_3$ | $CH_3$ | —C₆H₄—Cl | |
| 767 | $C_3H_7$-i | H | $CH_3$ | $CH_3$ | —C₆H₄—Cl | |
| 768 | phenyl | $C_3H_7$-i | H | H | —C₆H₄—CN | 150–152 |
| 769 | $C_4H_9$-t | $C_3H_7$-i | H | H | —C₆H₄—CN | |
| 770 | $C_3H_7$-i | $C_3H_7$-i | H | H | —C₆H₄—CN | 154–157 |
| 771 | phenyl | $C_3H_7$-i | H | H | —C₆H₄—NO₂ | |
| 772 | $C_4H_9$-t | $C_3H_7$-i | H | H | —C₆H₄—NO₂ | |
| 773 | $C_3H_7$-i | $C_3H_7$-i | H | H | —C₆H₄—NO₂ | |
| 774 | phenyl | $C_3H_7$-i | H | H | —C₆H₄—Cl | |
| 775 | $C_4H_9$-t | $C_3H_7$-i | H | H | —C₆H₄—Cl | |

TABLE 12-continued

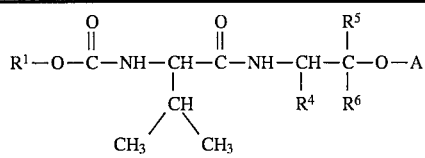

| Compound No. | $R^1$ | $R^4$ | $R^5$ | $R^6$ | A | Melting Point (°C.) or Reflective Index ($n_D^{20}$) |
|---|---|---|---|---|---|---|
| 776 | $C_3H_7$-i | $C_3H_7$-i | H | H |  | |

The compounds represented by Formula [I] according to the present invention can be prepared, for example, in the following manner.

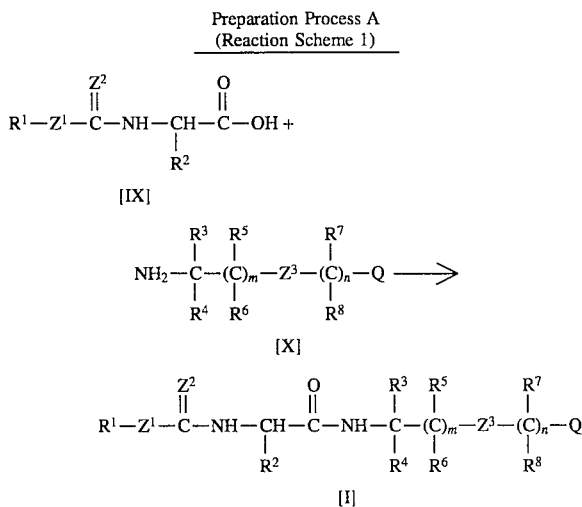

wherein $R^1$, $R^2$, $R^3$, $R^4$, $R^5$, $R^6$, $R^7$, $R^8$, $Z^1$, $Z^2$, $Z^3$, Q, m, and n have the same meanings as defined above.

The compounds represented by Formula [I] according to the present invention can be prepared by reacting an amino acid derivative represented by Formula [IX] or the amino acid derivative wherein the carboxyl group is activated, with an amine represented by Formula [X] in the presence of a base and/or a catalyst, if necessary.

In the present reaction, as the amino acid derivative represented by Formula [IX] with an activated carboxyl group, there can be mentioned, for example, an acid halide such as an acid chloride, an acid anhydride derived from the two molecules of the amino acid derivatives represented by Formula [IX], a mixed acid anhydride derived from the amino acid derivative represented by Formula [IX] and other acid or an O-alkyl carbonic acid, and an activated ester such as p-nitrophenyl ester, 2-tetrahydropyranyl ester, and 2-pyridyl ester and the like. These amino acid derivatives with activated carboxyl groups can be synthesized according to conventional methods [for example, see *Methoden der Organischen Chemie*, Vol. 15, No. 2, from page 2; Georg Thieme Verlag Stuttgart: 1974; *Chemische Berichte*, Vol. 38, page 605 (1905); *Journal of the American Chemical Society*, Vol. 74, page 676 (1952); and *Journal of the American Chemical Society*, Vol. 86, page 1839 (1964)].

In addition, it is also possible to perform the present reaction using a condensing agent such as N,N'-dicyclohexylcarbodiimide, carbonyldiimidazole, 2-chloro- 1,3-dimethylimidazolium chloride, or the like.

The present reaction can be performed in a conventional solvent: this solvent can be any solvent that does not hinder the reaction, for example, hydrocarbons such as pentane, hexane, heptane, cyclohexane, petroleum ether, ligroin, benzene, toluene, xylene and the like, halogenated hydrocarbons such as dichloromethane, dichloroethane, chloroform, carbon tetrachloride, chlorobenzene, dichlorobenzene and the like, ethers such as diethyl ether, diisopropyl ether, ethylene glycol dimethyl ether, tetrahydrofuran, dioxane and the like, ketones such as acetone, methyl ethyl ketone, methyl isopropyl ketone, methyl isobutyl ketone and the like, esters such as methyl acetate, ethyl acetate and the like, nitriles such as acetonitrile, propionitrile, benzonitrile and the like aprotic polar solvents such as dimethylsulfoxide, dimethylformamide, sulfolane and the like, and mixed solvents combining solvents selected from the aforementioned.

The base can be any type of base generally used in this type of reaction. For example, there can be mentioned hydroxides of alkaline metals such as sodium hydroxide, potassium hydroxide and the like, hydroxides of alkaline earth metals such as calcium hydroxide and the like, carbonates of alkaline metals such as sodium carbonate, potassium carbonate and the like, bicarbonates of alkaline metals such as sodium bicarbonate, potassium bicarbonate and the like, organic bases such as triethylamine, trimethylamine, dimethylaniline, pyridine, N-methylmorpholine, N-methylpiperidine, 1,5-diazabicyclo [4.3.0] non-5-ene (DBN), 1,8-diazabicyclo[5.4.0] undec-7-ene (DBU), and the like, and preferably tertiary amines such as triethylamine, pyridine, N-methylpiperidine and the like.

As the catalyst, there can be mentioned 4-dimethylaminopyridine, 1-hydroxybenzotriazole, dimethylformamide and the like. The present reaction is carried out at a temperature of –75° C. to 100° C., preferably –60° C. to 40° C. The reaction time is preferably 1 to 20 hours.

Furthermore, compounds represented by formula [IX] as the starting material can generally be synthesized by conventional methods [for example, see *Methoden der Organischen Chemie*, Vol. 15, No. 2, from page 2; *Georg Thieme Verlag Stuttgart*: 1974; *Chemistry of the Amino Acids*, vol. 2, page 891; John Wiley & Sons, New York (1964); and *Journal of the American Chemical Society*, Vol. 79, page 4686 (1957)]. Various manufacturing methods for compounds [X] can also be considered such as those methods stated in Japanese patent application First Publication No. Sho 63-146876, *Tetrahedron Letters*, page 21, 1973, and Japanese Patent Application, First Publication, No. Hei 5-271206).

Preparation Process B
(Reaction Scheme 2)

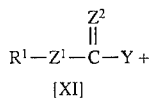

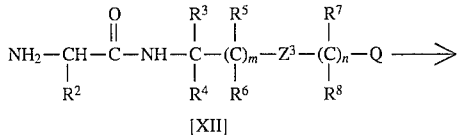

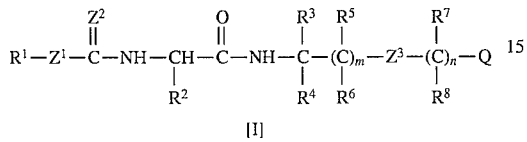

wherein $R^1$, $R^2$, $R^3$, $R^4$, $R^5$, $R^6$, $R^7$, $R^8$, $Z^1$, $Z^2$, $Z^3$, Q, m n have the same meanings as defined above, and Y represents a halogen atom, a 4,6-dimenylpyrimidinylthio group, an $R^1OC(O)O-$ group, or an $-ON=C(CN)Ph$ group (in which Ph represents a phenyl group).

Compounds of the present invention represented by Formula [I] can be manufactured by means of reacting the compound represented by Formula [XI] with an amine represented by Formula [XII] or the salt of the amine derivative with an inorganic acid such as hydrochloride and the like, or a salt of the amine derivative with an organic acid such as rosylate and the like, in the presence of a base when required.

The present reaction can be performed in a conventional solvent: this solvent can be any solvent that does not hinder the reaction, for example, hydrocarbons such as pentane, hexane, heptane, cyclohexane, petroleum ether, ligroin, benzene, toluene, xylene and the like, halogenated hydrocarbons such as dichloromethane, dichloroethane, chloroform, carbon tetrachloride, chlorobenzene, dichlorobenzene and the like, ethers such as diethyl ether, diisopropyl ether, ethylene glycol dimethyl ether, tetrahydrofuran, dioxane and the like, ketones such as acetone, methyl ethyl ketone, methyl isopropyl ketone, methyl isobutyl ketone and the like, esters such as methyl acetate, ethyl acetate and the like, nitriles such as acetonitrile, propionitrile, benzonitrile and the like, aprotic polar solvents such as dimethylsulfoxide, dimethylformamide, sulfolane and the like, water, and mixed solvents combining solvents selected from the aforementioned.

The base can be any type of base generally used in this type of reaction. For example, there can be mentioned hydroxides of alkaline metals such as sodium hydroxide, potassium hydroxide and the like, hydroxides of alkaline earth metals such as calcium hydroxide and the like, carbonates of alkaline metals such as sodium carbonate, potassium carbonate and the like, bicarbonates of alkaline metals such as sodium bicarbonate, potassium bicarbonate and the like, organic bases such as triethylamine, trimethylamine, dimethylaniline, N-methylmorpholine, pyridine, N-methylpiperidine, 1,5-diazabicyclo [4.3.0] non-5-ene (DBN), 1,8-diazabicyclo [5.4.0]-undec-7-ene (DBU), and the like, and preferably tertiary amines such as triethylamine, pyridine, N-methylpiperidine and the like. The present reaction is carried out at a temperature of −20° C. to 100° C., preferably 0° C. to 40° C. The reaction time is preferably 30 minutes to 20 hours.

Compounds represented by Formula [XII] as the starting material represent novel compounds, and can be manufactured, for example, by means of treating carbamates of compounds [I] synthesized by the procedure of preparation process A using a conventional process for removing the amino protecting group of the amino acid such as catalytic reduction, or by treating with acids such as liquid hydrofluoric acid, sulfonic acids, hydrochloric acid, hydrobromic acid, formic acid and the like.

In the following, synthesis examples of amino-acid amide derivatives, which are novel intermediates of the compounds of the present invention represented by Formulae [X] and [XII], are provided as reference examples.

REFERENCE EXAMPLE 1

Synthesis of
2-(4-cyanophenoxy)-1-methylethylamine
(Intermediate Compound No. 1)

293 g of ammonium acetate and 16.7 g of sodium cyanoborohydride were added to a solution containing 66.5 g of 4-cyanophenoxyacetone dissolved in 1500 mL of methanol, and the resultant mixture was stirred for 30 hours at room temperature. The reaction mixture was then concentrated under reduced pressure, and acidified with concentrated hydrochloric acid. 500 mL of diethyl ether and 300 mL of water were then added thereto. Subsequently, the resultant water layer was made basic with a 5% aqueous solution of sodium hydroxide, the solution was extracted with 1000 mL of diethyl ether, and then washed with water. The organic layer was then dried over anhydrous sodium sulfate, and the diethyl ether was removed under reduced pressure. The obtained residue was distilled under reduced pressure to yield 13.0 g of the desired product (19%). Boiling point: 132° C./0.26 mmHg.

REFERENCE EXAMPLE 2

Synthesis of
2-(4-chloro-2-methylphenoxy)-1-methylethylamine
(Intermediate Compound No. 2)

120 g of ammonium acetate and 9.8 g of sodium cyanoborohydride were added to a solution containing 31 g of (4-chloro-2-methylphenoxy)acetone dissolved in 700 mL of methanol, and the resultant mixture was stirred for 20 hours at room temperature. After the reaction mixture was concentrated under reduced pressure, 180 mL of concentrated hydrochloric acid and 100 mL of water were added to the residue. The whole mixture was stirred for 1 hour, and then extracted with 300 mL of diethyl ether. The water layer was alkalified using a 5% aqueous solution of sodium hydroxide, and then extracted with 500 mL of ethyl acetate. The organic layer was washed with water, dried over anhydrous magnesium sulfate, and then concentrated under reduced pressure. A fraction possessing a low boiling point was removed from the obtained oily products to afford 25 g (yield 81%) of the desired product. Refractive index: 1.5360.

REFERENCE EXAMPLE 3

Synthesis of
2-(4-chlorophenoxy)-1-methylpropylamine
(Intermediate Compound No. 3)

82 g of ammonium acetate and 6.7 g of sodium cyanoborohydride were added to a solution containing 21 g of 3-(4-chlorophenoxy)-2-butanone dissolved in 500 mL of methanol, and the reaction mixture was stirred for 20 hours at room temperature. The reaction mixture was then concentrated under reduced pressure, and 180 mL of concentrated hydrochloric acid and 100 mL of water were added to the residue. The whole mixture was extracted with 300 mL of diethyl ether. The obtained water layer was alkalified using a 5% aqueous solution of sodium hydroxide, and then extracted with 500 mL of ethyl acetate. The organic layer was washed with water, dried over anhydrous magnesium sulphate, and then concentrated under reduced pressure. A fraction possessing a low boiling point was removed from the obtained oily products to afford 18 g (yield 86%) of the desired product. Refractive index: 1.5360.

REFERENCE EXAMPLE 4

Synthesis of
1-methyl-2-(2-methylphenoxy)ethylamine
(Intermediate Compound No. 4)

A solution containing 36 g of 2-(2-methylphenoxy)acetone oxime O-methyl ether dissolved in 150 mL of dimethoxyethane was added dropwise to a suspension containing 13 g of sodium borohydride in 500 mL of dimethoxyethane at room temperature. After the mixture was stirred for 15 minutes at room temperature, a solution containing 66 g of trifluoroborane diethyl ether complex dissolved in 100 mL of dimethoxyethane was added dropwise to the mixture at room temperature. The reaction mixture was stirred for 30 minutes at room temperature and then refluxed for 3 hours. The resultant mixture was allowed to sit and cool naturally to room temperature and then acidified using a 10% hydrochloric acid. The dimethoxyethane layer was concentrated and combined with the water layer. The mixture was alkalified using sodium carbonate, and then extracted with dichloromethane, followed by washing with water. The organic layer was dried over anhydrous magnesium sulfate, and then the dichloromethane was removed under reduced pressure. The residue was distilled under reduced pressure to obtain 6.4 g (yield 21%) of the desired product. Boiling point: 65° C./0.08 mmHg.

REFERENCE EXAMPLE 5

Synthesis of 2-(4-cyanophenoxy)-
1-methylethylamine
(Intermediate Compound No. 1)

50.0 g of 2-amino-1-propanol was added dropwise to a stirred mixture of 29.3 g of 60% sodium hydride and 300 mL of N,N-dimethylformamide at 0° C. After the reaction mixture was stirred for 30 minutes at 0° C., a solution containing 121.2 g of 4-bromobenzonitrile dissolved in N,N-dimethylformamide was added dropwise to the reaction mixture. The resultant mixture was stirred for 20 hours at room temperature. After completion of the reaction, the resultant mixture was poured into water and extracted with ethyl acetate. The organic layer was washed with water and then dried over anhydrous magnesium sulfate. The ethyl acetate was removed under reduced pressure. The residue was distilled under reduced pressure to obtain 48.0 g of the desired product (yield 41%). Boiling point: 132° C./0.26 mmHg.

REFERENCE EXAMPLE 6

Synthesis of
(−)-2-(4-cyanophenoxy)-1-methylethylamine
(Intermediate Compound No. 5)

25.0 g of R-(−)-2-amino-1-propanol was added dropwise to a stirred mixture of 14.0 g of 60% sodium hydride and 200 mL of N,N-dimethylformamide at a temperature of 5° C. to 10° C. After the reaction mixture was stirred for 30 minutes, a solution containing 45.0 g of 4-chlorobenzonitrile dissolved in N,N-dimethylformamide was added dropwise to the reaction mixture. The reaction mixture was stirred for 20 hours at room temperature. After completion of the reaction, the reaction mixture was poured into water and extracted with ethyl acetate. The organic layer was washed with water and then dried over anhydrous magnesium sulfate. The ethyl acetate was removed under reduced pressure. The residue was distilled under reduced pressure to obtain 33.0 g of the desired product (yield: 56%). Boiling point: 60°–66° C./0.08 mmHg, $[\alpha]_D^{20}$ −15.7° (C1.0 CH$_3$OH).

REFERENCE EXAMPLE 7

Synthesis of
1-methyl-2-(2-pyrimidyloxy)ethylamine
(Intermediate Compound No. 6)

2.0 g of 2-amino-1-propanol was added dropwise to a stirred mixture of 1.3 g of 60% sodium hydride and 30 mL of N,N-dimethylformamide at room temperature. After the reaction mixture was stirred for 30 minutes, a solution containing 3.7 g of 2-chloropyrimidine dissolved in N,N-dimethylformamide was added dropwise to the reaction mixture. The mixture was stirred for 2 hours at 100° C. After completion of the reaction, the reaction mixture was cooled. The solids were filtered off. The solvent in the filtrate was removed under reduced pressure. The residue was purified by column chromatography on silica gel to obtain 2.1 g of the desired product (yield: 50%). Refractive index: 1.5481.

REFERENCE EXAMPLE 8

Synthesis of 1-methyl-2-(4-pyridyloxy)ethylamine
(Intermediate Compound No. 7)

6.2 g of 2-amino-1-propanol was added dropwise to a stirred mixture of 4.0 g of 60% sodium hydride and 50 mL of N,N-dimethylformamide at 5° C.–10° C. After the reaction mixture was stirred for 30 minutes, 12.5 g of 4-chloropyridine hydrochloride in limited amounts was added to the reaction mixture. The mixture was stirred for 20 hours at room temperature. After completion of the reaction, the solids were filtered off. The solvent in the filtrate was removed under reduced pressure. The residue was purified by column chromatography on silica gel to obtain 3.8 g of the desired product (yield: 30%). Refractive index: 1.5469.

Specific examples of intermediate [X] obtained through the operations of Reference Examples 1 to 8 are shown in Table 13.

TABLE 13

$$NH_2-CH(R^6)-CH(CH_3)-O-\phantom{x}\!\!\!\!\!\!-X_p$$

| Intermediate Compound No. | $R^6$ | Xp | Reflactive Index ($n_D^{20}$) or Boiling Point (°C./mmHg) |
|---|---|---|---|
| 8 | H | 2-OCH$_3$ | 96.5/0.15 |
| 9 | H | 3-OCH$_3$ | 1.5158 |
| 10 | H | 4-OCH$_3$ | 95/0.10 |
| 11 | H | 2-CN | 1.5566 |
| 12 | H | 3-CN | 1.5409 |
| 13 | H | 2-F | 70/0.22 |
| 14 | H | 3-F | 74/0.15 |
| 15 | H | 2-NO$_2$ | 1.5582 |
| 16 | H | 2,4-Cl$_2$ | 1.5475 |
| 17 | H | 3,4-Cl$_2$ | 107/0.16 |
| 18 | H | 3,5-Cl$_2$ | 100/0.12 |
| 19 | H | 3,4-(OCH$_3$)$_2$ | 1.5361 |
| 20 | H | 3,5-(OCH$_3$)$_2$ | 12.5/0.10 |
| 21 | CH$_3$ | 4-CN | 1.5480 |
| 22 | CH$_3$ | 4-NO$_2$ | 1.6263 |

REFERENCE EXAMPLE 9

Synthesis of N$^1$-[2-(4-cyanophenoxy)-1-methylethyl]-L-valinamide hydrochloride (Intermediate Compound No. 23)

Hydrogen chloride gas was introduced into a solution containing 3.7 g of N2-tert-butoxycarbonyl-N$^1$-[2-(4-cyanophenoxy)-1-methylethyl]-L-valinamide dissolved in 100 mL of methylene chloride for 1 hour at room temperature. After completion of the reaction, the methylene chloride was removed under reduced pressure, thus obtaining a crude crystal. The crude crystal was washed with acetone to afford 3.1 g of the desired product (yield: 100%). Melting point: 59°–63° C.

REFERENCE EXAMPLE 10

Synthesis of N$^1$-[2-(4-cyanophenoxy)-1-methylethyl]-L-isoleucinamide (Intermediate Compound No. 24)

Hydrogen chloride gas was introduced into a solution containing 15.0 g of N$^2$-tert-butoxycarbonyl-N$^1$-[2-(4-cyanophenoxy)-1-methylethyl]-L-isoleucinamide dissolved in 300 mL of methylene chloride for 1 hour at room temperature. After completion of the reaction, the methylene chloride was removed under reduced pressure, thus obtaining a crude crystal. 200 ml of a saturated aqueous solution of sodium bicarbonate and 200 ml of methylene chloride were added to the crude crystal, and the mixture was stirred for 30 minutes and extracted with methylene chloride. The organic layer was washed with water, and dried over anhydrous sodium sulfate. The methylene chloride was removed under reduced pressure. The obtained crude product was washed with acetone to afford 10.0 g of the desired product (yield: 90%). Melting point: 64°–67° C.

Specific examples of Intermediate [XII] obtained through the operations of Reference Examples 9 and 10 are shown in Table 14.

TABLE 14

$$NH_2-\overset{L}{\underset{R^2}{CH}}-\overset{O}{\underset{}{C}}-NH-\underset{CH_3}{CH}-CH_2-O-Q$$

| Intermediate Compound No. | $R^2$ | Q | Reflactive Index ($n_D^{20}$) or Boiling Point (°C./mmHg) |
|---|---|---|---|
| 25 | C$_3$H$_7$-i | 2-CF$_3$-pyridin-5-yl | 73–75 |
| 26 | C$_2$H$_5$ | 4-Cl-phenyl | 43–44 |
| 27 | C$_2$H$_5$ | 4-CN-phenyl | 1.5391 |
| 28 | C$_3$H$_7$ | 4-CN-phenyl | 1.5299 |
| 29 | C$_4$H$_9$-t | 4-CN-phenyl | 1.5251 |
| 30 | C$_3$H$_7$-i | 4-CN-phenyl | 1.5250 |

The Best Mode for Carrying Out the Invention

The methods for producing the compounds according to the present invention as well as the use of the compounds will be described in detail in the following Synthesis Examples.

SYNTHESIS EXAMPLE 1

Synthesis of N$^2$-tert-butoxycarbonyl-N$^1$-[1-methyl-2-(4-nitrophenoxy)ethyl]-L-valinamide (Compound No. 16)

0.5 g of N-methylpiperidine was added to a solution containing 1.1 g of N-tert-butoxycarbonyl-L-valine dissolved in 40 ml of methylene chloride, at –20° C. After the mixture was stirred for 10 minutes at the same temperature, 0.7 g of isobutyl chloroformate was added to the mixture at –40° C., and stirred for 1 hour at –20° C. 1 g of 1-methyl-2-(4-nitrophenoxy)ethylamine was added to this mixture at -60° C., and then the reaction mixture was allowed to sit and warm naturally to room temperature while being stirred, and was stirred for 15 hours at room temperature. Water was subsequently added to the reaction mixture. After the dichloromethane layer was successively washed with a 5% aqueous solution of sodium bicarbonate and water, the organic layer was dried over anhydrous magnesium sulfate and the methylene chloride was removed under reduced pressure. The residue, which was a crude crystal, was purified by column chromatography on silica gel, thus obtaining 0.7 g of the desired product in the form of a yellow powder (yield: 55%).

SYNTHESIS EXAMPLE 2

Synthesis of
$N^1$-[2-(4-cyanophenoxy)-1-methylethyl]-$N^2$-isopropenyloxycarbonyl-L-valinamide
(Compound No. 77)

0.6 g of N-methylmorpholine, and subsequently 0.4 g of isopropyl chloroformate were added to a solution containing 0.9 g of $N^1$-[2-(4-cyanophenoxy)-1-methylethyl]L-valinamide hydrochloride dissolved in 50 ml of methylene chloride at −15° C. The mixture was allowed to sit and warm naturally to room temperature and stirred for 15 hours at room temperature. Water was subsequently added to the reaction mixture. After the dichloromethane layer was washed with water, the organic layer was dried over anhydrous magnesium sulfate and then the methylene chloride was removed under reduced pressure. The residue was purified by column chromatography on silica gel, thus obtaining 0.23 g of the desired product in the form of colorless grains (yield: 13%).

SYNTHESIS EXAMPLE 3

Synthesis of
$N^1$-[2-(4-cyanophenoxy)-1-methylethyl]-$N^2$-phenoxycarbonyl-L-valinamide
(Compound No. 107)

1.3 g of N-methylpiperidine was added to a solution containing 3 g of N-phenoxycarbonyl-L-valine dissolved in 50 mL of methylene chloride, at −20° C. After the mixture was stirred for 10 minutes at the same temperature, 1.7 g of isobutyl chloroformate was added to the mixture at −40° C., and stirred for 1 hour at −20° C. 2.2 g of 2-(4-cyanophenoxy)-1-methylethylamine was added to this mixture at −60° C., and then the reaction mixture was allowed to sit and warm naturally to room temperature, with stirring, and stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue, which was a crude crystal, was purified by column chromatography on silica gel, thus obtaining 1.1 g of the desired product in the form of a white powder (yield: 22%).

SYNTHESIS EXAMPLE 4

Synthesis of
$N^2$-tert-butoxycarbonyl-$N^1$-[2-(4-cyanophenoxy)-1-methylethyl]-L-isoleucinamide
(Compound No. 228)

1.3 g of N-methylpiperidine was added to a solution containing 3 of N-tert-butoxycarbonyl-L-isoleucine dissolved in 60 mL of methylene chloride, at −20° C. After the mixture was stirred for 10 minutes at the same temperature, 1.8 g of isobutyl chloroformate was added to the mixture at −40° C., and stirred for 1 hour at −20° C. 2.3 g of 2-(4-cyanophenoxy)-1-methylethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus obtaining 0.6 g of the desired product in the form of a white powder (yield: 12%).

Synthesis Example 5

Synthesis of
$N^2$-tert-butoxycarbonyl-$N^1$-(2-phenylthioethyl)-L-valinamide (Compound No. 551)

1 g of N-methylpiperidine was added to a solution containing 2.1 g of N-tert-butoxycarbonyl-L-valine dissolved in 40 mL of methylene chloride, at −20° C. After the mixture was stirred for 10 minutes at the same temperature, 1.3 g of isobutyl chloroformate was added to the mixture, and stirred for 1 hour at −20° C. 1.5 g of 2-phenylthioethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus obtaining 0.4 g of the desired product in the form of cream yellow grains (yield: 12%).

SYNTHESIS EXAMPLE 6

Synthesis of
$N^2$-tert-butoxycarbonyl-$N^1$-[1-methyl-2-(4-nitrophenoxy)propyl]-L-valinamide
(Compound No. 606)

0.5 g of N-methylpiperidine was added to a solution containing 1 g of N-tert-butoxycarbonyl-L-valine dissolved in 40 mL of methylene chloride, at −20° C. After the mixture was stirred for 15 minutes at the same temperature, 0.7 g of isobutyl chloroformate was added to the mixture, and stirred for 1 hour at −20° C. 1 g of 1-methyl-2-(4-nitrophenoxy)propylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue, which was an oily substance, was purified by column chromatography on silica gel, thus obtaining 1.1 g of the desired product in the form of yellow viscous liquid (yield: 56%).

SYNTHESIS EXAMPLE 7

Synthesis of
N²-tert-butoxycarbonyl-N¹-[2-(3,5-dimethoxyphenoxy)-1-methylethyl]-L-valinamide (Compound No. 22)

0.5 g of N-methylpiperidine was added to a solution containing 1.0 g of N-tert-butoxycarbonyl-L-valine dissolved in 100 mL of methylene chloride, at −20° C. After the mixture was stirred for 10 minutes at the same temperature, 0.7 g of isobutyl chloroformate was added to the mixture at −40° C., and stirred for 1 hour at −20° C. 1 g of 2-(3,5-cyanophenoxy)-1-methylamine was added to this mixture at −60° C., and then the reaction mixture was allowed to sit and warm naturally to room temperature while being stirred, and was stirred for 15 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue, which was a crude crystal, was purified by column chromatography on silica gel, thus obtaining 1.3 g of the desired product in the form of white powder (yield: 64%).

SYNTHESIS EXAMPLE 8

Synthesis of
N²-tert-butoxycarbonyl-N¹-[1-methyl-2-(2,4,6-trichlorophenoxy)ethyl]-L-valinamide
(Compound No. 25)

1.7 g of N-methylpiperidine was added to a solution containing 3.8 g of N-tert-butoxycarbonyl-L-valine dissolved in 80 mL of methylene chloride, at −20° C. After the mixture was stirred for 15 minutes at the same temperature, 2.4 g of isobutyl chloroformate was added to the mixture, and stirred for 1 hour at −20° C. 4.5 g of 1-methyl-2-(2,4,6-trichlorophenoxy)ethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus obtaining 4.6 g of the desired product in the form of a colorless needle crystal (yield: 58%).

SYNTHESIS EXAMPLE 9

Synthesis of
N²-isopropoxycarbonyl-N¹-[1-methyl-2-(4-nitrophenoxy)ethyl]-L-valinamide
(Compound No. 45)

1.2 g of N-methylpiperidine was added to a solution containing 2.5 g of N-isopropoxycarbonyl-L-valine dissolved in 100 ml of methylene chloride, at −20° C. After the mixture was stirred for 10 minutes at the same temperature, 1.7 g of isobutyl chloroformate was added to the mixture, and stirred for 1 hour at −20° C. 2.2 g of 2-(4-nitrophenoxy)-1-methylethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus obtaining 0.3 g of the desired product in the form of a yellow vitrified substance (yield: 6%).

| ¹H-NMR: (CDCl₃, δ) | |
|---|---|
| 1.16–1.33 | (6H, m) |
| 1.43–1.36 | (9H, m) |
| 2.56 | (1H, m) |
| 4.01 | (2H, m) |
| 4.00–5.33 | (3H, m) |
| 6.17 | (1H, d) |
| 6.87 | (2H, d) |
| 8.06 | (2H, d) |

SYNTHESIS EXAMPLE 10

Synthesis of
N¹-[2-(4-cyanophenoxy)-1-methylethyl]-N²-cyclohexyloxycarbonyl-L-valinamide
(Compound No. 97)

0.8 g of N-methylpiperidine was added to a solution containing 2.0 g of N-cyclohexyloxycarbonyl-L-valine dissolved in 150 ml of methylene chloride, at −20° C. After the mixture was stirred for 10 minutes at the same temperature, 1.1 g of isobutyl chloroformate was added to the mixture, and stirred for 1 hour at −20° C. 1.5 g of 2-(4-cyanophenoxy)-1-methylethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus obtaining 0.5 g of the desired product in the form of light brown powder (yield: 16%).

SYNTHESIS EXAMPLE 11

Synthesis of
N¹-[1-methyl-2-(4-trifluoromethylphenoxy)ethyl]-N²-phenoxycarbonyl-L-valinamide
(Compound No. 114)

1.6 g of N-methylpiperidine was added to a solution containing 4.0 g of N-phenoxycarbonyl-L-valine dissolved in 80 ml of methylene chloride, at −20° C. After the mixture was stirred for 15 minutes at the same temperature, 2.2 g of isobutyl chloroformate was added to the mixture, and stirred for 1 hour at −20° C. 3.5 g of 1-methyl-2-(4-trifluoromethylphenoxy)ethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus obtaining 2.8 g of the desired product in the form of a white crystal (yield: 40%).

SYNTHESIS EXAMPLE 12

Synthesis of
$N^1$-[1-methyl-2-(4-trifluoromethoxyphenoxy)ethyl]-$N^2$-phenoxycarbonyl-L-valinamide
(Compound No. 115)

1.7 g of N-methylpiperidine was added to a solution containing 4.0 g of N-phenoxycarbonyl-L-valine dissolved in 80 ml of methylene chloride, at −20° C. After the mixture was stirred for 15 minutes at the same temperature, 2.3 g of isobutyl chloroformate was added to the mixture, and stirred for 1 hour at −20° C.

4.0 g of 1-methyl-2-(4-trifluoromethoxyphenoxy)ethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus obtaining 3.4 g of the desired product in the form of a white crystal (yield: 45%).

SYNTHESIS EXAMPLE 3

Synthesis of
$N^1$-[2-(4-cyanophenoxy)-1-methylethyl]-$N^2$-phenoxycarbonyl-L-valinamide
(Compound Nos. 116 and 117)

1.8 g of N-methylpiperidine was added to a solution containing 4.2 g of N-phenoxycarbonyl-L-valine dissolved in 100 ml of methylene chloride, at −20° C. After the mixture was stirred for 10 minutes at the same temperature, 2.4 g of isobutyl chloroformate was added to the mixture, and stirred for 1 hour at −20° C. 3.1 g of 2-(4-cyanophenoxy)-1-methylethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus obtaining 1.0 g of a white powder. 0.6 g of the obtained white powder was purified using high pressure liquid chromatography (hereinafter, referred to as "HPLC") (YMC-063-15, hexane/ethyl acetate=55/45) to separate two fractions. The ingredient of the first fraction possessing a short retention time was 0.3 g of a white powder (yield: 7%) possessing 145° to 147° C. of melting point and the ingredient of the second fraction possessing a long retention time was 0.3 g of a white powder (yield: 7%) possessing a melting point of 166° to 170° C. of melting point.

SYNTHESIS EXAMPLE 14

Synthesis of
$N^2$-[2-(4-cyanophenoxy)-1-methylethyl]-$N^2$-(3-methoxyphenoxycarbonyl)-L-valinamide
(Compound No. 166)

1.0 g of N-methylmorpholine was added to a solution containing 1.5 g of $N^1$-[2-(4-cyanophenoxy)-1-methylethyl]-L-valinamide hydrochloride dissolved in 100 ml of methylene chloride, at −20° C. After 0.9 g of 3-methoxyphenyl chloroformate was added to the mixture at −20° C., the reaction mixture was allowed to sit and warm naturally to room temperature while being stirred, and was stirred for 2 hours at room temperature. Water was subsequently added to the reaction mixture. After the methylene chloride layer was washed with water, the organic layer was dried over anhydrous magnesium sulfate and the methylene chloride was removed under reduced pressure. The residue was purified by column chromatography on silica gel, thus obtaining 0.25 g of the desired product in the form of a white plated crystal (yield: 12%).

SYNTHESIS EXAMPLE 15

Synthesis of
$N^2$-(2-chloroethoxycarbonyl)-$N^1$-[2-(4-cyanophenoxy)-1-methylethyl]-L-valinamide (Compound No. 184)

0.5 g of N-methylpiperidine was added to a solution containing 1.1 g of N-(2-chloroethoxycarbonyl)-L-valine dissolved in 40 ml of methylene chloride, at −20° C. After the mixture was stirred for 15 minutes at the same temperature, 0.7 g of isobutyl chloroformate was added to the mixture at −40° C., and stirred for 1 hour at −20° C. 0.9 g of 2-(4-cyanophenoxy)-1-methylethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue, which was an oily substance, was purified by column chromatography on silica gel, thus obtaining 1.0 g of the desired product in the form of colorless grains (yield: 52%).

SYNTHESIS EXAMPLE 16

Synthesis of
$N^1$-[2-(4-cyanophenoxy)-1-methylethyl]-$N^2$-(4-methylbenzyloxycarbonyl)-L-valinamide
(Compound No. 195)

0.6 g of N-methylpiperidine was added to a solution containing 1.5 g of N-(4-methylbenzyloxycarbonyl)-L-valine dissolved in 100 ml of methylene chloride, at −20° C. After the mixture was stirred for 10 minutes at the same temperature, 0.8 g of isobutyl chloroformate was added to the mixture, and stirred for 1 hour at −20° C. 1.0 g of 2-(4-cyanophenoxy)-1-methylethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue, which was a crude crystal, was purified by column chromatography on silica gel, thus obtaining 0.6 g of the desired product in the form of light white powder (yield: 28%).

SYNTHESIS EXAMPLE 17

Synthesis of
$N^1$-[2-(4-cyanophenoxy)-1-methylethyl]-$N^2$-
phenoxythiocarbonyl-L-valinamide
(Compound No. 208)

0.4 g of N-methylmorpholine was added to a suspension containing 1.1 g of $N^1$-[2-(4-cyanophenoxy)-1-methylethyl]-L-valinamide suspended in 40 ml of methylene chloride, at −15° C. After 0.7 g of phenyl chlorothionoformate was added to the mixture at −15° C., the reaction mixture was allowed to sit and warm naturally to room temperature while being stirred, and was stirred for 15 hours at room temperature. Water was subsequently added to the reaction mixture. After the methylene chloride layer was washed with water, the organic layer was dried over anhydrous magnesium sulfate and the methylene chloride was removed under reduced pressure. The residue was purified by column chromatography on silica gel, thus obtaining 1.2 g of the desired product in the form of a yellow glutinous substance (yield: 75%).

| $^1$H-NMR: (CDCl$_3$, δ) | |
|---|---|
| 1.05 | (6H, m) |
| 1.35 | (3H, m) |
| 2.30 | (1H, m) |
| 4.00 | (2H, m) |
| 4.44 | (1H, m) |
| 4.54 | (1H, m) |
| 6.16, 6.25 | (1H, d) |
| 7.26 | (9H, m) |
| 7.51 | (1H, br) |

SYNTHESIS EXAMPLE 18

Synthesis of
$N^1$-[2-(4-cyanophenoxy)-1-methylethyl]-$N^2$-
(phenylthio)thiocarbonyl-L-valinamide
(Compound No. 211)

0.5 g of N-methylmorpholine was added to a suspension containing 1.4 g of $N^1$-[2-(4-cyanophenoxy)-1-methylethyl]-L-valinamide suspended in 40 ml of methylene chloride, at −15° C. After 0.9 g of phenyl chlorodithioformate was added to the mixture at −15° C., the reaction mixture was allowed to sit and, warm naturally to room temperature while being stirred, and was stirred for 15 hours at room temperature. Water was subsequently added to the reaction mixture. After the methylene chloride layer was washed with water, the organic layer was dried over anhydrous magnesium sulfate and the methylene chloride was removed under reduced pressure. The residue was purified by column chromatography on silica gel, thus obtaining 1.4 g of the desired product in the form of a yellow glutinous substance (yield: 66%).

| $^1$H-NMR: (CDCl$_3$, δ) | |
|---|---|
| 0.83 | (6H, m) |
| 1.30, 1.32 | (3H, d) |
| 2.13 | (1H, m) |
| 3.96 | (2H, m) |
| 4.35 | (1H, m) |
| 4.78 | (1H, dd) |
| 6.04, 6.13 | (1H, d) |
| 6.93, 6.98 | (2H, d) |
| 7.15, 7.22 | (1H, d) |
| 7.57 | (7H, m) |

SYNTHESIS EXAMPLE 19

Synthesis of
$N^1$-(1-methyl-2-phenylthioethyl)-$N^2$-phenoxycarbonyl-
L-valinamide (Compound No. 212)

1.3 g of N-methylmorpholine was added to a suspension containing 3.0 g of $N^1$-(1-methyl-2-phenylthioethyl)-L-valinamide hydrochloride suspended in 80 ml of methylene chloride, at −15° C. After 1.9 g of phenyl chloroformate was added to the mixture at −15° C., the reaction mixture was allowed to sit and warm naturally to room temperature while being stirred, and was stirred for 15 hours at room temperature. Water was subsequently added to the reaction mixture. After the methylene chloride layer was washed with water, the organic layer was dried over anhydrous magnesium sulfate and the methylene chloride was removed under reduced pressure. The residue was purified by column chromatography on silica gel, thus obtaining 2.3 g of the desired product in the form of a white crystal (yield: 54%).

SYNTHESIS EXAMPLE 20

Synthesis of
$N^1$-[2-(4-chloroanilino)-1-methylethyl]-$N^2$-
isopropoxycarbonyl-L-valinamide
(Compound No. 221)

1.9 g of N-methylpiperidine was added to a solution containing 3.8 g of N-isopropoxycarbonyl-L-valine dissolved in 80 ml of methylene chloride, at −20° C. After the mixture was stirred for 15 minutes at the same temperature, 2.6 g of isobutyl chloroformate was added to the mixture, and stirred for 1 hour at −20° C. 3.5 g of 2-(4-chloroanilino)-1-methylethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus obtaining 3.3 g of the desired product in the form of a white crystal (yield: 47%).

SYNTHESIS EXAMPLE 21

Synthesis of
2-tert-butoxycarbonylamino-N-[2-(4-chlorophenoxy)-
1-methylethyl]-(2S)-butyramide
(Compound No. 233)

2.0 g of N-methylpiperidine was added to a solution containing 4.1 g of (2S)-2-tert-butoxycarbonylaminobutyric acid dissolved in 60 ml of methylene chloride, at −20° C.

After the mixture was stirred for 10 minutes at the same temperature, 2.7 g of isobutyl chloroformate was added to the mixture at −40° C., and stirred for 1 hour at −20° C. 3.7 g of 2-(4-chlorophenoxy)-1-methylethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained crude crystal was purified by column chromatography on silica gel, thus obtaining 5.6 g of the desired product in the form of a colorless glutinous substance (yield: 76%).

SYNTHESIS EXAMPLE 22

Synthesis of
2-tert-butoxycarbonylamino-N-[2-(4-cyanophenoxy)-1-methylethyl]-(2S)-butyramide
(Compound No. 235)

0.5 g of N-methylpiperidine was added to a solution containing 1.0 g of (2S)-2-tert-butoxycarbonylaminobutyric acid dissolved in 40 ml of methylene chloride, at −20° C. After the mixture was stirred for 10 minutes at the same temperature, 0.7 g of isobutyl chloroformate was added to the mixture at −20° C., and stirred for 1 hour at −20° C. 0.9 g of 2-(4-cyanophenoxy)-1-methylethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus obtaining 1.0 g of the desired product in the form of a glutinous substance (yield: 54%).

| $^1$H-NMR: (CDCl$_3$, δ) | |
| --- | --- |
| 0.94 | (3H, t) |
| 1.20–1.50 | (12H, m) |
| 1.69 | (2H, m) |
| 3.83–4.56 | (4H, m) |
| 5.30 | (1H, d) |
| 6.60 | (1H, m) |
| 6.90 | (2H, d) |
| 7.50 | (2H, d) |

SYNTHESIS EXAMPLE 23

Synthesis of
N$^1$-[2-(4-chlorobenzyloxy)-1methylethyl]-N$^2$-isopropoxycarbonyl-L-valinamide
(Compound No. 246)

0.5 g of N-methylpiperidine was added to a solution containing 1 g of N-isopropoxycarbonyl-L-valine dissolved in 40 ml of methylene chloride, at −20° C. After the mixture was stirred for 15 minutes at the same temperature, 0.7 g of isobutyl chloroformate was added to the mixture at −40° C., and stirred for 1 hour at −20° C. 1 g of 2-(4-chlorobenzyloxy)-1-methylethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained oily residue was purified by column chromatography on silica gel, thus obtaining 0.9 g of the desired product in the form of a colorless plated crystal (yield: 48%).

SYNTHESIS EXAMPLE 24

Synthesis of
N$^2$-tert-butoxycarbonyl-N$^1$-[1-methyl-2-(4-methylthiophenoxy)ethyl]-L-valinamide
(Compound No. 327)

3.4 g of N-methylpiperidine was added to a solution containing 7.5 g of N-tert-butoxycarbonyl-L-valine dissolved in 100 ml of methylene chloride, at −20° C. After the mixture was stirred for 10 minutes at the same temperature, 4.7 g of isobutyl chloroformate was added to the mixture, and stirred for 1 hour at −20° C. 6.8 g of 1-methyl-2-(4-methylthiophenoxy)ethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous sodium sulfate and the methylene chloride was removed under reduced pressure. The obtained oily residue was purified by column chromatography on silica gel, thus obtaining 6.2 g of the desired product in the form of a colorless prism-shaped crystal (yield: 46%).

SYNTHESIS EXAMPLE 25

Synthesis of
N$^2$-tert-butoxycarbonyl-N$^1$-[1-methyl-2-(4-methylsulfinylphenoxy)ethyl]-L-valinamide
(Compound No. 328)

1.5 g of m-chloroperbenzoic acid was added to a solution containing 3.0 g of N$^2$-tert-butoxycarbonyl-N$^1$-[1-methyl-2-(4-methylthiophenoxy)ethyl]-L-valinamide dissolved in 60 ml of methylene chloride, at 0° C. After the mixture was stirred for 5 hours at room temperature, the reaction mixture was filtered. The filtrate was washed successively with a saturated aqueous solution of potassium carbonate and water, the organic layer was dried over anhydrous sodium sulfate and the methylene chloride was removed under reduced pressure. The obtained oily residue was purified by column chromatography on silica gel, thus obtaining 1.7 g of the desired product in the form of a colorless crystal (yield: 56%).

SYNTHESIS EXAMPLE 26

Synthesis of
N$^2$-tert-butoxycarbonyl-N$^1$-[1-methyl-2-(4-methylsulfonylphenoxy)ethyl]-L-valinamide
(Compound No. 329)

2.1 g of m-chloroperbenzoic acid was added to a solution containing 2.0 g of N$^2$-tert-butoxycarbonyl-N$^1$-[1-methyl-2-

(4-methylthiophenoxy)ethyl]-L-valinamide dissolved in 50 ml of methylene chloride, at 0° C. After the mixture was stirred for 8 hours at a reflux temperature, the reaction mixture was allowed to sit and cool naturally to room temperature and filtered. The filtrate was washed successively with a saturated aqueous solution of potassium carbonate and water, the organic layer was dried over anhydrous sodium sulfate and the methylene chloride was removed under reduced pressure. The obtained residue was purified by column chromatography on silica gel, thus obtaining 1.3 g of the desired product in the form of a colorless prism-shaped crystal (yield: 60%).

SYNTHESIS EXAMPLE 27

Synthesis of
$N^1$-[2-(4-fluorophenylsulfinyl)-1-methylethyl]-$N^2$-isopropoxycarbonyl-L-valinamide
(Compound No. 354)

1.3 g of m-chloroperbenzoic acid was added to a solution containing 2.5 g of $N^1$-[2-(4-fluorophenylthio)-1-methylethyl]-$N^2$-isopropoxycarbonyl-L-valinamide dissolved in 50 ml of methylene chloride, at 0° C. After the mixture was stirred for 5 hours at room temperature, the reaction mixture was filtered. The filtrate was washed successively with a saturated aqueous solution of potassium carbonate and water, the organic layer was dried over anhydrous sodium sulfate and the methylene chloride was removed under reduced pressure. The obtained residue was purified by column chromatography on silica gel, thus obtaining 1.8 g of the desired product in the form of a colorless prism-shaped crystal (yield: 69%).

SYNTHESIS EXAMPLE 28

Synthesis of
$N^1$-[2-(4-fluorophenylsulfonyl)-1-methylethyl]-$N^2$-isopropoxycarbonyl-L-valinamide
(Compound No. 355)

3.4 g of m-chloroperbenzoic acid was added to a solution containing 2.2 g of $N^1$-[2-(4-fluorophenylthio)-1-methylethyl]-$N^2$-isopropoxycarbonyl-L-valinamide dissolved in 50 ml of methylene chloride, at 0° C. After the mixture was stirred for 8 hours at a reflux temperature, the reaction mixture was allowed to sit and cool to room temperature, and then filtered. The filtrate was washed successively with a saturated aqueous solution of potassium carbonate and water, the organic layer was dried over anhydrous sodium sulfate and the methylene chloride was removed under reduced pressure. The obtained residue was purified by column chromatography on silica gel, thus obtaining 2.0 g of the desired product in the form of a white crystal (yield: 83%).

SYNTHESIS EXAMPLE 29

Synthesis of
$N^2$-isopropoxycarbonyl-$N^1$-[1-methyl-2-(2-methylphenylthio)ethyl]-L-valinamide
(Compound No. 367)

1.9 g of N-methylpiperidine was added to a solution containing 3.9 g of N-isopropoxycarbonyl-L-valine dissolved in 80 ml of methylene chloride, at −20° C. After the mixture was stirred for 10 minutes at the same temperature, 2.6 g of isobutyl chloroformate was added to the mixture, and stirred for 1 hour at −20° C. 3.5 g of 1-methyl-2-(2-methylphenylthio)ethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous sodium sulfate and the methylene chloride was removed under reduced pressure. The residue was purified by column chromatography on silica gel, thus obtaining 3.6 g of the desired product in the form of a white crystal (yield: 51%).

SYNTHESIS EXAMPLE 30

Synthesis of
$N^1$-[2-(4-cyanophenoxy)-1-methylethyl]-$N^2$-(3-tetrahydrofuranyl)oxycarbonyl-L-valinamide
(Compound No. 376)

1.0 g of N-methylmorpholine, and subsequently 0.7 g of 3-tetrahydrofuranyl chloroformate were added to a suspension containing 1.5 g of $N^1$-[2-(4-cyanophenoxy)-1-methylethyl]-L-valinamide hydrochloride suspended in 100 ml of methylene chloride at −20° C. The mixture was allowed to sit and warm naturally to room temperature and stirred for 2 hours at room temperature. Water was subsequently added to the reaction mixture. After the dichloromethane layer was washed with water, the organic layer was dried over anhydrous magnesium sulfate and then the methylene chloride was removed under reduced pressure. The residue was purified by column chromatography on silica gel, thus obtaining 1.1 g of the desired product in the form of white powder (yield: 61%).

SYNTHESIS EXAMPLE 31

Synthesis of
$N^1$-[2-(4-cyanophenoxy)-1-methylethyl]-$N^2$-(3-methylcyclohexyloxycarbonyl)-L-valinamid
(Compound No. 379)

0.4 g of N-methylmorpholine, and subsequently 0.8 g of 3-methylcyclohexyl chloroformate were added to a suspension containing 1.0 g of $N^1$-[2-(4-cyanophenoxy)-1-methylethyl]-L-valinamide suspended in 50 ml of methylene chloride at −15° C. The mixture was allowed to sit and warm naturally to room temperature and stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus obtaining 1.2 g of the desired product in the form of a white crystal (yield: 80% ).

SYNTHESIS EXAMPLE 32

Synthesis of
$N^1$-[2-(4-cyanophenoxy)-1-methylethyl]-$N^2$-propargyloxycarbonyl-L-valinamide
(Compound No. 381)

0.2 g of N-methylmorpholine, and subsequently 0.2 g of propargyl chloroformate were added to a suspension containing 0.5 g of $N^1$-[2-(4-cyanophenoxy)-1-methylethyl]-L- valinamide suspended in 30 ml of methylene chloride at −15° C. The mixture was allowed to sit and warm naturally to room temperature and stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus obtaining 0.5 g of the desired product in the form of white powder (yield: 78%).

SYNTHESIS EXAMPLE 33

Synthesis of
$N^1$-[2-(4-cyanophenoxy)-1-methylethyl]-$N^2$-(2-methoxy-1-methylethyl)oxycarbonyl-L-valinamide
(Compound No. 383)

1.0 g of N-methylmorpholine, and subsequently 0.7 g of 2-methoxy-1-methylethyl chloroformate were added to a suspension containing 1.5 g of $N^1$-[2-(4-cyanophenoxy)-1-methylethyl]-L-valinamide suspended in 150 ml of methylene chloride at −20° C. The mixture was allowed to sit and warm naturally to room temperature and stirred for 2 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus obtaining 0.37 g of the desired product in the form of a white plated crystal (yield: 20%).

SYNTHESIS EXAMPLE 34

Synthesis of
$N^1$-[2-(4-fluoro-N-methylanilino)-1-methylethyl]-$N^2$-phenoxycarbonyl-L-valinamide
(Compound No. 391)

1.6 g of N-methylpiperidine was added to a solution containing 3.9 g of N-phenoxycarbonyl-L-valine dissolved in 80 ml of methylene chloride, at −20° C. After the mixture was stirred for 10 minutes at the same temperature, 2.2 g of isobutyl chloroformate was added to the mixture, and stirred for 1 hour at −20° C. 3.0 g of 2-(4-fluoro-N-methylanilino)-1-methylethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous sodium sulfate and the methylene chloride was removed under reduced pressure. The residue was purified by column chromatography on silica gel, thus obtaining 1.2 g of the desired product in the form of a white crystal (yield: 19%).

SYNTHESIS EXAMPLE 35

Synthesis of
$N^2$-(4-chlorophenoxycarbonyl)-$N^1$-[2-(4-cyanophenoxy-1-methylethyl]-L-valinamide
(Compound Nos. 395 and 396)

1.7 g of N-methylpiperidine was added to a solution containing 4.7 g of N-(4-chlorophenoxycarbonyl)-L-valine dissolved in 250 ml of methylene chloride, at −20° C. After the mixture was stirred for 10 minutes at the same temperature, 2.3 g of isobutyl chloroformate was added to the mixture, and stirred for 1 hour at −20° C. 3.0 g of 2-(4-cyanophenoxy)-1-methylethylamine was added to this mixture at −60° C., and then the reaction mixture was allowed to sit and warm naturally to room temperature while being stirred, and was stirred for 15 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained crude crystal was purified by column chromatography on silica gel, thus obtaining 0.4 g of the desired product in the form of white powder. In addition, the powder was purified by HPLC (YMC-063-15, hexane/ethyl acetate=55/45) to separate two fractions. One fraction possessing a short retention time was 0.17 g of white powder possessing 137°–140° C. of melting point (yield: 2%), and another fraction possessing a long retention time was 0.17 g of white powder possessing a melting point of 174°–179° C. (yield: 2%).

SYNTHESIS EXAMPLE 36

Synthesis of
$N^1$-[2-(4-cyanophenoxy)-1-methylethyl]-$N^2$-(2-nitrophenoxycarbonyl-L-valinamide
(Compound No. 400)

1.3g of N-methylmorpholine, and subsequently 2.5 g of 2nitrophenyl chloroformate were added to a suspension containing 3.4 g of $N^1$-[2-(4-cyanophenoxy)-1-methylethyl]-L-valinamide suspended in 100 ml of methylene chloride at −20° C. The mixture was allowed to sit and warm naturally to room temperature and stirred for 2 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus obtaining 1.0 g of the desired product in the form of a yellow plated crystal (yield: 18%).

SYNTHESIS EXAMPLE 37

Synthesis of
$N^1$-[2-(4-cyanophenoxy)-1-methylethyl]-$N^2$-(4-fluorophenoxycarbonyl)-L-valinamide
(Compound. No. 401)

1.2 g of N-methylpiperidine was added to a solution containing 3.0 g of N-(4-fluorophenoxycarbonyl)-L-valine dissolved in 80 ml of methylene chloride, at −20° C. After the mixture was stirred for 15 minutes at the same temperature, 1.6 g of isobutyl chloroformate was added to the mixture, and stirred for 1 hour at −20° C. 2.3 g of (−)-2-(4-cyanophenoxy)-1-methylethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained crude crystal was purified by column chromatography on silica gel, thus obtaining 1.1 g of the desired product in the form of a white crystal (yield: 23% ).

SYNTHESIS EXAMPLE 38

Synthesis of
$N^1$-[2-(4-cyanophenoxy)-1-methylethyl]-$N^2$-(3,4-dimethylphenoxycarbonyl)-L-valinamide
(Compound No. 403)

0.6 g of N-methylmorpholine, and subsequently 1.2 g of 3,4-dimethylphenyl chloroformate were added to a suspension containing 1.5 g of $N^1$-[2-(4-cyanophenoxy)-1-methylethyl]-L-valinamide suspended in 50 ml of methylene chloride at −15° C. The mixture was allowed to sit and warm naturally to room temperature and stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus obtaining 1.7 g of the desired product in the form of a white crystal (yield: 74%).

SYNTHESIS EXAMPLE 39

Synthesis of
$N^2$-tert-butoxycarbonyl-$N^1$-[2-(2-pyridyloxy)-1-methylethyl]-L-valinamide (Compound No. 409)

2.0 g of N-methylpiperidine was added to a solution containing 4.3 g of N-tert-butoxycarbonyl-L-valine dissolved in 80 ml of methylene chloride, at −20° C. After the mixture was stirred for 10 minutes at the same temperature, 2.7 g of isobutyl chloroformate was added to the mixture at −40° C., and stirred for 1 hour at −20° C. 3.3 g of 2-(2-pyridyloxy)-1-methylethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous sodium sulfate and the methylene chloride was removed under reduced pressure. The obtained crude crystal was purified by column chromatography on silica gel, thus obtaining 2.0 g of the desired product in the form of colorless grains (yield: 28%).

SYNTHESIS EXAMPLE 40

Synthesis of
$N^1$-[2-(5-chloro-2-pyridyloxy)-1-methylethyl]-$N^2$-isopropyloxycarbonyl-L-valinamide
(Compound No. 412)

0.8 g of N-methylmorpholine, and subsequently 0.5 g of isopropyl chloroformate were added to a suspension containing 1.4 g of $N^1$-[2-(5-chloro-2-pyridyloxy)-1-methylethyl]-L-valinamide hydrochloride suspended in 50 ml of methylene chloride at −15° C. The mixture was allowed to sit and warm naturally to room temperature and stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus obtaining 0.6 g of the desired product in the form of colorless grains (yield: 38%).

SYNTHESIS EXAMPLE 41

Synthesis of
$N^1$-[2-(5-chloro-2-pyridyloxy)-1-methylethyl]-$N^2$-phenoxycarbonyl-L-valinamide
(Compound No. 413)

0.8 g of N-methylmorpholine, and subsequently 0.7 g of phenyl chloroformate were added to a suspension containing 1.4 g of $N^1$-[2-(5-chloro-2-pyridyloxy)-1-methylethyl]-L-valinamide hydrochloride suspended in 50 ml of methylene chloride at −15° C. The mixture was allowed to sit and warm naturally to room temperature and stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus obtaining 0.6 g of the desired product in the form of colorless grains (yield: 34%).

SYNTHESIS EXAMPLE 42

Synthesis of
$N^1$-[2-(4-fluoro-N-methylanilino)-1-methylethyl]-$N^2$-phenoxycarbonyl-L-isoleucinamide
(Compound No. 422)

1.9 g of N-methylpiperidine was added to a solution containing 4.8 g of N-phenoxycarbonyl-L-isoleucine dissolved in 80 ml of methylene chloride, at −20° C. After the mixture was stirred for 10 minutes at the same temperature, 2.6 g of isobutyl chloroformate was added to the mixture, and stirred for 1 hour at −20° C. 3.5 g of 2-(4-fluoro-N-methylanilino)-1-methylethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous sodium sulfate and the methylene chloride was removed under reduced pressure. The obtained crude crystal was purified by column chromatography on silica gel, thus obtaining 1.1 g of the desired product in the form of a white crystal (yield: 13%).

SYNTHESIS EXAMPLE 43

Synthesis of
$N^2$-(ethylthio)carbonyl-$N^1$-[1-methyl-2-(4-nitrophenoxy)ethyl]-L-valinamide
(Compound No. 432)

0.3 g of N-methylmorpholine, and subsequently 0.4 g of ethyl chlorothioformate were added to a suspension containing 0.9 g of $N^1$-[1-methyl-2-(4-nitrophenoxy)ethyl]-L-valinamide suspended in 50 ml of methylene chloride at −15° C. The mixture was allowed to sit and warm naturally to room temperature and stirred for 15 hours at room temperature. Water was subsequently added to the reaction mixture. After the methylene chloride layer was washed with water, the organic layer was dried over anhydrous

SYNTHESIS EXAMPLE 44

Synthesis of
$N^2$-tert-butoxycarbonyl-$N^1$-[2-(4-cyanophenoxy)-1-methylethyl]-L-leucinamide (Compound No. 455)

1.5 g of N-methylpiperidine was added to a solution containing 3.4 g of N-tert-butoxycarbonyl-L-leucine dissolved in 60 ml of methylene chloride, at −20° C. After the mixture was stirred for 10 minutes at the same temperature, 2.0 g of isobutyl chloroformate was added to the mixture at −40° C., and stirred for 1 hour at −20° C. 2.6 g of 2-(4-cyanophenoxy)-1-methylethylamine was added to this mixture at −60° C., and then the reaction mixture was allowed to sit and warm naturally to room temperature while being stirred, and was stirred for 15 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained crude crystal was purified by column chromatography on silica gel, thus obtaining 5.1 g of the desired product in the form of a colorless glutinous substance (yield: 86%).

| $^1$H-NMR: (CDCl$_3$, δ) | |
|---|---|
| 0.92 | (6H, m) |
| 1.28, 1.32 | (3H, d) |
| 1.39, 1.43 | (9H, s) |
| 1.46, 1.65 | (2H, m) |
| 1.65 | (1H, m) |
| 3.98 | (2H, m) |
| 4.06 | (1H, m) |
| 4.35 | (1H, m) |
| 4.91 | (1H, br) |
| 6.46 | (1H, br) |
| 6.97 | (2H, d) |
| 7.57 | (2H, dd) |

SYNTHESIS EXAMPLE 45

Synthesis of
$N^2$-tert-butoxycarbonyl-$N^1$-[2-(4-cyanophenoxy)-1-methylethyl]-L-tert-leucinamide
(Compound No. 457)

1.7 g of N-methylpiperidine was added to a solution containing 4 g of N-tert-butoxycarbonyl-L-tert-leucine dissolved in 50 ml of methylene chloride, at −20° C. After the mixture was stirred for 10 minutes at the same temperature, 2.4 g of isobutyl chloroformate was added to the mixture at −40° C., and stirred for 1 hour at −20° C. 3.1 g of 2-(4-cyanophenoxy)-1-methylethylamine was added to this mixture at −60° C., and then the reaction mixture was allowed to sit and warm naturally to room temperature while being stirred, and was stirred for hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained crude crystal was purified by column chromatography on silica gel, thus obtaining 3.9 g of the desired product in the form of a colorless amorphous substance (yield: 58%).

SYNTHESIS EXAMPLE 46

Synthesis of
2-tert-butoxycarbonylamino-3-methyl-N-[2-(4-cyanophenoxy)-1-methylethyl]-3-butenic acid amide
(Compound No. 460)

0.5 g of N-methylpiperidine was added to a solution containing 1.1 g of 2-tert-butoxycarbonylamino-3-methyl-3-butenic acid dissolved in 40 ml of methylene chloride, at −20° C. After the mixture was stirred for 10 minutes at the same temperature, 0.7 g of isobutyl chloroformate was added to the mixture at −40° C., and stirred for 1 hour at −20° C. 1.9 g of 2-(4-cyanophenoxy)-1-methylethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained crude crystal was purified by column chromatography on silica gel, thus obtaining 0.3 g of the desired product in the form of a colorless glutinous substance (yield: 32%).

SYNTHESIS EXAMPLE 47

Synthesis of
N-[2-(4-cyanophenoxy)-1-methylethyl]-2-isopropoxycarbonylaminocyclopentylacetic acid amide (Compound No. 462)

0.4 g of N-methylmorpholine, and subsequently 0.5 g of isopropyl chloroformate were added to a suspension containing 1.2 g of 2-amino-N-[2-(4-cyanophenoxy)-1-methylethyl]cyclopentylacetic acid amide suspended in 40 ml of methylene chloride at −15° C. The mixture was allowed to sit and warm naturally to room temperature and stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus obtaining 1.4 g of the desired product in the form of a colorless plated crystal (yield: 90%).

SYNTHESIS EXAMPLE 48

Synthesis of
$N^1$-[2-(4-cyanophenoxy)-1-methylethyl]-$N^2$-phenoxycarbonyl-L-norvalinamide
(Compound No. 465)

0.5 g of N-methylmorpholine, and subsequently 0.8 g of phenyl chloroformate were added to a suspension containing 1.4 g of $N^1$-[2-(4-cyanophenoxy)-1-methylethyl]-L-norvalinamide suspended in 40 ml of methylene chloride at −15° C. The mixture was allowed to sit and warm naturally to room temperature and stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus obtaining 1.1 g of the desired product in the form of a colorless plated crystal (yield: 57%).

SYNTHESIS EXAMPLE 49

Synthesis of
$N^1$-[2-(4-cyanophenoxy)-1-methylethyl]-$N^2$-phenoxycarbonyl-L-leucinamide
(Compound No. 466)

0.5 g of N-methylmorpholine, and subsequently 0.8 g of phenyl chloroformate were added to a suspension containing 1.5 g of $N^1$-[2-(4-cyanophenoxy)-1-methylethyl]-L-leucinamide suspended in 40 ml of methylene chloride at −15° C. The mixture was allowed to sit and warm naturally to room temperature and stirred for 15 hours at room temperature. Water was subsequently added to the reaction mixture. After the methylene chloride layer was washed with water, the organic layer was dried over anhydrous magnesium sulfate and then the methylene chloride was removed tinder reduced pressure. The residue was purified by column chromatography on silica gel, thus obtaining 1.5 g of the desired product in the form of colorless powder (yield: 73%)

SYNTHESIS EXAMPLE 50

Synthesis of
2-(4-chlorophenoxycarbonylamino)-N-[2-(4-cyanophenoxy)-1-methylethyl]cyclopentylacetic acid amide (Compound No. 471)

0.4 g of N-methylmorpholine, and subsequently 0.8 g of 4-chlorophenyl chloroformate were added to a suspension containing 1.2 g of 2-amino-N-[2-(4-cyanophenoxy)-1-methylethyl]cyclopentylacetic acid amide suspended in 40 ml of methylene chloride at −15° C. The mixture was allowed to sit and warm naturally to room temperature and stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus obtaining 0.6 g of the desired product in the form of colorless grains (yield: 30%).

SYNTHESIS EXAMPLE 51

Synthesis of
$N^2$-benzyloxycarbonyl-$N^1$-[2-(4-cyanophenoxy)-1-methylethyl]-(4-chlorophenyl)glycinamide
(Compound No. 475)

0.4 g of N-methyhnorpholine, and subsequently 0.6 g of benzyl chloroformate were added to a suspension containing 1.3 g of $N^1$-[2-(4-cyanophenoxy)-1-methylethyl]-(4-chlorophenyl)glycinamide suspended in 40 ml of methylene chloride at −15° C. The mixture was allowed to sit and warm naturally to room temperature and stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus obtaining 1.2 g of the desired product in the form of colorless grains (yield: 70%).

SYNTHESIS EXAMPLE 52

Synthesis of
$N^2$-(1-cyano-1-methylethoxycarbonyl)-$N^1$-[2-(4-cyanophenoxy)-1-methylethyl]-L-valinamide
(Compound No. 476)

0.5 g of N-methylmorpholine, and subsequently 0.4 g of 1-cyano-1-methylethyl chloroformate were added to a suspension containing 0.7 g of $N^1$-[2-(4-cyanophenoxy)-1-methylethyl]-L-valinamide hydrochloride suspended in 50 ml of methylene chloride at −20° C. The mixture was allowed to sit and warm naturally to room temperature and stirred for 3 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus obtaining 0.6 g of the desired product in the form of colorless grains (yield: 71%).

SYNTHESIS EXAMPLE 53

Synthesis of
$N^2$-(2-chlorocyclohexyloxycarbonyl)-$N^1$-[2-(4-cyanophenoxy)-1-methylethyl]-L-valinamide
(Compound No. 477)

0.4 g of N-methylmorpholine, and subsequently 0.9 g of 2-chlorocyclohexyl chloroformate were added to a suspension containing 1.0 g of $N^1$-[2-(4-cyanophenoxy)-1-methylethyl]-L-valinamide hydrochloride suspended in 50 ml of methylene chloride at −20° C. The mixture was allowed to sit and warm naturally to room temperature and stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus obtaining 1.1 g of the desired product in the form of a white crystal (yield: 71%).

SYNTHESIS EXAMPLE 54

Synthesis of
$N^2$-tert-butoxycarbonyl-$N^1$-[2-(3-chloro-5-trifluoromethyl-2-pyridyloxy)-1-methylethyl]-L-valinamide (Compound No. 479)

2.0 g of N-methylpiperidine was added to a solution containing 5.6 g of N-tert-butoxycarbonyl-L-valine dissolved in 100 ml of methylene chloride, at −20° C. After the mixture was stirred for 10 minutes at the same temperature, 2.7 g of isobutyl chloroformate was added to the mixture at −40° C., and stirred for 1 hour at −20° C. 1.5 g of 2-(3-chloro-5-trifluoromethyl-2-pyridyloxy)-1-methylethylamine was added to this mixture at −60° C., and then the reaction mixture was allowed to sit and warm naturally to room temperature, with stirring, and stirred for 20 hours at room temperature. Water was subsequently added to the reaction mixture. After the methylene chloride layer was washed successively with a 5% aqueous solution of sodium bicarbonate and water, the organic layer was dried over anhydrous sodium sulfate and the methylene chloride was removed under reduced pressure. The obtained crude crystal was purified by column chromatography on silica gel, thus obtaining 7.0 g of the desired product in the form of colorless grains (yield: 77%).

SYNTHESIS EXAMPLE 55

Synthesis of
$N^1$-[1-(5-chloro-6-ethyl-4-pyrimidinyloxy)-2-propyl]-$N^2$-isopropoxycarbonyl-L-valinamide
(Compound No. 481)

0.34 g of N-methylpiperidine was added to a solution containing 0.7 g of N-isopropoxycarbonyl-L-valine dissolved in 50 ml of methylene chloride, at −20° C. After the mixture was stirred for 10 minutes at the same temperature, 0.47 g of isobutyl chloroformate was added to the mixture, and stirred for 1 hour at −20° C. 0.74 g of 1-(5-chloro-6-ethyl-4-pyrimidinyloxy)-2-propylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained crude crystal was purified by column chromatography on silica gel, thus obtaining 0.6 g of the desired product in the form of a white prism-shaped crystal (yield: 43%).

SYNTHESIS EXAMPLE 56

Synthesis of
N-tert-butoxycarbonyl-L-valyl-N-(4-chlorophenyl)-N-methyl-DL-alaninamide (Compound No. 490)

0.9 g of N-methylpiperidine was added to a solution containing 2.0 g of N-tert-butoxycarbonyl-L-valine dissolved in 40 ml of methylene chloride, at −20° C. After the mixture was stirred for 10 minutes at the same temperature, 1.3 g of isobutyl chloroformate was added to the mixture, and stirred for 1 hour at −20° C. 2.0 g of $N^1$-(4-chlorophenyl)-$N^1$-methyl-DL-alaninamide was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained crude crystal was purified by column chromatography on silica gel, thus obtaining 3.4 g of the desired product in the form of a colorless needle crystal (yield: 87%).

SYNTHESIS EXAMPLE 57

Synthesis of
N-isopropoxycarbonyl-L-isoleucyl-N-(4-cyanophenyl)-D-alaninamide (Compound No. 506)

0.26 g of N-methylpiperidine was added to a solution containing 0.57 g of N-isopropoxycarbonyl-L-isoleucine dissolved in 60 ml of methylene chloride, at −20° C. After the mixture was stirred for 10 minutes at the same temperature, 0.36 g of isobutyl chloroformate was added to the mixture, and stirred for 1 hour at −20° C. 0.5 g of $N^1$-(4-cyanophenyl)-D-alaninamide was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous sodium sulfate and the methylene chloride was removed under reduced pressure. The residue was purified by column chromatography on silica gel, thus obtaining 0.5 g of the desired product in the form of white powder (yield: 49%).

SYNTHESIS EXAMPLE 58

Synthesis of
N-cyclohexyloxycarbonyl-L-valyl-N-(4-cyanophenyl)-D-alaninamide (Compound No. 509)

0.6 g of N-methyhnorpholine, and subsequently 0.6 g of cyclopentyl chloroformate were added to a suspension containing 1.0 g of L-valyl-N-(4-cyanophenyl)alaninamide, hydrochloride suspended in 50 ml of methylene chloride at −20° C. The mixture was allowed to sit and warm naturally to room temperature and stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus obtaining 0.6 g of the desired product in the form of a white crystal (yield: 49% ).

SYNTHESIS EXAMPLE 59

Synthesis of
N-phenoxycarbonyl-L-valyl-N-(4-chlorobenzyl)-DL-alaninamide (Compound No. 516)

0.55 g of N-methyhnorpholine, and subsequently 0.43 g of phenyl chloroformate were added to a suspension containing 0.95 g of L-valyl-N-(4-chlorobenzyl)-DL-alaninamide, hydrochloride suspended in 50 ml of methylene chloride at −15° C. The mixture was allowed to sit and warm naturally to room temperature and stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus obtaining 0.9 g of the desired product in the form of white powder (yield: 75%).

SYNTHESIS EXAMPLE 60

Synthesis of
N-phenoxycarbonyl-L-valyl-DL-alanine phenyl ester (Compound No. 522)

0.24 g of N-methylpiperidine was added to a solution containing 0.57 g of N-phenoxycarbonyl-L-valine dissolved in 40 ml of methylene chloride, at −20° C. After the mixture was stirred for 10 minutes at the same temperature, 0.33 g of isobutyl chloroformate was added to the mixture, and stirred for 1 hour at −20° C. 0.5 g of DL-alanine phenyl ester was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus obtaining 0.2 g of the desired product in the form of white powder (yield: 20%).

SYNTHESIS EXAMPLE 61

Synthesis of
$N^1$-(4-cyanophenyl)-$N^2$-(2-phenoxycarbonylamino)-(2S)-butyryl-D-alaninamide (Compound No. 524)

0.45 g of N-methylpiperidine was added to a solution containing 1.0 g of (2S)-2-phenoxycarbonylaminobutyric acid dissolved in 50 ml of methylene chloride, at −20° C. After the mixture was stirred for 10 minutes at the same temperature, 0.61 g of isobutyl chloroformate was added to the mixture, and stirred for 1 hour at −20° C. 0.85 g of $N^1$-(4-cyanophenyl)-D-alaninamide was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained crude crystal was purified by column chromatography on silica gel, thus obtaining 0.8 g of the desired product in the form of white powder (yield: 45%).

SYNTHESIS EXAMPLE 62

Synthesis of
N-isopropoxycarbonyl-L-valyl-N-(4-cyanophenyl)-glycinamide (Compound No. 526)

0.3 g of N-methylpiperidine was added to a solution containing 0.6 g of N-isopropoxycarbonyl-L-valine dissolved in 40 ml of methylene chloride, at −20° C. After the mixture was stirred for 10 minutes at the same temperature, 0.4 g of isobutyl chloroformate was added to the n-fixture, and stirred for 1 hour at −20° C. 0.5 g of $N^1$-(4-cyanophenyl)glycinamide was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus obtaining 0.5 g of the desired product in the form of colorless powder (yield: 49%).

SYNTHESIS EXAMPLE 63

Synthesis of
$N^2$-tert-butoxycarbonyl-$N^1$-(1,2-dimethyl-2-phenoxyethyl)-L-valinamide (Compound No. 602)

0.6 g of N-methylpiperidine was added to a solution containing 1.3 g of N-tert-butoxycarbonyl-L-valine dissolved in 40 ml of methylene chloride, at −20° C. After the mixture was stirred for 15 minutes at the same temperature, 0.8 g of isobutyl chloroformate was added to the mixture, and stirred for 1 hour at −20° C. 1 g of 1,2-dimethyl-2-phenoxyethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained oily substance was purified by column chromatography on silica gel, thus obtaining 1.3 g of the desired product in the form of a white glutinous substance (yield: 57%).

| $^1$H-NMR: (CDCl$_3$, δ) | |
|---|---|
| 0.8–1.02 | (6H, m) |
| 1.18–1.45 | (15H, m) |
| 2.10 | (1H, m) |
| 3.65–4.45 | (3H, m) |
| 5.18 | (1H, m) |
| 6.38 | (1H, m) |
| 6.72–7.35 | (5H, m) |

SYNTHESIS EXAMPLE 64

Synthesis of
$N^2$-tert-butoxycarbonyl-$N^1$-[2-(4-cyanophenoxy)-1,2-dimethylethyl]-L-valinamide
(Compound No. 607)

0.5 g of N-methylpiperidine was added to a solution containing 1.1 g of N-tert-butoxycarbonyl-L-valine dissolved in 60 ml of methylene chloride, at −20° C. After the mixture was stirred for 10 minutes at the same temperature, 0.7 g of isobutyl chloroformate was added to the mixture, and stirred for 1 hour at −20° C. 1.0 g of 2-(4-cyanophenoxy)-1,2-dimethylethylamine was added to this mixture at −60° C., and then the reaction mixture was allowed to sit and warm naturally to room temperature while being stirred, and was stirred for 20 hours at room temperature. Water was subsequently added to the reaction mixture. After the methylene chloride layer was washed successively with a 5% aqueous solution of sodium bicarbonate and water, the organic layer was dried over anhydrous sodium sulfate and the methylene chloride was removed under reduced pressure. The residue was purified by column chromatography on silica gel, thus obtaining 1.2 g of the desired product in the form of a colorless glassy substance (yield: 61%).

| $^1$H-NMR: (CDCl$_3$, δ) | |
|---|---|
| 0.79–1.03 | (6H, m) |
| 1.15–1.46 | (15H, m) |
| 2.03 | (1H, m) |

-continued

| $^1$H-NMR: (CDCl$_3$, δ) | |
|---|---|
| 3.63–4.72 | (3H, m) |
| 5.06 | (1H, m) |
| 6.30 | (1H, m) |
| 6.83–7.60 | (4H, m) |

SYNTHESIS EXAMPLE 65

Synthesis of
N$^1$-[2-(4-cyanophenoxy)propyl]-N$^2$-phenoxycarbonyl-L-valinamide (Compound No. 750)

0.16 g of N-methylpiperidine was added to a suspension containing 0.25 g of N$^1$-[2-(4-cyanophenoxy)propyl]-L-valinamide hydrochloride suspended in 20 ml of methylene chloride, at −20° C. After the mixture was stirred for 10 minutes at the same temperature, 0.13 g of phenyl chloroformate was added drop by drop to the mixture, and then the reaction mixture was allowed to sit and warm naturally to room temperature while being stirred, and was stirred for 3 hours at room temperature. After the methylene chloride was removed under reduced pressure, the residue was purified by column chromatography on silica gel, thus obtaining 0.2 g of the desired product in the form of a white glutinous substance (yield: 63%).

| $^1$H-NMR: (CDCl$_3$, δ) | |
|---|---|
| 1.00 | (6H, m) |
| 1.23 | (3H, d) |
| 2.13 | (1H, m) |
| 3.31 | (1H, m) |
| 4.00 | (2H, m) |
| 4.49 | (1H, m) |
| 5.93 | (1H, d) |
| 6.52 | (1H, m) |
| 6.80–7.56 | (9H, m) |

The agricultural or horticultural fungicide according to the present invention is a composition containing an amino acid amide derivative represented by Formula [I] as an active ingredient. In the case where the compounds according to the present invention are employed as an agricultural or horticultural fungicide, the compounds acting as the active ingredient can be formulated appropriately, depending on the purpose. The active ingredient is usually diluted in an inert liquid or a solid carrier, and a surfactant or the like is added thereto, if necessary. The mixture is then formulated in a known manner into, for example, a fine powder, a wettable powder, an emulsifiable concentrate, granules, or the like.

Suitable examples of carriers employed in the formulation are solid carriers such as talc, bentonite, clay, kaolin, diatomaceous earth, white carbon, vermiculite, slaked lime, siliceous sand, ammonium sulfate, urea, or the like; and liquid carriers such as isopropyl alcohol, xylene, cyclohexanone, methylnaphthalene, and the like. Illustrative examples of the surfactants and dispersants include salts of dinaphthylmethanesulfonic acid, sulfate esters of alcohol, alkylarylsulfonic acid, and ligninesulfonic acid, polyoxyethylene glycol ethers, polyoxyethylene alkyl aryl ethers, polyoxyethylenesorbitan monoalkylates, and the like. Suitable examples of auxiliary agents include carboxymethylcellulose, and the like. These preparations can be applied directly, or after diluting the preparation to a suitable concentration.

The agricultural or horticultural fungicide according to the present invention can be employed for a number of purposes: for example, treating seeds, spraying of stem and leaf portions, injection into irrigation water, and applying to the soil. The proportion of the active ingredient is selected as needed. When formulated into a fine powder or granules, 0.1% by weight to 20% by weight of the active ingredient is preferred. For an emulsifiable concentrate or wettable powder, 5% by weight to 80% by weight of the active ingredient is adequate.

The rate of application of the agricultural or horticultural fungicide according to the present invention may vary depending on the type of active compound employed, the kind of the pest or disease to be controlled, the nature of occurrence of the pest or disease, the degree of damage, environmental conditions, the form of preparation to be used, and the like. When the agricultural or horticultural fungicide of the present invention is applied directly in the form of fine powder or granules, it is recommended that the rate of application of the active ingredient be suitably chosen within the range of 0.1 g to 5 kg per 10 ares, preferably, in the range of 1 g to I kg per 10 ares. In addition, when the fungicide of the present invention is in the form of a liquid such as an emulsifiable concentrate or a wettable powder, it is recommended that the ratio for application of the active ingredient be suitably chosen within the range of 0.1 ppm to 10,000 ppm, and preferably within the range of 10 ppm to 3,000 ppm.

The compounds according to the present invention in the formulation described above can control plant diseases caused by fungi in the Oomycetes, Ascomycetes, Deuteromycetes, and Basidiomycetes or other pathogenic fungi. The fungi include, but are not limited to, Pseudoperonospora such as cucumber downy mildew (*Pseudoperonospora cubensis*), Phytophthora such as tomato late blight (*Phytophthora infestans*), and Plasmopara such as grape downy mildew (*Plasmopara viticola*).

The agricultural or horticultural fungicide according to the present invention may be employed alone or in combination with other fungicides, insecticides, herbicides, plant growth modifiers, fertilizers or the like.

Next, the representative formulations are illustrated with reference to the following Formulation Examples, wherein all "%" represent "percent by weight".

Formulation Example 1

Fine powder

2% of Compound No. 15, 5% of diatomaceous earth, and 93% of clay were uniformly mixed and ground into a fine powder.

Formulation Example 2

Wettable powder

50% of Compound No. 16, 45% of diatomaceous earth, 2% of sodium dinaphthylmethanedisulfonate, and 3% of sodium ligninsulfonate were uniformly mixed and ground into a wettable powder.

Formulation Example 3

Emulsifiable concentrate

30% of Compound No. 19, 20% of cyclohexanone, 11% of polyoxyethylene alkylaryl ether, 4% of calcium alkylbenzenesulfonate, and 35% of methylnaphthalene were uniformly dissolved, thus obtaining an emulsifiable concentrate.

Formulation Example 4

Granules

5% of Compound No. 101, 2% of sodium lauryl alcohol sulfonate, 5% of sodium lignin sulfonate, 2% of carbomethylcellulose, and 86% of clay were mixed and ground. 20% of water was added to the ground mixture. The resulting mixture was kneaded and formed into granules of 14 mesh to 32 mesh by means of an extrusion granulator, and then dried into the desired granules.

Effects of the Invention

The agricultural or horticultural fungicides according to the present invention exhibit high ability to control the growth or spread of cucumber downy mildew (*Pseudoperonospora cubensis*), tomato late blight (*Phytophthora infestans*), and grape downy mildew (*Plasmopara viticola*), and are effective for potato late blight (*Phytophthora infestans*). In addition, the agricultural or horticultural fungicides according to the present invention not only exhibit the ability to prevent fungal infection, but also exhibit the ability to eliminate pathogenic fungi after it has invaded a host plant. Furthermore, the agricultural or horticultural fungicides of the present invention are also characterized in that they are not harmful chemicals and exhibit excellent characteristics such as systemic action, residual activity, and persistence after rain-fall.

The effects of the compounds according to the present invention are now illustrated with reference to the following Test Examples. Comparative Compound X and Comparative Compound Y employed in the Test Examples are the compounds disclosed as synthesis intermediates for drugs in Japanese Patent Application, First Publication, No. Sho 62-89696. These Comparative Compounds were employed after being formulated in the same manner as the compounds of the present invention to be tested.

Comparative Compound X: $N^2$-tert-butoxycarbonyl-$N^1$-(2-phenoxyethyl)-D-alaninamide Comparative Compound Y: $N^2$-tert-butoxycarbonyl-$N^1$-(2-phenylthioethyl)-D-alaninamide Test Example 1

Test on the Effect of Preventing Infection by Cucumber Downy Mildew (*Pseudoperonospora cubensis*)

Cucumber seeds (variety: "Sagami hanjiro") were sown at a rate of 10 seeds each in a square PVC (polyvinyl chloride) pot, wherein each side is 9 cm wide. The seeds were allowed to grow in a greenhouse, for 7 days, to the cotyledonous stage. A wettable powder prepared as in Formulation Example 2 was diluted with water to a concentration of 500 ppm of the active ingredient, and the aqueous preparation obtained was then applied at a rate of 10 ml per pot to the cucumber seedlings at their cotyledonous stage. After drying in the air, the plant was inoculated with a spore suspension of cucumber downy mildew (*Pseudoperonospora cubensis*) fungi using a spray and then placed in a moist chamber at 22° C. for 24 hours, and then placed in a greenhouse. On the seventh day after the inoculation, the extent of lesion was rated in accordance with the standards of evaluation as shown in Table 15 in order to secure the preventive effects of the compounds according to the present invention. The results of the test are given in Table 16.

TABLE 15

| Standard of evaluation: | Affected area |
|---|---|
| Class A: | No lesions were observed |
| Class B: | Affected area is less than 25% |
| Class C: | Affected area is 25% or more and less than 50% |
| Class D: | Affected area is 50% or more |

TABLE 16

| Compound No. | Evaluation |
|---|---|
| 1 | B |
| 2 | A |
| 4 | A |
| 6 | A |
| 7 | A |
| 8 | B |
| 10 | A |
| 13 | A |
| 14 | B |
| 16 | A |
| 17 | A |
| 18 | B |
| 19 | A |
| 23 | A |
| 24 | B |
| 26 | B |
| 27 | A |
| 29 | A |
| 33 | A |
| 42 | A |
| 45 | A |
| 54 | B |
| 63 | A |
| 77 | A |
| 88 | A |
| 98 | A |
| 101 | A |
| 104 | A |
| 107 | A |
| 108 | A |
| 112 | A |
| 114 | A |
| 115 | A |
| 116 | A |
| 124 | B |
| 129 | A |
| 134 | A |
| 135 | A |
| 154 | A |
| 157 | A |
| 160 | A |
| 163 | A |
| 166 | A |
| 169 | A |
| 184 | A |
| 193 | A |
| 195 | B |
| 204 | B |
| 205 | A |
| 208 | A |
| 211 | A |
| 212 | A |
| 213 | A |
| 214 | A |
| 215 | A |
| 216 | A |
| 217 | A |
| 219 | A |
| 220 | A |
| 221 | A |
| 227 | A |
| 228 | A |
| 230 | A |

TABLE 16-continued

| Compound No. | Evaluation |
|---|---|
| 231 | A |
| 232 | A |
| 235 | A |
| 236 | A |
| 238 | A |
| 246 | B |
| 323 | A |
| 326 | A |
| 327 | A |
| 328 | A |
| 329 | B |
| 331 | B |
| 333 | B |
| 335 | A |
| 336 | A |
| 338 | A |
| 339 | A |
| 340 | A |
| 341 | A |
| 342 | A |
| 343 | A |
| 344 | B |
| 345 | A |
| 347 | A |
| 348 | B |
| 349 | A |
| 350 | B |
| 351 | A |
| 352 | A |
| 353 | A |
| 354 | A |
| 355 | A |
| 356 | A |
| 357 | B |
| 358 | A |
| 359 | A |
| 360 | A |
| 361 | B |
| 362 | B |
| 363 | A |
| 364 | B |
| 365 | A |
| 366 | A |
| 367 | A |
| 368 | A |
| 369 | A |
| 370 | A |
| 371 | A |
| 372 | A |
| 373 | A |
| 374 | A |
| 376 | A |
| 377 | A |
| 378 | A |
| 379 | A |
| 380 | A |
| 381 | A |
| 382 | A |
| 383 | A |
| 385 | A |
| 386 | A |
| 387 | B |
| 388 | A |
| 389 | A |
| 390 | A |
| 391 | A |
| 392 | A |
| 393 | A |
| 394 | A |
| 395 | A |
| 397 | A |
| 399 | A |
| 401 | A |
| 402 | A |
| 403 | A |
| 405 | A |

TABLE 16-continued

| Compound No. | Evaluation |
|---|---|
| 408 | A |
| 410 | A |
| 411 | B |
| 412 | A |
| 413 | A |
| 414 | A |
| 416 | A |
| 417 | A |
| 418 | A |
| 419 | A |
| 421 | A |
| 422 | A |
| 423 | A |
| 424 | A |
| 425 | A |
| 426 | A |
| 427 | A |
| 429 | A |
| 430 | A |
| 431 | A |
| 432 | A |
| 439 | A |
| 440 | A |
| 451 | A |
| 452 | A |
| 453 | A |
| 455 | A |
| 456 | A |
| 462 | A |
| 465 | A |
| 466 | A |
| 467 | A |
| 468 | A |
| 471 | B |
| 477 | A |
| 482 | A |
| 486 | A |
| 492 | A |
| 493 | A |
| 495 | A |
| 496 | B |
| 499 | B |
| 502 | A |
| 506 | A |
| 508 | A |
| 509 | A |
| 510 | A |
| 511 | A |
| 512 | A |
| 513 | A |
| 517 | A |
| 519 | A |
| 523 | A |
| 525 | A |
| 605 | A |
| 606 | A |
| 607 | A |
| 708 | A |
| 768 | A |
| 770 | A |
| Comparative Example X | D |
| Comparative Example Y | D |

Test Example 2

Test on the Effect of Treating Infection by Cucumber Downy Mildew (*Pseudoperonospora cubensis*)

Cucumber seeds (variety: "Sagami hanjiro") were sown at a rate of 10 seeds each in a square PVC (polyvinyl chloride) pot, wherein each side is 9 cm wide. The seeds were allowed to grow in a greenhouse, for 7 days, to the cotyledonous stage. The seedlings were inoculated with a spore suspension of cucumber downy mildew (*Pseudoperonospora cubensis*) fungi and then placed in a moist chamber at 22° C. for 24 hours. After drying in the air, a wettable powder prepared as in Formulation Example 2 was diluted with water to a concentration of 500 ppm of the active ingredient, and the aqueous preparation obtained was then applied at a rate of 10 ml per pot to the cucumber seedlings. The seedlings were then placed in a green house. On the seventh day after the inoculation, the extent of lesions was rated in accordance with the standards of evaluation shown in Table 15 in order to secure the effect of treating with the compounds according to the present invention. The results of the test are given in Table 17.

TABLE 17

| Compound No. | Evaluation |
| --- | --- |
| 4 | B |
| 10 | A |
| 13 | A |
| 16 | A |
| 19 | B |
| 29 | A |
| 33 | A |
| 42 | A |
| 45 | A |
| 54 | B |
| 63 | A |
| 77 | A |
| 88 | B |
| 104 | A |
| 107 | A |
| 108 | B |
| 114 | B |
| 115 | A |
| 116 | A |
| 124 | A |
| 129 | B |
| 134 | A |
| 135 | A |
| 154 | A |
| 157 | A |
| 160 | A |
| 163 | A |
| 184 | B |
| 212 | A |
| 213 | A |
| 215 | A |
| 216 | B |
| 219 | A |
| 220 | B |
| 221 | A |
| 228 | B |
| 230 | B |
| 231 | A |
| 232 | A |
| 238 | A |
| 333 | A |
| 335 | A |
| 336 | A |
| 340 | B |
| 341 | B |
| 342 | A |
| 345 | A |
| 348 | B |
| 349 | A |
| 351 | A |
| 352 | A |
| 353 | A |
| 354 | A |
| 355 | A |
| 356 | A |
| 358 | A |
| 360 | B |

TABLE 17-continued

| Compound No. | Evaluation |
| --- | --- |
| 365 | A |
| 367 | B |
| 368 | A |
| 369 | A |
| 371 | A |
| 374 | A |
| 376 | A |
| 378 | A |
| 381 | B |
| 382 | A |
| 383 | A |
| 385 | A |
| 386 | A |
| 388 | B |
| 394 | A |
| 395 | A |
| 397 | A |
| 399 | A |
| 401 | A |
| 402 | B |
| 405 | B |
| 414 | A |
| 416 | A |
| 417 | A |
| 418 | A |
| 419 | B |
| 423 | A |
| 424 | A |
| 425 | A |
| 427 | A |
| 429 | A |
| 439 | A |
| 451 | A |
| 452 | A |
| 453 | A |
| 455 | A |
| 456 | A |
| 462 | A |
| 465 | A |
| 466 | A |
| 467 | B |
| 468 | A |
| 477 | B |
| 486 | B |
| 492 | A |
| 495 | A |
| 499 | B |
| 502 | A |
| 506 | A |
| 508 | A |
| 509 | A |
| 513 | A |
| 517 | A |
| 519 | B |
| 523 | A |
| 606 | A |
| 607 | B |
| 708 | A |
| 768 | B |
| 770 | B |
| Comparative Example X | D |
| Comparative Example Y | D |

Test Example 3

Test on the Effect of Preventing Infection by Tomato Late Blight (*Phytophthora infestans*)

One tomato seedling (variety: "Ponterosa") was transplanted into each porcelain pot (diameter: 12 cm) and grown in a greenhouse. A wettable powder prepared as in Formulation Example 2 was diluted with water to a concentration of 500 ppm of the active ingredient, and the aqueous preparation obtained was then applied at a rate of 20 ml per pot to the tomato seedlings at their 6- or 7-leaf stage. After drying in the air, the plant was inoculated with a zoosporangium suspension of tomato late blight (*Phytophthora infestans*) fungi and then placed in a moist chamber at 22° C. On the fourth day after the inoculation, index of incidence was determined based on the size of the affected area as shown in Table 18. The degree of damage was calculated according to Equation (1) and the index of incidence and the ability to prevent the disease (controlling activity) was calculated according to Equation (2). The results are shown in Table 19.

TABLE 18

| Incidence Index | Affected Area |
| --- | --- |
| 0 | No lesions |
| 1 | Less than 5% |
| 2 | 5% or more and less than 33.3% |
| 3 | 33.3% or more and less than 66.6% |
| 4 | 66.6% or more |

Degree of Damage (%) = Equation (1)

$$\frac{\Sigma (\text{Incidence Index} \times \text{Number of Proper Leaves})}{4 \times \text{Number of Leaves Examined}} \times 100$$

Controlling Activity (%) = Equation (2)

$$\left(1 - \frac{\text{Degree of Damage}}{\text{Degree of Damage in Untreated Plot}}\right) \times 100$$

TABLE 19

| Compound No. | Controlling Activity (%) |
| --- | --- |
| 2 | 100 |
| 4 | 100 |
| 6 | 100 |
| 7 | 100 |
| 10 | 100 |
| 13 | 100 |
| 16 | 100 |
| 17 | 100 |
| 19 | 100 |
| 23 | 100 |
| 27 | 100 |
| 29 | 100 |
| 33 | 100 |
| 42 | 100 |
| 45 | 100 |
| 63 | 100 |
| 77 | 100 |
| 88 | 100 |
| 98 | 100 |
| 101 | 100 |
| 104 | 100 |
| 107 | 100 |
| 108 | 100 |
| 112 | 100 |
| 115 | 100 |
| 116 | 100 |
| 129 | 100 |
| 134 | 100 |
| 135 | 100 |
| 154 | 100 |
| 157 | 100 |
| 160 | 100 |
| 163 | 100 |
| 166 | 100 |
| 169 | 100 |

TABLE 19-continued

| Compound No. | Controlling Activity (%) |
| --- | --- |
| 184 | 100 |
| 193 | 100 |
| 213 | 100 |
| 215 | 100 |
| 217 | 100 |
| 220 | 100 |
| 221 | 100 |
| 228 | 100 |
| 231 | 100 |
| 232 | 100 |
| 235 | 100 |
| 238 | 100 |
| 323 | 100 |
| 326 | 100 |
| 336 | 100 |
| 345 | 100 |
| 352 | 100 |
| 356 | 100 |
| 359 | 100 |
| 360 | 100 |
| 364 | 100 |
| 365 | 100 |
| 369 | 100 |
| 371 | 100 |
| 372 | 100 |
| 373 | 100 |
| 374 | 100 |
| 378 | 100 |
| 379 | 100 |
| 380 | 100 |
| 381 | 100 |
| 382 | 100 |
| 386 | 100 |
| 388 | 100 |
| 390 | 100 |
| 391 | 100 |
| 393 | 100 |
| 394 | 100 |
| 395 | 100 |
| 397 | 100 |
| 399 | 100 |
| 401 | 100 |
| 402 | 100 |
| 403 | 100 |
| 404 | 100 |
| 405 | 100 |
| 408 | 100 |
| 414 | 100 |
| 417 | 100 |
| 418 | 100 |
| 423 | 100 |
| 424 | 100 |
| 427 | 100 |
| 430 | 100 |
| 439 | 100 |
| 440 | 100 |
| 451 | 100 |
| 462 | 100 |
| 465 | 100 |
| 466 | 100 |
| 467 | 100 |
| 477 | 100 |
| 482 | 100 |
| 492 | 100 |
| 495 | 100 |
| 502 | 100 |
| 508 | 100 |
| 509 | 100 |
| 513 | 100 |
| 519 | 100 |
| 523 | 100 |
| 605 | 100 |
| 606 | 100 |
| 607 | 100 |
| 708 | 100 |

TABLE 19-continued

| Compound No. | Controlling Activity (%) |
|---|---|
| 768 | 100 |
| 770 | 100 |
| Comparative Example X | 0 |
| Comparative Example Y | 0 |

Test Example 4

Test on the Effect of Preventing Infection by Grape Downy Mildew (*Plasmopara viticola*)

Grape rooted cuttings (variety: "Kyoho"), each grown from a cutting and pruned, was grown in a porcelain pot (diameter: 12 cm) and maintained in a greenhouse. A wettable powder prepared as in Formulation Example 2 was diluted with water to a concentration of 500 ppm of the active ingredient, and the aqueous preparation obtained was then applied at a rate of 20 ml per pot to the grape seedlings at their 4- or 5-leaf stage. After drying in the air, the plant was inoculated with a zoosporangium suspension of grape downy mildew (*Plasmopara viticola*) fungi and then placed in a moist chamber at 22° C. for 24 hours. On the seventh day in the greenhouse after the inoculation, the plant was again placed in a moist chamber at 22° C. for 24 hours to cultivate conidiospores. The incidence area where conidiospores grew on each leaf was examined and the incidence index determined according to the standards shown in Table 18. The degree of damage was calculated according to Equation (1) and the incidence index and the ability to prevent the disease (controlling activity) was calculated according to Equation (2). The results of the test are shown in Table 20.

TABLE 20

| Compound No. | Controlling Activity (%) |
|---|---|
| 2 | 100 |
| 4 | 100 |
| 6 | 100 |
| 7 | 100 |
| 10 | 100 |
| 13 | 100 |
| 16 | 100 |
| 17 | 100 |
| 19 | 100 |
| 23 | 100 |
| 27 | 100 |
| 29 | 100 |
| 33 | 100 |
| 42 | 100 |
| 45 | 100 |
| 63 | 100 |
| 77 | 100 |
| 88 | 100 |
| 98 | 100 |
| 101 | 100 |
| 104 | 100 |
| 107 | 100 |
| 108 | 100 |
| 112 | 100 |
| 115 | 100 |
| 116 | 100 |
| 129 | 100 |
| 134 | 100 |
| 135 | 100 |
| 154 | 100 |
| 157 | 100 |
| 160 | 100 |
| 163 | 100 |
| 166 | 100 |
| 169 | 100 |
| 184 | 100 |
| 193 | 100 |
| 213 | 100 |
| 215 | 100 |
| 217 | 100 |
| 220 | 100 |
| 221 | 100 |
| 228 | 100 |
| 231 | 100 |
| 232 | 100 |
| 235 | 100 |
| 238 | 100 |
| 323 | 100 |
| 326 | 100 |
| 336 | 100 |
| 345 | 100 |
| 352 | 100 |
| 356 | 100 |
| 359 | 100 |
| 360 | 100 |
| 364 | 100 |
| 365 | 100 |
| 369 | 100 |
| 371 | 100 |
| 372 | 100 |
| 373 | 100 |
| 374 | 100 |
| 378 | 100 |
| 379 | 100 |
| 380 | 100 |
| 381 | 100 |
| 382 | 100 |
| 386 | 100 |
| 388 | 100 |
| 390 | 100 |
| 391 | 100 |
| 393 | 100 |
| 394 | 100 |
| 395 | 100 |
| 397 | 100 |
| 399 | 100 |
| 401 | 100 |
| 402 | 100 |
| 403 | 100 |
| 404 | 100 |
| 405 | 100 |
| 408 | 100 |
| 414 | 100 |
| 417 | 100 |
| 418 | 100 |
| 423 | 100 |
| 424 | 100 |
| 427 | 100 |
| 430 | 100 |
| 439 | 100 |
| 440 | 100 |
| 451 | 100 |
| 462 | 100 |
| 465 | 100 |
| 466 | 100 |
| 467 | 100 |
| 477 | 100 |
| 482 | 100 |
| 492 | 100 |
| 495 | 100 |
| 502 | 100 |
| 508 | 100 |

TABLE 20-continued

| Compound No. | Controlling Activity (%) |
|---|---|
| 509 | 100 |
| 513 | 100 |
| 519 | 100 |
| 523 | 100 |
| 605 | 100 |
| 606 | 100 |
| 607 | 100 |
| 708 | 100 |
| 768 | 100 |
| 770 | 100 |
| Comparative Example X | 0 |
| Comparative Example Y | 0 |

What is claimed is:

1. An amino-acid amide represented by the formula:

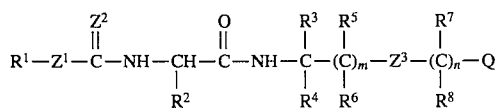

wherein $R^1$ represents
a lower alkyl group (optionally having at least one same or different substituent selected from the group consisting of a halogen atom, an alkoxy group, and a cyano group),
a lower alkenyl group,
a lower alkynyl group,
a cycloalkyl group (optionally having at least one same or different substituent selected from the group consisting of methyl group and a halogen atom),
a cycloalkylalkyl group,
a cycloalkenyl group,
an alkylene oxide group,
an aralkyl group (optionally having at least one same or different substituent selected from the group consisting of a methyl group, a cyano group, and a nitro group),
a phenyl group (optionally having at least one same or different substituent selected from the group consisting of
a halogen atom,
a lower alkyl group which may be substituted with a same or different halogen atom,
a lower alkoxy group which may be substituted with a same or different halogen atom,
a cyano group, and
a nitro group), or
a heterocyclic group, $R^2$ represents an ethyl group, an n-propyl group, an isopropyl group, an isobutyl group, a sec-butyl group, a tert-butyl group, an alkenyl group, a cycloalkyl group, a phenyl group (optionally having at least one substituent of halogen atom), $R^3$ represents a hydrogen atom or a lower alkyl group, $R^4$ represents a hydrogen atom, a lower alkyl group, or a cyano group, $R^5$, $R^6$, and $R^7$ independently represent a hydrogen atom or a lower alkyl group, $R^8$ represents a hydrogen atom, a lower alkyl group, an aralkyl group, a phenyl group, an alkoxycarbonyl group, or a cyano group, $Z^1$ and $Z^2$ independently represent an oxygen atom or a sulfur atom, $Z^3$ represents
an oxygen atom,
a group N—$R^{10}$ (wherein $R^{10}$ represents a hydrogen atom, a methyl group, a methylcarbonyl group, a phenylcarbonyl group, a methoxycarbonyl group, or a methoxymethyl group),
a sulfinyl group,
a sulfonyl group,
a group COO,
a group $CONR^{11}$ (wherein $R^{11}$ represents a hydrogen atom or a lower alkyl group), Q represents
a phenyl group (optionally having at least one same or different substituent selected from the group consisting of
a halogen atom,
a lower alkyl group which may be substituted with at least one same or different halogen atom,
a lower alkoxy group which may be substituted with a same or different halogen atom,
a cyano group,
a nitro group,
a lower alkoxycarbonyl group,
a methylsulfonyl group,
a methylsulfinyl group,
a methylthio group which may be substituted with a halogen atom,
a dimethylamino group,
a phenylsulfonyl group,
a acyl group, and
a phenyl group), m represents an integer from 0 to 2, and
n represents 0 or 1.

2. An amino-acid amide represented by the formula:

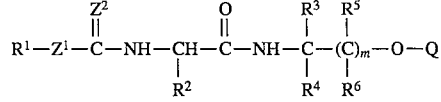

wherein $R^1$ represents
a lower alkyl group (optionally having at least one same or different substituent selected from the group consisting of a halogen atom, an alkoxy group, and a cyano group),
a lower alkenyl group,
a lower alkynyl group,
a cycloalkyl group (optionally having at least one same or different substituent selected from the group consisting of methyl group and a halogen atom),
a cycloalkylalkyl group,
a cycloalkenyl group,
an alkylene oxide group,
an aralkyl group (optionally having at least one same or different substituent selected from the group consisting of a methyl group, a cyano group, and a nitro group),
a phenyl group (optionally having at least one same or different substituent selected from the group consisting of
a halogen atom,
a lower alkyl group which may be substituted with a same or different halogen atom,
a lower alkoxy group which may be substituted with a same or different halogen atom,
a cyano group, and a nitro group), or a heterocyclic group, $R^2$ represents an ethyl group, an n-propyl group, an isopropyl group, an isobutyl group, a sec-butyl group, a tert-butyl group, an alkenyl group, a cycloalkyl group, a phenyl group (optionally having at least one substituent of halogen atom), $R^3$ represents a hydrogen atom or a lower alkyl group, $R^4$ represents a hydrogen atom, a lower alkyl group, or a cyano group, $R^5$, $R^6$, and $R^7$ independently represent a hydrogen atom or a lower alkyl group, $R^8$ represents a hydrogen atom, a lower alkyl group, an aralkyl group, a phenyl group, an alkoxycarbonyl group, or a cyano group, $Z^1$ and $Z^2$ independently represent an oxygen atom or a sulfur atom, Q represents
   a phenyl group having at least one same or different substituent selected from the group consisting of
   a halogen atom,
   a lower alkyl group which may be substituted with at least one same or different halogen atom,
   a lower alkoxy group which may be substituted with a same or different halogen atom,
   a cyano group,
   a nitro group,
   a lower alkoxycarbonyl group,
   a methylsulfonyl group,
   a methylsulfinyl group,
   a methylthio group which may be substituted with a halogen atom,
   a dimethylamino group,
   a phenylsulfonyl group,
   a acyl group, and
   a phenyl group, and m represents an integer from 0 to 2.

3. An amino-acid amide as recited in claim 1, which is represented by the formula:

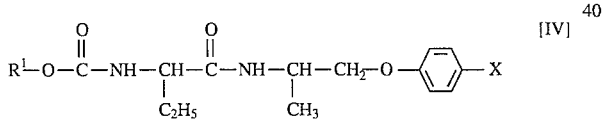

[IV]

wherein $R^1$ represents an isopropyl group, a tert-butyl group, a cyclopentyl group, or a phenyl group (optionally having at least one same or different substituent selected from the group consisting of a halogen atom, a methyl group, a methoxy group, and a nitro group), and X represents a halogen atom, a cyano group, or a nitro group.

4. An amino-acid amide as recited in claim 1, which is represented by the formula:

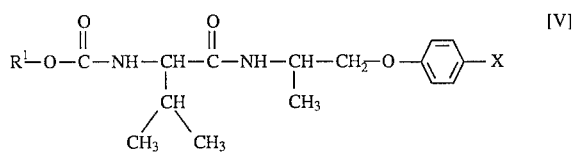

[V]

wherein $R^1$ represents an isopropyl group, a tert-butyl group, a cyclopentyl group, a cyclohexyl group which may be substituted with a methyl group, or a phenyl group (optionally having at least one same or different substituent selected from the group consisting of a halogen atom, a methyl group, a methoxy group, a trifluoromethyl group, a trifluoromethoxy group, and a nitro group), and X represents a halogen atom, a cyano group, or a nitro group.

5. An amino-acid amide as recited in claim 1, which is represented by the formula:

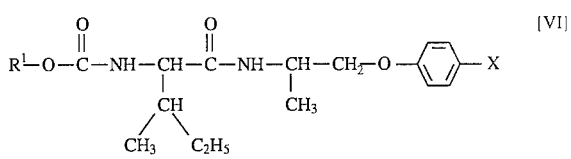

[VI]

wherein $R^1$ represents an isopropyl group, a tert-butyl group, a cyclopentyl group, or a phenyl group (optionally having at least one same or different substituent selected from the group consisting of a halogen atom, a methyl group, a methoxy group, and a nitro group), and X represents a halogen atom, a cyano group, or a nitro group.

6. An amino-acid amide as recited in claim 1, which is represented by the formula:

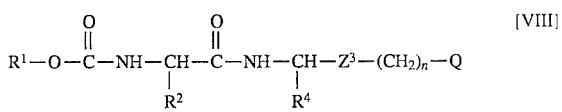

[VIII]

wherein $R^1$ represents a $C_1$–$C_6$ alkyl group, a $C_3$–$C_8$ cycloalkyl group, or a phenyl group (optionally having at least one substituent halogen atom), $R^2$ represents an ethyl group, an isopropyl group, or a sec-butyl group, $R^4$ represents a hydrogen atom or a $C_1$–$C_3$ alkyl group, $Z^3$ represents a group COO, a group $CONR^{11}$ (wherein $R^{11}$ represents a hydrogen atom or a $C_1$–$C_3$ alkyl group), Q represents a phenyl group (optionally having at least one same or different substituent selected from the group consisting of a halogen atom, a $C_1$–$C_3$ alkyl group, a $C_1$–$C_3$ alkoxy group, and a cyano group), and n represents 0 or 1.

7. An agricultural or horticultural fungicidal composition which includes an effective amount of an amino-acid amide as recited in claim 1.

8. An agricultural or horticultural fungicidal composition which includes an effective amount of an amino-acid amide as claimed in claim 1.

9. An agricultural or horticultural fungicidal composition which includes an effective amount of an amino-acid amide as claimed in claim 2.

* * * * *